US007582301B1

(12) United States Patent
Bridon et al.

(10) Patent No.: US 7,582,301 B1
(45) Date of Patent: Sep. 1, 2009

(54) LONG-LASTING ANTIVIRAL FUSION INHIBITOR PEPTIDE CONJUGATES COMPRISING ALBUMIN AND HUMAN IMMUNODEFICIENCY VIRUS (HIV) PEPTIDES

(75) Inventors: Dominique P. Bridon, Outremont (CA); Robert P. Dufresne, Wellseley, MA (US); Nissab Boudjellab, Dorval (CA); Martin Robitaille, Terrasse-Vaudreuil (CA); Peter G. Milner, Los Altos Hills, CA (US)

(73) Assignee: Conjuchem Biotechnologies, Inc., Montreal, Quebec (CA)

( * ) Notice: Subject to any disclaimer, the term of this patent is extended or adjusted under 35 U.S.C. 154(b) by 0 days.

(21) Appl. No.: 09/623,533

(22) PCT Filed: May 17, 2000

(86) PCT No.: PCT/US00/13651

§ 371 (c)(1),
(2), (4) Date: Sep. 5, 2000

(87) PCT Pub. No.: WO00/69902

PCT Pub. Date: Nov. 23, 2000

(51) Int. Cl.
*A61K 39/385* (2006.01)
*A61K 39/21* (2006.01)
(52) U.S. Cl. .............................. 424/196.11; 424/188.1; 424/208.1
(58) Field of Classification Search ............ 424/196.11, 424/188.1, 208.1
See application file for complete search history.

(56) References Cited

U.S. PATENT DOCUMENTS

| 4,652,629 | A | * | 3/1987 | Patrick et al. ................ 530/326 |
| 5,116,944 | A | * | 5/1992 | Sivam et al. ................ 530/362 |
| 5,464,933 | A | * | 11/1995 | Bolognesi et al. ........... 530/324 |
| 5,612,034 | A | | 3/1997 | Pouletty et al. ........... 424/184.1 |
| 5,614,487 | A | | 3/1997 | Battersby et al. |
| 6,013,263 | A | | 1/2000 | Barney et al. ............. 424/212.2 |
| 6,017,536 | A | | 1/2000 | Barney et al. ............. 424/188.1 |
| 6,103,236 | A | | 8/2000 | Suzawa et al. ........... 424/183.1 |
| 6,107,489 | A | * | 8/2000 | Krantz et al. ............. 548/338.1 |
| 6,258,782 | B1 | * | 7/2001 | Barney et al. ................ 514/13 |
| 7,090,851 | B1 | | 8/2006 | Bridon et al. |
| 2005/0065075 | A1 | | 3/2005 | Erickson et al. |
| 2005/0070475 | A1 | | 3/2005 | Bridon et al. |

FOREIGN PATENT DOCUMENTS

| EP | 0602290 | 6/1994 |
| WO | 9510302 | 4/1995 |
| WO | WO 95/10302 | 4/1995 |
| WO | 96/19495 | 6/1996 |
| WO | WO 96/19495 | * 6/1996 |
| WO | 9924074 | 5/1999 |
| WO | 9924075 | 5/1999 |
| WO | WO 99/24074 | 5/1999 |
| WO | WO 99/24075 | 5/1999 |
| WO | 9948536 | 9/1999 |
| WO | WO 99/48536 | 9/1999 |
| WO | WO 00/69902 | 11/2000 |
| WO | 00/76550 | 12/2000 |
| WO | 00/76551 | 12/2000 |
| WO | WO 2005/108418 | 11/2005 |

OTHER PUBLICATIONS

Wang et al., Apr. 1995, "Sequence diversity of V1 and V2 domains of gp120 from human immunodeficiency virus type 1: lack o correlation with viral phenotype", J. Virol. 69(4):2708-2715.*

Kwong, P. D., et al., Feb. 2000, "Oligomeric modeling and electrostatic analysis of the gp120 envelope glycoprotein of human immunodeficiency virus", J. Virol. 74(4):1961-1972.*

Yang, X., et al., May 2000, "Modifications that stabilize human immunodeficiency virus envelope glycoprotein trimers in solution", J. Virol. 74(10):4746-4754.*

Sanders, R. W., et al., Sep. 2002, "Stabilization of the soluble, cleaved, trimeric form of the envelope glycoprotein complex of human immunodeficiency virus type 1", J. Virol. 76(17):8875-8889.*

Tolman, R. L., et al., 1993, "Cyclic V3-loop-related HIV-1 conjugate vaccines: synthesis, conformation and immunological properties", Int. J. Peptide Protein Res. 41:455-466.*

Narazaki, R., et al., 1996, Covalent binding between bucillamine derivatives and human serum albumin, Pharm. Res. 13(9): 1317-1321.*

Proc. Natl. Acad. Sci., 1996, 93 (5), 2186-2191.

Anti-Cancer Drugs, 1998, 8, 677-685.

U.S. Appl. No. 09/657,336, filed Sep. 2000, Bridon, et al.

U.S. Appl. No. 10/950,010, filed Sep. 24, 2004, Bridon et al.

Christophe Boeckler, "Immunogenicity of New Heterobifunctional Cross-Linking Reagents Used in the Conjugation . . . ", Journal of Immunological Methods, 1996, vol. 191, pp. 1-10.

Carl Wild, "A synthetic Peptide Inhibitor of Human Immunodeficiency Virus Replication : Correlation . . . ", Proc. Natl. Acad. Sci., Nov. 1992, vol. 89, pp. 10537-10541.

Joseph G. Sodroski, "HIV-1 Entry Inhibitors in the Side Pocket", Cell, Oct. 29, 1999, vol. 99, pp. 243-246.

(Continued)

*Primary Examiner*—Jeffrey S. Parkin
(74) *Attorney, Agent, or Firm*—Lowrie, Lando & Anastasi, LLP

(57) ABSTRACT

Peptides exhibiting anti-viral and anti-fusogenic activity are modified to provide greater stability and improved half-life in vivo. The selected peptides include fusion inhibitors DP178 and DP107 and related peptides and analogs thereof. The modified peptides are capable of forming covalent bonds with one or more blood components, preferably a mobile blood component.

47 Claims, No Drawings

OTHER PUBLICATIONS

Aran F. Labrijn, "Access of Antibody Molecules to the Conserved Coreceptor Binding Site on Glycoprotein gp120 . . . " Journal of Virology, Oct. 2003, vol. 77, pp. 10557-10565.

Nasar M. Qureshi, "Characterization of a Putative Cellular Receptor for HIV-1 Transmembrane Glycoprotein Using Synthetic Peptides" AIDS, 1990, vol. 4, pp. 553-558.

Kuiken C, Foley B, Hahn B, Marx P, McCutchan F, Mellors J, Wolinsky S, and Korber B, editors. *HIV Sequence Compendium 2001*, Published by Theoretical Biology and Biophysics Group, Los Alamos National Laboratory, 2002: 288-289.

Lawless, Mary K. et al. "HIV-1 Membrane Fusion Mechanism: Structural Studies of the Interactions between Biologically-Active Peptides from gp41" *Biochemistry* 35, 1996: 13697-13708.

Archakov, Alexander I. et al. (2003) "Protein-Protein Interactions as a Target for Drugs in Proteomics," Proteomics, 3: 380-391.

Chen, Chin-Ho et al. (Jun. 1995) "A Molecular Clasp in the Human Immunodeficiency Virus (HIV) Type 1 TM Protein Determines the Anti-HIV Activity of gp41 Derivatives: Implication for Viral Fusion," Journal of Virology, 69(6): 3771-3777.

Davies, David R. et al. (Jan. 1996) "Interactions of Protein Antigens with Antibodies," Proc. Natl. Acad. Sci. USA, 93: 7-12.

Jiang, Shibo et al. (2002) "Peptide and Non-peptide HIV Fusion Inhibitors," Current Pharmaceutical Design, 8: 563-580.

Jones, Susan et al. (Jan. 1996) "Principles of Protein-Protein Interactions," Proc. Natl. Acad. Sci. USA, 93: 13-20.

Shugars, Diane C. et al. (May 1996) "Biophysical Characterization of Recombinant Proteins Expressing the Leucine Zipper-Like Domain of the Human Immunodeficiency Virus Type 1 Transmembrane Protein gp41," Journal of Virology, 70(5): 2982-2991.

Archakov, Alexander I. et al. (2003) "Protein-Protein Interactions as a Target for Drugs in Proteomics," Proteomics, 3:380-391.

Boeckler, Christophe "Immunogenicity of New Heterobifunctional Cross-Linking Reagants Used in the Conjugation . . . ", Journal of Immunological Methods, (1996), vol. 191:pp. 1-10.

Christodoulou, John et al. "H NMR of albumin in human blood plasma: drug binding and redox reactions at $Cys^{34}$", *FEBS Letters* 376:pp. 1-5 (1995).

Davies, David R. et al. (Jan. 1996) "Interactions of Protein Antigens with Antibodies," Proc. Natl. Acad. Sci. USA, 93:7-12.

Jiang, Shibo et al. (2002) "Peptide and Non-peptide HIV Fusion Inhibitors," Current Pharmaceutical Design, 8:563-580.

Jones, Susan et al. (Jan. 1996) "Principles of Protein-Protein Interactions," Proc. Natl. Acad. Sci. USA, 93:13-20.

Kwong, Peter D. et al. (Feb. 2000) "Oligomeric Modeling and Electrostatic Analysis of the gp120 Envelope Glycoprotein of Human Immunodeficiency Virus," Journal of Virology, 74(4):1961-1972.

Labrijn, Aran F. "Access of Antibody Molecules to the Conserved Coreceptor Binding Site of Glycoprotein gp120 . . . " Journal of Virology, (Oct. 2003), vol. 77:pp. 10557-10565.

Lamber, D.M. et al. "Peptides from conserved regions of paramyxovirus fusion (F) proteins are potent inhibitors of viral fusion", (Nov. 1995) Medical Sciences, pp. 2186-2191.

Lawless, Mary K. et al. (1996) "HIV-1 Membrane Fusion Mechanism: Structural Studies of the Interactions between Biologically-Active Peptides from gp41," Biochemistry, 35: 13697-13708.

Narazaki, Ryuichi, et al. "Covalent Binding Between Bucillamine Derivatives and Human Serum Albumin" *Pharmaceutical Research*, vol. 13, No. 9: pp. 1317-1321 (1996).

Qureshi, Nasar M. "Characterization of a Putative Cellular Receptor for HIV-1 Transmembrane Glycoprotein Using Synthetic Peptides" AIDS, (1990) vol. 4:pp. 553-558.

Sanders, Rogier W. et al. (Sep. 2002) "Stabilization of the Soluble, Cleaved, Trimeric Form of the Envelope Glycoprotein Complex of Human Immunodeficiency Virus Type 1," Journal of Virology, 76(17) 8875-8889.

Sodroski, Joseph G. "HIV-1 Entry Inhibitors in the Side Pocket", Cell, (Oct. 29, 1999), vol. 99:pp. 243-246.

Tolman, R.L. et al. (1993) "Cyclic V3-Loop-Related HIC-1 Conjugate Vaccines: Synthesis, Conformation and Immunological Properties" Int. J. Peptide Protein Res. 41:455-466.

Wang, Ning et al. (Apr. 1995) "Sequence Diversity of V1 and V2 Domains of gp120 from Human Immunodeficiency Virus Type 1: Lack of Correlation with Viral Phenotype," Journal of Virology, 69(4): 2708-2715.

Wild, Carl "A synthetic Peptide inhibitor of Human Immunodeficiency Virus Replication: Correlation . . . ", Proc. Natl. Acad. Sci., (Nov. 1992) vol. 89:pp. 10537-10541.

Yang, Xinzhen et al. (May 2000) "Modifications that Stabilize Human Immunodeficiency Virus Envelope Glycoprotein Trimers in Solution," Journal of Virology, 74(10): 4746-4754.

Decision from Appeal Board dated Jul. 27, 2007.

Decision from Opposition Division dated Feb. 1, 2005.

\* cited by examiner

SEQUENCE LISTING

<160> NUMBER OF SEQ ID NOS: 545

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2

```
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Asn Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
            20                  25                  30

Arg Tyr Leu Lys Asp Gln
        35

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Tyr Thr Asn Thr Ile Tyr Thr Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 4
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
            20                  25                  30

Trp Asn Trp Phe
        35

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Tyr Thr Ser Leu Ile Tyr Ser Leu Leu Glu Lys Ser Gln Thr Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

```
<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Leu Glu Ala Asn Ile Ser Lys Ser Leu Glu Gln Ala Gln Ile Gln Gln
1               5                   10                  15

Glu Lys Asn Met Tyr Glu Leu Gln Lys Leu Asn Ser Trp Asp Ile Phe
            20                  25                  30

Gly Asn Trp Phe
        35

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 8
<211> LENGTH: 41
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Cys Gly Gly Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Gln Gln Leu Leu Asp Val Val Lys Arg Gln Gln Glu Met Leu Arg Leu
1               5                   10                  15

Thr Val Trp Gly Thr Lys Asn Leu Gln Ala Arg Val Thr Ala Ile Glu
            20                  25                  30

Lys Tyr Leu Lys Asp Gln
        35
```

```
<210> SEQ ID NO 10
<211> LENGTH: 46
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Tyr Thr Ser Val Ile Thr Ile Glu Leu Ser Asn Ile Lys Glu Asn Lys
 1               5                  10                  15

Cys Asn Gly Ala Lys Val Lys Leu Ile Lys Gln Glu Leu Asp Lys Tyr
            20                  25                  30

Lys Asn Ala Val Thr Glu Leu Gln Leu Leu Met Gln Ser Thr
        35                  40                  45

<210> SEQ ID NO 11
<211> LENGTH: 54
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Ala Ser Gly Val Ala Val Ser Lys Val Leu His Leu Glu Gly Glu Val
 1               5                  10                  15

Asn Lys Ile Ala Leu Leu Ser Thr Asn Lys Ala Val Val Ser Leu Ser
            20                  25                  30

Asn Gly Val Ser Val Leu Thr Ser Lys Val Leu Asp Leu Lys Asn Tyr
        35                  40                  45

Ile Asp Lys Gln Leu Leu
    50

<210> SEQ ID NO 12
<211> LENGTH: 53
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Gly Glu Pro Ile Ile Asn Phe Tyr Asp Pro Leu Val Phe Pro Ser Asp
 1               5                  10                  15

Glu Phe Asp Ala Ser Ile Ser Gln Val Asn Glu Lys Ile Asn Gln Ser
            20                  25                  30

Leu Ala Phe Ile Arg Lys Ser Asp Glu Leu Leu His Asn Val Asn Ala
        35                  40                  45

Gly Lys Ser Thr Thr
    50

<210> SEQ ID NO 13
<211> LENGTH: 48
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Tyr Thr Ser Val Ile Thr Ile Glu Leu Ser Asn Ile Lys Glu Asn Lys
 1               5                  10                  15
```

-continued

Cys Asn Gly Thr Asp Ala Lys Val Lys Leu Ile Lys Gln Glu Leu Asp
            20                  25                  30

Lys Tyr Lys Asn Ala Val Thr Glu Leu Gln Leu Leu Met Gln Ser Thr
        35                  40                  45

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Tyr Thr Ser Val Ile Thr Ile Glu Leu Ser Asn Ile Lys Glu Asn Lys
  1               5                  10                  15

Cys Asn Gly Asp Ala Lys Val Lys Leu Ile Lys Gln Glu Leu Asp Lys
            20                  25                  30

Tyr Lys

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Thr Ser Val Ile Thr Ile Glu Leu Ser Asn Ile Lys Glu Asn Lys Cys
  1               5                  10                  15

Asn Gly Asp Ala Lys Val Lys Leu Ile Lys Gln Glu Leu Asp Lys Tyr
            20                  25                  30

Lys Asn

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Val Ile Thr Ile Glu Leu Ser Asn Ile Lys Glu Asn Lys Cys Asn Gly
  1               5                  10                  15

Asp Ala Lys Val Lys Leu Ile Lys Gln Glu Leu Asp Lys Tyr Lys Asn
            20                  25                  30

Ala Val

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Val Ile Thr Ile Glu Leu Ser Asn Ile Lys Glu Asn Lys Met Asn Gly
  1               5                  10                  15

Asp Ala Lys Val Lys Leu Ile Lys Gln Glu Leu Asp Lys Tyr Lys Asn

```
                20              25              30
Ala Val

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Val Ala Val Ser Lys Val Leu His Leu Glu Gly Glu Val Asn Lys Ile
1               5                   10                  15

Ala Leu Leu Ser Thr Asn Lys Ala Val Val Ser Leu Ser Asn Gly Val
                20                  25                  30

Ser

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

Ala Val Ser Lys Val Leu His Leu Glu Gly Glu Val Asn Lys Ile Ala
1               5                   10                  15

Leu Leu Ser Thr Asn Lys Ala Val Val Ser Leu Ser Asn Gly Val Ser
                20                  25                  30

Val

<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 20

Val Ser Lys Val Leu His Leu Glu Gly Glu Val Asn Lys Ile Ala Leu
1               5                   10                  15

Leu Ser Thr Asn Lys Ala Val Val Ser Leu Ser Asn Gly Val Ser Val
                20                  25                  30

Leu

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Ser Lys Val Leu His Leu Glu Gly Glu Val Asn Lys Ile Ala Leu Leu
1               5                   10                  15

Ser Thr Asn Lys Ala Val Val Ser Leu Ser Asn Gly Val Ser Val Leu
                20                  25                  30

Thr
```

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

Lys Val Leu His Leu Glu Gly Glu Val Asn Lys Ile Ala Leu Leu Ser
 1               5                  10                  15

Thr Asn Lys Ala Val Val Ser Leu Ser Asn Gly Val Ser Val Leu Thr
            20                  25                  30

Ser

<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Leu Glu Gly Glu Val Asn Lys Ile Ala Leu Leu Ser Thr Asn Lys Ala
 1               5                  10                  15

Val Val Ser Leu Ser Asn Gly Val Ser Val Leu Thr Ser Lys Val Leu
            20                  25                  30

Asp

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Gly Glu Val Asn Lys Ile Ala Leu Leu Ser Thr Asn Lys Ala Val Val
 1               5                  10                  15

Ser Leu Ser Asn Gly Val Ser Val Leu Thr Ser Lys Val Leu Asp Leu
            20                  25                  30

Lys

<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Glu Val Asn Lys Ile Ala Leu Leu Ser Thr Asn Lys Ala Val Val Ser
 1               5                  10                  15

Leu Ser Asn Gly Val Ser Val Leu Thr Ser Lys Val Leu Asp Leu Lys
            20                  25                  30

Asn

<210> SEQ ID NO 26

-continued

```
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

Val Asn Lys Ile Ala Leu Leu Ser Thr Asn Lys Ala Val Val Ser Leu
 1               5                  10                  15

Ser Asn Gly Val Ser Val Leu Thr Ser Lys Val Leu Asp Leu Lys Asn
            20                  25                  30

Tyr

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 27

Asn Lys Ile Ala Leu Leu Ser Thr Asn Lys Ala Val Val Ser Leu Ser
 1               5                  10                  15

Asn Gly Val Ser Val Leu Thr Ser Lys Val Leu Asp Leu Lys Asn Tyr
            20                  25                  30

Ile

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 28

Lys Ile Ala Leu Leu Ser Thr Asn Lys Ala Val Val Ser Leu Ser Asn
 1               5                  10                  15

Gly Val Ser Val Leu Thr Ser Lys Val Leu Asp Leu Lys Asn Tyr Ile
            20                  25                  30

Asp

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 29

Ile Ala Leu Leu Ser Thr Asn Lys Ala Val Val Ser Leu Ser Asn Gly
 1               5                  10                  15

Val Ser Val Leu Thr Ser Lys Val Leu Asp Leu Lys Asn Tyr Ile Asp
            20                  25                  30

Lys

<210> SEQ ID NO 30
<211> LENGTH: 33
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 30

Ala Leu Leu Ser Thr Asn Lys Ala Val Val Ser Leu Ser Asn Gly Val
 1               5                  10                  15

Ser Val Leu Thr Ser Lys Val Leu Asp Leu Lys Asn Tyr Ile Asp Lys
            20                  25                  30

Gln

<210> SEQ ID NO 31
<211> LENGTH: 70
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 31

Gly Thr Ile Ala Leu Gly Val Ala Thr Ser Ala Gln Ile Thr Ala Ala
 1               5                  10                  15

Val Ala Leu Val Glu Ala Lys Gln Ala Arg Ser Asp Ile Glu Lys Leu
            20                  25                  30

Lys Glu Ala Ile Arg Asp Thr Asn Lys Ala Val Gln Ser Val Gln Ser
        35                  40                  45

Ser Ile Gly Asn Leu Ile Val Ala Ile Lys Ser Val Gln Asp Tyr Val
    50                  55                  60

Asn Lys Glu Ile Val Pro
 65                  70

<210> SEQ ID NO 32
<211> LENGTH: 56
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 32

Tyr Thr Pro Asn Asp Ile Thr Leu Asn Asn Ser Val Ala Leu Asp Pro
 1               5                  10                  15

Ile Asp Ile Ser Ile Glu Leu Asn Lys Ala Lys Ser Asp Leu Glu Glu
            20                  25                  30

Ser Lys Glu Trp Ile Arg Arg Ser Asn Gln Lys Leu Asp Ser Ile Gly
        35                  40                  45

Asn Trp His Gln Ser Ser Thr Thr
    50                  55

<210> SEQ ID NO 33
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 33

Thr Leu Asn Asn Ser Val Ala Leu Asp Pro Ile Asp Ile Ser Ile Glu
 1               5                  10                  15

Leu Asn Lys Ala Lys Ser Asp Leu Glu Glu Ser Lys Glu Trp Ile Arg
            20                  25                  30
```

Arg Ser Asn
        35

<210> SEQ ID NO 34
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 34

Leu Asn Asn Ser Val Ala Leu Asp Pro Ile Asp Ile Ser Ile Glu Leu
1               5                   10                  15

Asn Lys Ala Lys Ser Asp Leu Glu Glu Ser Lys Glu Trp Ile Arg Arg
            20                  25                  30

Ser Asn Gln
        35

<210> SEQ ID NO 35
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 35

Asn Asn Ser Val Ala Leu Asp Pro Ile Asp Ile Ser Ile Glu Leu Asn
1               5                   10                  15

Lys Ala Lys Ser Asp Leu Glu Glu Ser Lys Glu Trp Ile Arg Arg Ser
            20                  25                  30

Asn Gln Lys
        35

<210> SEQ ID NO 36
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 36

Asn Ser Val Ala Leu Asp Pro Ile Asp Ile Ser Ile Glu Leu Asn Lys
1               5                   10                  15

Ala Lys Ser Asp Leu Glu Glu Ser Lys Glu Trp Ile Arg Arg Ser Asn
            20                  25                  30

Gln Lys Leu
        35

<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 37

Ser Val Ala Leu Asp Pro Ile Asp Ile Ser Ile Glu Leu Asn Lys Ala
1               5                   10                  15

Lys Ser Asp Leu Glu Glu Ser Lys Glu Trp Ile Arg Arg Ser Asn Gln

```
                20              25              30

Lys Leu Asp
        35

<210> SEQ ID NO 38
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 38

Val Ala Leu Asp Pro Ile Asp Ile Ser Ile Glu Leu Asn Lys Ala Lys
 1               5                  10                  15

Ser Asp Leu Glu Glu Ser Lys Glu Trp Ile Arg Arg Ser Asn Gln Lys
                20                  25                  30

Leu Asp Ser
        35

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 39

Ala Leu Asp Pro Ile Asp Ile Ser Ile Glu Leu Asn Lys Ala Lys Ser
 1               5                  10                  15

Asp Leu Glu Glu Ser Lys Glu Trp Ile Arg Arg Ser Asn Gln Lys Leu
                20                  25                  30

Asp Ser Ile
        35

<210> SEQ ID NO 40
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 40

Leu Asp Pro Ile Asp Ile Ser Ile Glu Leu Asn Lys Ala Lys Ser Asp
 1               5                  10                  15

Leu Glu Glu Ser Lys Glu Trp Ile Arg Arg Ser Asn Gln Lys Leu Asp
                20                  25                  30

Ser Ile Gly
        35

<210> SEQ ID NO 41
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 41

Asp Pro Ile Asp Ile Ser Ile Glu Leu Asn Lys Ala Lys Ser Asp Leu
 1               5                  10                  15
```

Glu Glu Ser Lys Glu Trp Ile Arg Arg Ser Asn Gln Lys Leu Asp Ser
            20                  25                  30

Ile Gly Asn
        35

<210> SEQ ID NO 42
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 42

Pro Ile Asp Ile Ser Ile Glu Leu Asn Lys Ala Lys Ser Asp Leu Glu
1               5                   10                  15

Glu Ser Lys Glu Trp Ile Arg Arg Ser Asn Gln Lys Leu Asp Ser Ile
            20                  25                  30

Gly Asn Trp
        35

<210> SEQ ID NO 43
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 43

Ile Asp Ile Ser Ile Glu Leu Asn Lys Ala Lys Ser Asp Leu Glu Glu
1               5                   10                  15

Ser Lys Glu Trp Ile Arg Arg Ser Asn Gln Lys Leu Asp Ser Ile Gly
            20                  25                  30

Asn Trp His
        35

<210> SEQ ID NO 44
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 44

Asp Ile Ser Ile Glu Leu Asn Lys Ala Lys Ser Asp Leu Glu Glu Ser
1               5                   10                  15

Lys Glu Trp Ile Arg Arg Ser Asn Gln Lys Leu Asp Ser Ile Gly Asn
            20                  25                  30

Trp His Gln
        35

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 45

Ile Ser Ile Glu Leu Asn Lys Ala Lys Ser Asp Leu Glu Glu Ser Lys
1               5                   10                  15

-continued

```
Glu Trp Ile Arg Arg Ser Asn Gln Lys Leu Asp Ser Ile Gly Asn Trp
            20                  25                  30

His Gln Ser
        35

<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 46

Ser Ile Glu Leu Asn Lys Ala Lys Ser Asp Leu Glu Glu Ser Lys Glu
 1               5                  10                  15

Trp Ile Arg Arg Ser Asn Gln Lys Leu Asp Ser Ile Gly Asn Trp His
            20                  25                  30

Gln Ser Ser
        35

<210> SEQ ID NO 47
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 47

Ile Glu Leu Asn Lys Ala Lys Ser Asp Leu Glu Glu Ser Lys Glu Trp
 1               5                  10                  15

Ile Arg Arg Ser Asn Gln Lys Leu Asp Ser Ile Gly Asn Trp His Gln
            20                  25                  30

Ser Ser Thr
        35

<210> SEQ ID NO 48
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 48

Glu Leu Asn Lys Ala Lys Ser Asp Leu Glu Glu Ser Lys Glu Trp Ile
 1               5                  10                  15

Arg Arg Ser Asn Gln Lys Leu Asp Ser Ile Gly Asn Trp His Gln Ser
            20                  25                  30

Ser Thr Thr
        35

<210> SEQ ID NO 49
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 49

Thr Ala Ala Val Ala Leu Val Glu Ala Lys Gln Ala Arg Ser Asp Ile
```

```
                1               5                  10                 15
Glu Lys Leu Lys Glu Ala Ile Arg Asp Thr Asn Lys Ala Val Gln Ser
                         20                 25                 30

Val Gln Ser
        35

<210> SEQ ID NO 50
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 50

Ala Val Ala Leu Val Glu Ala Lys Gln Ala Arg Ser Asp Ile Glu Lys
  1               5                  10                 15

Leu Lys Glu Ala Ile Arg Asp Thr Asn Lys Ala Val Gln Ser Val Gln
                 20                 25                 30

Ser Ser Ile
        35

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 51

Leu Val Glu Ala Lys Gln Ala Arg Ser Asp Ile Glu Lys Leu Lys Glu
  1               5                  10                 15

Ala Ile Arg Asp Thr Asn Lys Ala Val Gln Ser Val Gln Ser Ser Ile
                 20                 25                 30

Gly Asn Leu
        35

<210> SEQ ID NO 52
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 52

Val Glu Ala Lys Gln Ala Arg Ser Asp Ile Glu Lys Leu Lys Glu Ala
  1               5                  10                 15

Ile Arg Asp Thr Asn Lys Ala Val Gln Ser Val Gln Ser Ser Ile Gly
                 20                 25                 30

Asn Leu Ile
        35

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 53
```

-continued

Glu Ala Lys Gln Ala Arg Ser Asp Ile Glu Lys Leu Lys Glu Ala Ile
1               5                   10                  15

Arg Asp Thr Asn Lys Ala Val Gln Ser Val Gln Ser Ser Ile Gly Asn
            20                  25                  30

Leu Ile Val
        35

<210> SEQ ID NO 54
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 54

Ala Lys Gln Ala Arg Ser Asp Ile Glu Lys Leu Lys Glu Ala Ile Arg
1               5                   10                  15

Asp Thr Asn Lys Ala Val Gln Ser Val Gln Ser Ser Ile Gly Asn Leu
            20                  25                  30

Ile Val Ala
        35

<210> SEQ ID NO 55
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 55

Lys Gln Ala Arg Ser Asp Ile Glu Lys Leu Lys Glu Ala Ile Arg Asp
1               5                   10                  15

Thr Asn Lys Ala Val Gln Ser Val Gln Ser Ser Ile Gly Asn Leu Ile
            20                  25                  30

Val Ala Ile
        35

<210> SEQ ID NO 56
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 56

Gln Ala Arg Ser Asp Ile Glu Lys Leu Lys Glu Ala Ile Arg Asp Thr
1               5                   10                  15

Asn Lys Ala Val Gln Ser Val Gln Ser Ser Ile Gly Asn Leu Ile Val
            20                  25                  30

Ala Ile Lys
        35

<210> SEQ ID NO 57
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 57

```
Ala Arg Ser Asp Ile Glu Lys Leu Lys Glu Ala Ile Arg Asp Thr Asn
 1               5                  10                  15

Lys Ala Val Gln Ser Val Gln Ser Ser Ile Gly Asn Leu Ile Val Ala
            20                  25                  30

Ile Lys Ser
        35

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 58

Arg Ser Asp Ile Glu Lys Leu Lys Glu Ala Ile Arg Asp Thr Asn Lys
 1               5                  10                  15

Ala Val Gln Ser Val Gln Ser Ser Ile Gly Asn Leu Ile Val Ala Ile
            20                  25                  30

Lys Ser Val
        35

<210> SEQ ID NO 59
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 59

Ser Asp Ile Glu Lys Leu Lys Glu Ala Ile Arg Asp Thr Asn Lys Ala
 1               5                  10                  15

Val Gln Ser Val Gln Ser Ser Ile Gly Asn Leu Ile Val Ala Ile Lys
            20                  25                  30

Ser Val Gln
        35

<210> SEQ ID NO 60
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 60

Lys Leu Lys Glu Ala Ile Arg Asp Thr Asn Lys Ala Val Gln Ser Val
 1               5                  10                  15

Gln Ser Ser Ile Gly Asn Leu Ile Val Ala Ile Lys Ser Val Gln Asp
            20                  25                  30

Tyr Val Asn
        35

<210> SEQ ID NO 61
<211> LENGTH: 35
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 61

Leu Lys Glu Ala Ile Arg Asp Thr Asn Lys Ala Val Gln Ser Val Gln
  1               5                  10                  15

Ser Ser Ile Gly Asn Leu Ile Val Ala Ile Lys Ser Val Gln Asp Tyr
             20                  25                  30

Val Asn Lys
         35

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 62

Ala Ile Arg Asp Thr Asn Lys Ala Val Gln Ser Val Gln Ser Ser Ile
  1               5                  10                  15

Gly Asn Leu Ile Val Ala Ile Lys Ser Val Gln Asp Tyr Val Asn Lys
             20                  25                  30

Glu Ile Val
         35

<210> SEQ ID NO 63
<211> LENGTH: 47
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 63

Thr Trp Gln Glu Trp Glu Arg Lys Val Asp Phe Leu Glu Glu Asn Ile
  1               5                  10                  15

Thr Ala Leu Leu Glu Glu Ala Gln Ile Gln Gln Glu Lys Asn Met Tyr
             20                  25                  30

Glu Leu Gln Lys Leu Asn Ser Trp Asp Val Phe Gly Asn Trp Phe
         35                  40                  45

<210> SEQ ID NO 64
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 64

Trp Gln Glu Trp Glu Arg Lys Val Asp Phe Leu Glu Glu Asn Ile Thr
  1               5                  10                  15

Ala Leu Leu Glu Glu Ala Gln Ile Gln Gln Glu Lys Asn Met Tyr Glu
             20                  25                  30

Leu Gln Lys
         35

<210> SEQ ID NO 65
<211> LENGTH: 35
<212> TYPE: PRT
<213> ORGANISM: Artificial Sequence
<220> FEATURE:
<223> OTHER INFORMATION: Description of Artificial Sequence: synthetic
      peptide
```

<400> SEQUENCE: 65

Gln Glu Trp Glu Arg Lys Val Asp Phe Leu Glu Glu Asn Ile Thr Ala
 1               5                  10                  15

Leu Leu Glu Glu Ala Gln Ile Gln Gln Glu Lys Asn Met Tyr Glu Leu
                20                  25                  30

Gln Lys Leu
        35

<210> SEQ ID NO 66
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 66

Glu Trp Glu Arg Lys Val Asp Phe Leu Glu Glu Asn Ile Thr Ala Leu
 1               5                  10                  15

Leu Glu Glu Ala Gln Ile Gln Gln Glu Lys Asn Met Tyr Glu Leu Gln
                20                  25                  30

Lys Leu Asn
        35

<210> SEQ ID NO 67
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 67

Trp Glu Arg Lys Val Asp Phe Leu Glu Glu Asn Ile Thr Ala Leu Leu
 1               5                  10                  15

Glu Glu Ala Gln Ile Gln Gln Glu Lys Asn Met Tyr Glu Leu Gln Lys
                20                  25                  30

Leu Asn Ser
        35

<210> SEQ ID NO 68
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 68

Glu Arg Lys Val Asp Phe Leu Glu Glu Asn Ile Thr Ala Leu Leu Glu
 1               5                  10                  15

Glu Ala Gln Ile Gln Gln Glu Lys Asn Met Tyr Glu Leu Gln Lys Leu
                20                  25                  30

Asn Ser Trp
        35

<210> SEQ ID NO 69
<211> LENGTH: 35
<212> TYPE: PRT
<213> ORGANISM: Artificial Sequence
<220> FEATURE:
<223> OTHER INFORMATION: Description of Artificial Sequence: synthetic -continued peptide

<400> SEQUENCE: 69

Arg Lys Val Asp Phe Leu Glu Glu Asn Ile Thr Ala Leu Leu Glu Glu
1               5                   10                  15

Ala Gln Ile Gln Gln Glu Lys Asn Met Tyr Glu Leu Gln Lys Leu Asn
            20                  25                  30

Ser Trp Asp
        35

<210> SEQ ID NO 70
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 70

Lys Val Asp Phe Leu Glu Glu Asn Ile Thr Ala Leu Leu Glu Glu Ala
1               5                   10                  15

Gln Ile Gln Gln Glu Lys Asn Met Tyr Glu Leu Gln Lys Leu Asn Ser
            20                  25                  30

Trp Asp Val
        35

<210> SEQ ID NO 71
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 71

Val Asp Phe Leu Glu Glu Asn Ile Thr Ala Leu Leu Glu Glu Ala Gln
1               5                   10                  15

Ile Gln Gln Glu Lys Asn Met Tyr Glu Leu Gln Lys Leu Asn Ser Trp
            20                  25                  30

Asp Val Phe
        35

<210> SEQ ID NO 72
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 72

Asp Phe Leu Glu Glu Asn Ile Thr Ala Leu Leu Glu Glu Ala Gln Ile
1               5                   10                  15

Gln Gln Glu Lys Asn Met Tyr Glu Leu Gln Lys Leu Asn Ser Trp Asp
            20                  25                  30

Val Phe Gly
        35

<210> SEQ ID NO 73
<211> LENGTH: 35
<212> TYPE: PRT
<213> ORGANISM: Artificial Sequence
<220> FEATURE:

-continued

<223> OTHER INFORMATION: Description of Artificial Sequence: synthetic
     peptide

<400> SEQUENCE: 73

Phe Leu Glu Glu Asn Ile Thr Ala Leu Leu Glu Glu Ala Gln Ile Gln
 1               5                  10                  15

Gln Glu Lys Asn Met Tyr Glu Leu Gln Lys Leu Asn Ser Trp Asp Val
            20                  25                  30

Phe Gly Asn
        35

<210> SEQ ID NO 74
<211> LENGTH: 35
<212> TYPE: PRT
<213> ORGANISM: Artificial Sequence
<220> FEATURE:
<223> OTHER INFORMATION: Description of Artificial Sequence: synthetic
     peptide

<400> SEQUENCE: 74

Pro Asp Ala Val Tyr Leu His Arg Ile Asp Leu Gly Pro Pro Ile Ser
 1               5                  10                  15

Leu Glu Arg Leu Asp Val Gly Thr Asn Leu Gly Asn Ala Ile Ala Lys
            20                  25                  30

Leu Glu Asp
        35

<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence: synthetic
     peptide

<400> SEQUENCE: 75

Leu Glu Arg Leu Asp Val Gly Thr Asn Leu Gly Asn Ala Ile Ala Lys
 1               5                  10                  15

Leu Glu Ala Lys Glu Leu Leu Glu Ser Ser Asp Gln Ile Leu Arg Ser
            20                  25                  30

Met Lys

<210> SEQ ID NO 76
<211> LENGTH: 34
<212> TYPE: PRT
<213> ORGANISM: Artificial Sequence
<220> FEATURE:
<223> OTHER INFORMATION: Description of Artificial Sequence: synthetic
     peptide

<400> SEQUENCE: 76

Leu His Arg Ile Asp Leu Gly Pro Pro Ile Ser Leu Glu Arg Leu Asp
 1               5                  10                  15

Val Gly Thr Asn Leu Gly Asn Ala Ile Ala Lys Leu Glu Ala Lys Glu
            20                  25                  30

Leu Leu

<210> SEQ ID NO 77
<211> LENGTH: 34
<212> TYPE: PRT
<213> ORGANISM: Artificial Sequence
<220> FEATURE:
<223> OTHER INFORMATION: Description of Artificial Sequence: synthetic peptide

<400> SEQUENCE: 77

His Arg Ile Asp Leu Gly Pro Pro Ile Ser Leu Glu Arg Leu Asp Val
 1               5                  10                  15

Gly Thr Asn Leu Gly Asn Ala Ile Ala Lys Leu Glu Ala Lys Glu Leu
             20                  25                  30

Leu Glu

<210> SEQ ID NO 78
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 78

Arg Ile Asp Leu Gly Pro Pro Ile Ser Leu Glu Arg Leu Asp Val Gly
 1               5                  10                  15

Thr Asn Leu Gly Asn Ala Ile Ala Lys Leu Glu Ala Lys Glu Leu Leu
             20                  25                  30

Glu Ser

<210> SEQ ID NO 79
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 79

Ile Asp Leu Gly Pro Pro Ile Ser Leu Glu Arg Leu Asp Val Gly Thr
 1               5                  10                  15

Asn Leu Gly Asn Ala Ile Ala Lys Leu Glu Ala Lys Glu Leu Leu Glu
             20                  25                  30

Ser Ser

<210> SEQ ID NO 80
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 80

Asp Leu Gly Pro Pro Ile Ser Leu Glu Arg Leu Asp Val Gly Thr Asn
 1               5                  10                  15

Leu Gly Asn Ala Ile Ala Lys Leu Glu Ala Lys Glu Leu Leu Glu Ser
             20                  25                  30

Ser Asp

<210> SEQ ID NO 81
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 81

```
Leu Gly Pro Pro Ile Ser Leu Glu Arg Leu Asp Val Gly Thr Asn Leu
 1               5                  10                  15

Gly Asn Ala Ile Ala Lys Leu Glu Ala Lys Glu Leu Leu Glu Ser Ser
            20                  25                  30

Asp Gln

<210> SEQ ID NO 82
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 82

Gly Pro Pro Ile Ser Leu Glu Arg Leu Asp Val Gly Thr Asn Leu Gly
 1               5                  10                  15

Asn Ala Ile Ala Lys Leu Glu Ala Lys Glu Leu Leu Glu Ser Ser Asp
            20                  25                  30

Gln Ile

<210> SEQ ID NO 83
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 83

Pro Pro Ile Ser Leu Glu Arg Leu Asp Val Gly Thr Asn Leu Gly Asn
 1               5                  10                  15

Ala Ile Ala Lys Leu Glu Ala Lys Glu Leu Leu Glu Ser Ser Asp Gln
            20                  25                  30

Ile Leu

<210> SEQ ID NO 84
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 84

Pro Ile Ser Leu Glu Arg Leu Asp Val Gly Thr Asn Leu Gly Asn Ala
 1               5                  10                  15

Ile Ala Lys Leu Glu Ala Lys Glu Leu Leu Glu Ser Ser Asp Gln Ile
            20                  25                  30

Leu Arg

<210> SEQ ID NO 85
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 85

Ser Leu Glu Arg Leu Asp Val Gly Thr Asn Leu Gly Asn Ala Ile Ala
 1               5                  10                  15
```

Lys Leu Glu Ala Lys Glu Leu Leu Glu Ser Ser Asp Gln Ile Leu Arg
            20                  25                  30

Ser Met

<210> SEQ ID NO 86
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 86

Leu Glu Arg Leu Asp Val Gly Thr Asn Leu Gly Asn Ala Ile Ala Lys
1               5                   10                  15

Leu Glu Ala Lys Glu Leu Leu Glu Ser Ser Asp Gln Ile Leu Arg Ser
            20                  25                  30

Met Lys

<210> SEQ ID NO 87
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 87

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp
        35

<210> SEQ ID NO 88
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 88

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn

<210> SEQ ID NO 89
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 89

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu

-continued

```
              20                  25                  30

Trp

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 90

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 91

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 92

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala
            20                  25                  30

<210> SEQ ID NO 93
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 93

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp
            20                  25

<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: synthetic
``` peptide

<400> SEQUENCE: 94

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys
            20                  25

<210> SEQ ID NO 95
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 95

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp
            20                  25

<210> SEQ ID NO 96
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 96

Tyr Thr Ser Leu Ile His Ser Leu Ile Glu Glu Ser Gln Asn Gln Gln
1               5                   10                  15

Glu Lys Asn Glu Gln Glu Leu Leu Glu Leu
            20                  25

<210> SEQ ID NO 97
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 97

Tyr Thr Ser Leu Ile His Ser Leu Ile Glu Glu Ser Gln Asn Gln Gln
1               5                   10                  15

Glu Lys Asn Glu Gln Glu Leu Leu Glu
            20                  25

<210> SEQ ID NO 98
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 98

Tyr Thr Ser Leu Ile His Ser Leu Ile Glu Glu Ser Gln Asn Gln Gln
1               5                   10                  15

Glu Lys Asn Glu Gln Glu Leu Leu
            20

```
<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 99

Tyr Thr Ser Leu Ile His Ser Leu Ile Glu Glu Ser Gln Asn Gln Gln
 1               5                  10                  15

Glu Lys Asn Glu Gln Glu Leu
            20

<210> SEQ ID NO 100
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 100

Tyr Thr Ser Leu Ile His Ser Leu Ile Glu Glu Ser Gln Asn Gln Gln
 1               5                  10                  15

Glu Lys Asn Glu Gln Glu
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 101

Tyr Thr Ser Leu Ile His Ser Leu Ile Glu Glu Ser Gln Asn Gln Gln
 1               5                  10                  15

Glu Lys Asn Glu Gln
            20

<210> SEQ ID NO 102
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 102

Tyr Thr Ser Leu Ile His Ser Leu Ile Glu Glu Ser Gln Asn Gln Gln
 1               5                  10                  15

Glu Lys Asn Glu
            20

<210> SEQ ID NO 103
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 103

Tyr Thr Ser Leu Ile His Ser Leu Ile Glu Glu Ser Gln Asn Gln Gln
```

-continued

```
                 1               5                  10                 15
Glu Lys Asn

<210> SEQ ID NO 104
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 104

Tyr Thr Ser Leu Ile His Ser Leu Ile Glu Glu Ser Gln Asn Gln Gln
 1               5                  10                 15
Glu Lys

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 105

Tyr Thr Ser Leu Ile His Ser Leu Ile Glu Glu Ser Gln Asn Gln Gln
 1               5                  10                 15
Glu

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 106

Tyr Thr Ser Leu Ile His Ser Leu Ile Glu Glu Ser Gln Asn Gln Gln
 1               5                  10                 15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 107

Tyr Thr Ser Leu Ile His Ser Leu Ile Glu Glu Ser Gln Asn Gln
 1               5                  10                 15

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 108

Tyr Thr Ser Leu Ile His Ser Leu Ile Glu Glu Ser Gln Asn
 1               5                  10
```

```
<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 109

Tyr Thr Ser Leu Ile His Ser Leu Ile Glu Glu Ser Gln
 1               5                  10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 110

Tyr Thr Ser Leu Ile His Ser Leu Ile Glu Glu Ser
 1               5                  10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 111

Tyr Thr Ser Leu Ile His Ser Leu Ile Glu Glu
 1               5                  10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 112

Tyr Thr Ser Leu Ile His Ser Leu Ile Glu
 1               5                  10

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 113

Tyr Thr Ser Leu Ile His Ser Leu Ile
 1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 114
```

Tyr Thr Ser Leu Ile His Ser Leu
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 115

Tyr Thr Ser Leu Ile His Ser
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 116

Tyr Thr Ser Leu Ile His
1               5

<210> SEQ ID NO 117
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 117

Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 118

Ser Leu Ile His Ser Leu Ile Glu Glu Ser Gln Asn Gln Gln
1               5                   10

Glu Lys Asn Glu Gln Glu Leu Leu Glu Leu Asp Lys Trp Ala Ser Leu
15                  20                  25                  30

Trp Asn Trp Phe

<210> SEQ ID NO 119
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

```
<400> SEQUENCE: 119

Leu Ile His Ser Leu Ile Glu Glu Ser Gln Asn Gln Gln
 1               5                  10

Glu Lys Asn Glu Gln Glu Leu Leu Glu Leu Asp Lys Trp Ala Ser Leu
        15                  20                  25

Trp Asn Trp Phe
 30

<210> SEQ ID NO 120
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 120

Ile His Ser Leu Ile Glu Glu Ser Gln Asn Gln Gln
 1               5                  10

Glu Lys Asn Glu Gln Glu Leu Leu Glu Leu Asp Lys Trp Ala Ser Leu
        15                  20                  25

Trp Asn Trp Phe
    30

<210> SEQ ID NO 121
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 121

His Ser Leu Ile Glu Glu Ser Gln Asn Gln Gln
 1               5                  10

Glu Lys Asn Glu Gln Glu Leu Leu Glu Leu Asp Lys Trp Ala Ser Leu
            15                  20                  25

Trp Asn Trp Phe
        30

<210> SEQ ID NO 122
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 122

Ser Leu Ile Glu Glu Ser Gln Asn Gln Gln
 1               5                  10

Glu Lys Asn Glu Gln Glu Leu Leu Glu Leu Asp Lys Trp Ala Ser Leu
                15                  20                  25

Trp Asn Trp Phe
            30

<210> SEQ ID NO 123
<211> LENGTH: 29
<212> TYPE: PRT
<213> ORGANISM: Artificial Sequence
<220> FEATURE:
<223> OTHER INFORMATION: Description of Artificial Sequence: synthetic
``` peptide

<400> SEQUENCE: 123

Leu Ile Glu Glu Ser Gln Asn Gln Gln Glu Lys Asn Glu Gln Glu
 1               5                  10                  15

Leu Leu Glu Leu Asp Lys Trp Ala Ser Leu Trp Asn Trp Phe
            20                  25

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 124

Ile Glu Glu Ser Gln Asn Gln Gln Glu Lys Asn Glu Gln Glu
 1               5                  10

Leu Leu Glu Leu Asp Lys Trp Ala Ser Leu Trp Asn Trp Phe
15                  20                  25

<210> SEQ ID NO 125
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 125

Glu Glu Ser Gln Asn Gln Gln Glu Lys Asn Glu Gln Glu
 1               5                  10

Leu Leu Glu Leu Asp Lys Trp Ala Ser Leu Trp Asn Trp Phe
        15                  20                  25

<210> SEQ ID NO 126
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 126

Glu Ser Gln Asn Gln Gln Glu Lys Asn Glu Gln Glu
 1               5                  10

Leu Leu Glu Leu Asp Lys Trp Ala Ser Leu Trp Asn Trp Phe
            15                  20                  25

<210> SEQ ID NO 127
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 127

Ser Gln Asn Gln Gln Glu Lys Asn Glu Gln Glu
 1               5                  10

Leu Leu Glu Leu Asp Lys Trp Ala Ser Leu Trp Asn Trp Phe
                15                  20                  25

```
<210> SEQ ID NO 128
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 128

Gln Asn Gln Gln Glu Lys Asn Glu Gln Glu
  1               5                  10

Leu Leu Glu Leu Asp Lys Trp Ala Ser Leu Trp Asn Trp Phe
                 15                  20

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 129

Asn Gln Gln Glu Lys Asn Glu Gln Glu Leu Leu Glu Leu Asp Lys
  1               5                  10                  15

Trp Ala Ser Leu Trp Asn Trp Phe
                 20

<210> SEQ ID NO 130
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 130

Gln Gln Glu Lys Asn Glu Gln Glu Leu Leu Glu Leu Asp Lys Trp
  1               5                  10                  15

Ala Ser Leu Trp Asn Trp Phe
                 20

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 131

Gln Glu Lys Asn Glu Gln Glu Leu Leu Glu Leu Asp Lys Trp Ala
  1               5                  10                  15

Ser Leu Trp Asn Trp Phe
                 20

<210> SEQ ID NO 132
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 132

Glu Lys Asn Glu Gln Glu Leu Leu Glu Leu Asp Lys Trp Ala Ser
```

-continued

```
                1               5                  10                  15

Leu Trp Asn Trp Phe
                20

<210> SEQ ID NO 133
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 133

Lys Asn Glu Gln Glu Leu Leu Glu Leu Asp Lys Trp Ala Ser Leu
 1               5                  10                  15

Trp Asn Trp Phe

<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 134

Asn Glu Gln Glu Leu Leu Glu Leu Asp Lys Trp Ala Ser
 1               5                  10

Leu Trp Asn Trp Phe
      15

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 135

Glu Gln Glu Leu Leu Glu Leu Asp Lys Trp Ala Ser
 1               5                  10

Leu Trp Asn Trp Phe
        15

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 136

Gln Glu Leu Leu Glu Leu Asp Lys Trp Ala Ser Leu Trp Asn Trp Phe
 1               5                  10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 137
```

Glu Leu Leu Glu Leu Asp Lys Trp Ala Ser Leu Trp Asn Trp Phe
 1               5                   10                  15

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 138

Leu Leu Glu Leu Asp Lys Trp Ala Ser Leu Trp Asn Trp Phe
 1               5                   10

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 139

Leu Glu Leu Asp Lys Trp Ala Ser Leu Trp Asn Trp Phe
 1               5                   10

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 140

Glu Leu Asp Lys Trp Ala Ser Leu Trp Asn Trp Phe
 1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 141

Leu Asp Lys Trp Ala Ser Leu Trp Asn Trp Phe
 1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 142

Asp Lys Trp Ala Ser Leu Trp Asn Trp Phe
 1               5                   10

<210> SEQ ID NO 143
<211> LENGTH: 9
<212> TYPE: PRT
<213> ORGANISM: Artificial Sequence

```
<220> FEATURE:
<223> OTHER INFORMATION: Description of Artificial Sequence: synthetic
      peptide

<400> SEQUENCE: 143

Lys Trp Ala Ser Leu Trp Asn Trp Phe
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 144

Trp Ala Ser Leu Trp Asn Trp Phe
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 145

Ala Ser Leu Trp Asn Trp Phe
1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 146

Ser Leu Trp Asn Trp Phe
1               5

<210> SEQ ID NO 147
<211> LENGTH: 37
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 147

Asn Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
            20                  25                  30

Arg Tyr Leu Lys Asp
        35

<210> SEQ ID NO 148
<211> LENGTH: 36
<212> TYPE: PRT
<213> ORGANISM: Artificial Sequence
<220> FEATURE:
<223> OTHER INFORMATION: Description of Artificial Sequence: synthetic
      peptide
```

<400> SEQUENCE: 148

Asn Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
            20                  25                  30

Arg Tyr Leu Lys
        35

<210> SEQ ID NO 149
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 149

Asn Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
            20                  25                  30

Arg Tyr Leu
        35

<210> SEQ ID NO 150
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 150

Asn Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
            20                  25                  30

Arg Tyr

<210> SEQ ID NO 151
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 151

Asn Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
            20                  25                  30

Arg

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

```
<400> SEQUENCE: 152

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg Ile Leu Ala Val Glu
             20                  25                  30

<210> SEQ ID NO 153
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 153

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg Ile Leu Ala Val
             20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 154

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg Ile Leu Ala
             20                  25                  30

<210> SEQ ID NO 155
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 155

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg Ile Leu
             20                  25

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 156

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg Ile
             20                  25

<210> SEQ ID NO 157
<211> LENGTH: 27
```

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 157

Asn Asn Leu Leu Arg Ala Ile Glu Ala Gln Gln His Leu Leu Gln Leu
 1               5                  10                  15

Thr Val Trp Gln Ile Lys Gln Leu Gln Ala Arg
            20                  25

<210> SEQ ID NO 158
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 158

Asn Asn Leu Leu Arg Ala Ile Glu Ala Gln Gln His Leu Leu Gln Leu
 1               5                  10                  15

Thr Val Trp Gln Ile Lys Gln Leu Gln Ala
            20                  25

<210> SEQ ID NO 159
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 159

Asn Asn Leu Leu Arg Ala Ile Glu Ala Gln Gln His Leu Leu Gln Leu
 1               5                  10                  15

Thr Val Trp Gln Ile Lys Gln Leu Gln
            20                  25

<210> SEQ ID NO 160
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 160

Asn Asn Leu Leu Arg Ala Ile Glu Ala Gln Gln His Leu Leu Gln Leu
 1               5                  10                  15

Thr Val Trp Gln Ile Lys Gln Leu
            20

<210> SEQ ID NO 161
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 161

Asn Asn Leu Leu Arg Ala Ile Glu Ala Gln Gln His Leu Leu Gln Leu
 1               5                  10                  15
```

Thr Val Trp Gln Ile Lys Gln
            20

<210> SEQ ID NO 162
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 162

Asn Asn Leu Leu Arg Ala Ile Glu Ala Gln Gln His Leu Leu Gln Leu
 1               5                  10                  15

Thr Val Trp Gln Ile Lys
            20

<210> SEQ ID NO 163
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 163

Asn Asn Leu Leu Arg Ala Ile Glu Ala Gln Gln His Leu Leu Gln Leu
 1               5                  10                  15

Thr Val Trp Gln Ile
            20

<210> SEQ ID NO 164
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 164

Asn Asn Leu Leu Arg Ala Ile Glu Ala Gln Gln His Leu Leu Gln Leu
 1               5                  10                  15

Thr Val Trp Gln
            20

<210> SEQ ID NO 165
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 165

Asn Asn Leu Leu Arg Ala Ile Glu Ala Gln Gln His Leu Leu Gln Leu
 1               5                  10                  15

Thr Val Trp

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 166

Asn Asn Leu Leu Arg Ala Ile Glu Ala Gln Gln His Leu Leu Gln Leu
  1               5                  10                  15

Thr Val

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 167

Asn Asn Leu Leu Arg Ala Ile Glu Ala Gln Gln His Leu Leu Gln Leu
  1               5                  10                  15

Thr

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 168

Asn Asn Leu Leu Arg Ala Ile Glu Ala Gln Gln His Leu Leu Gln Leu
  1               5                  10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 169

Asn Asn Leu Leu Arg Ala Ile Glu Ala Gln Gln His Leu Leu Gln
  1               5                  10                  15

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 170

Asn Asn Leu Leu Arg Ala Ile Glu Ala Gln Gln His Leu Leu
  1               5                  10

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 171

Asn Asn Leu Leu Arg Ala Ile Glu Ala Gln Gln His Leu
  1               5                  10
```

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 172

Asn Asn Leu Leu Arg Ala Ile Glu Ala Gln Gln His
 1               5                  10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 173

Asn Asn Leu Leu Arg Ala Ile Glu Ala Gln Gln
 1               5                  10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 174

Asn Asn Leu Leu Arg Ala Ile Glu Ala Gln
 1               5                  10

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 175

Asn Asn Leu Leu Arg Ala Ile Glu Ala
 1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 176

Asn Asn Leu Leu Arg Ala Ile Glu
 1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 177

Asn Asn Leu Leu Arg Ala Ile
1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 178

Asn Asn Leu Leu Arg Ala
1               5

<210> SEQ ID NO 179
<211> LENGTH: 37
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 179

Asn Leu Leu Arg Ala Ile Glu Ala Gln Gln His Leu Leu Gln Leu
1               5                   10                  15

Thr Val Trp Gln Ile Lys Gln Leu Gln Ala Arg Ile Leu Ala Val Glu
                20                  25                  30

Arg Tyr Leu Lys Asp Gln
            35

<210> SEQ ID NO 180
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 180

Leu Leu Arg Ala Ile Glu Ala Gln Gln His Leu Leu Gln Leu Thr
1               5                   10                  15

Val Trp Gln Ile Lys Gln Leu Gln Ala Arg Ile Leu Ala Val Glu
                20                  25                  30

Arg Tyr Leu Lys Asp Gln
            35

<210> SEQ ID NO 181
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 181

Leu Arg Ala Ile Glu Ala Gln Gln His Leu Leu Gln Leu Thr Val
1               5                   10                  15

Trp Gln Ile Lys Gln Leu Gln Ala Arg Ile Leu Ala Val Glu Arg
                20                  25                  30

Tyr Leu Lys Asp Gln
            35
```

```
<210> SEQ ID NO 182
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 182

Arg Ala Ile Glu Ala Gln Gln His Leu Leu Gln Leu Thr Val Trp
  1               5                  10                  15

Gln Ile Lys Gln Leu Gln Ala Arg Ile Leu Ala Val Glu Arg Tyr
                 20                  25                  30

Leu Lys Asp Gln

<210> SEQ ID NO 183
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 183

Ala Ile Glu Ala Gln Gln His Leu Leu Gln Leu Thr Val Trp Gln
  1               5                  10                  15

Ile Lys Gln Leu Gln Ala Arg Ile Leu Ala Val Glu Arg Tyr Leu
                 20                  25                  30

Lys Asp Gln

<210> SEQ ID NO 184
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 184

Ile Glu Ala Gln Gln His Leu Leu Gln Leu Thr Val Trp Gln Ile
  1               5                  10                  15

Lys Gln Leu Gln Ala Arg Ile Leu Ala Val Glu Arg Tyr Leu Lys
                 20                  25                  30

Asp Gln

<210> SEQ ID NO 185
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 185

Glu Ala Gln Gln His Leu Leu Gln Leu Thr Val Trp Gln Ile Lys
  1               5                  10                  15

Gln Leu Gln Ala Arg Ile Leu Ala Val Glu Arg Tyr Leu Lys Asp
                 20                  25                  30

Gln

<210> SEQ ID NO 186
<211> LENGTH: 30
```

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 186

Ala Gln Gln His Leu Leu Gln Leu Thr Val Trp Gln Ile Lys Gln
 1               5                  10                  15

Leu Gln Ala Arg Ile Leu Ala Val Glu Arg Tyr Leu Lys Asp Gln
                20                  25                  30

<210> SEQ ID NO 187
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 187

Gln Gln His Leu Leu Gln Leu Thr Val Trp Gln Ile Lys Gln Leu
 1               5                  10                  15

Gln Ala Arg Ile Leu Ala Val Glu Arg Tyr Leu Lys Asp Gln
                20                  25

<210> SEQ ID NO 188
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 188

Gln His Leu Leu Gln Leu Thr Val Trp Gln Ile Lys Gln Leu Gln
 1               5                  10                  15

Ala Arg Ile Leu Ala Val Glu Arg Tyr Leu Lys Asp Gln
                20                  25

<210> SEQ ID NO 189
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 189

His Leu Leu Gln Leu Thr Val Trp Gln Ile Lys Gln Leu Gln Ala
 1               5                  10                  15

Arg Ile Leu Ala Val Glu Arg Tyr Leu Lys Asp Gln
                20                  25

<210> SEQ ID NO 190
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 190

Leu Leu Gln Leu Thr Val Trp Gln Ile Lys Gln Leu Gln Ala Arg
 1               5                  10                  15
```

-continued

Ile Leu Ala Val Glu Arg Tyr Leu Lys Asp Gln
            20                  25

<210> SEQ ID NO 191
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 191

Leu Gln Leu Thr Val Trp Gln Ile Lys Gln Leu Gln Ala Arg Ile
 1               5                  10                  15

Leu Ala Val Glu Arg Tyr Leu Lys Asp Gln
            20                  25

<210> SEQ ID NO 192
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 192

Gln Leu Thr Val Trp Gln Ile Lys Gln Leu Gln Ala Arg Ile Leu
 1               5                  10                  15

Ala Val Glu Arg Tyr Leu Lys Asp Gln
            20

<210> SEQ ID NO 193
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 193

Leu Thr Val Trp Gln Ile Lys Gln Leu Gln Ala Arg Ile Leu Ala
 1               5                  10                  15

Val Glu Arg Tyr Leu Lys Asp Gln
            20

<210> SEQ ID NO 194
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 194

Thr Val Trp Gln Ile Lys Gln Leu Gln Ala Arg Ile Leu Ala Val
 1               5                  10                  15

Glu Arg Tyr Leu Lys Asp Gln
            20

<210> SEQ ID NO 195
<211> LENGTH: 21
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 195

Val Trp Gln Ile Lys Gln Leu Gln Ala Arg Ile Leu Ala Val Glu
 1               5                  10                 15

Arg Tyr Leu Lys Asp Gln
            20

<210> SEQ ID NO 196
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 196

Trp Gln Ile Lys Gln Leu Gln Ala Arg Ile Leu Ala Val Glu Arg
 1               5                  10                 15

Tyr Leu Lys Asp Gln
            20

<210> SEQ ID NO 197
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 197

Gln Ile Lys Gln Leu Gln Ala Arg Ile Leu Ala Val Glu Arg Tyr
 1               5                  10                 15

Leu Lys Asp Gln

<210> SEQ ID NO 198
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 198

Ile Lys Gln Leu Gln Ala Arg Ile Leu Ala Val Glu Arg Tyr Leu
 1               5                  10                 15

Lys Asp Gln

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 199

Lys Gln Leu Gln Ala Arg Ile Leu Ala Val Glu Arg Tyr Leu Lys
 1               5                  10                 15

Asp Gln

<210> SEQ ID NO 200
<211> LENGTH: 16
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 200

Gln Leu Gln Ala Arg Ile Leu Ala Val Glu Arg Tyr Leu Lys Asp Gln
 1               5                  10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 201

Leu Gln Ala Arg Ile Leu Ala Val Glu Arg Tyr Leu Lys Asp Gln
 1               5                  10                  15

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 202

Gln Ala Arg Ile Leu Ala Val Glu Arg Tyr Leu Lys Asp Gln
 1               5                  10

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 203

Ala Arg Ile Leu Ala Val Glu Arg Tyr Leu Lys Asp Gln
 1               5                  10

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 204

Arg Ile Leu Ala Val Glu Arg Tyr Leu Lys Asp Gln
 1               5                  10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 205

Ile Leu Ala Val Glu Arg Tyr Leu Lys Asp Gln
 1               5                  10
```

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 206

Leu Ala Val Glu Arg Tyr Leu Lys Asp Gln
 1               5                  10

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 207

Ala Val Glu Arg Tyr Leu Lys Asp Gln
 1               5

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 208

Val Glu Arg Tyr Leu Lys Asp Gln
 1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 209

Glu Arg Tyr Leu Lys Asp Gln
 1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 210

Arg Tyr Leu Lys Asp Gln
 1               5

<210> SEQ ID NO 211
<211> LENGTH: 35
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 211

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp Asp Val Phe
            20                  25                  30

Thr Asn Trp
        35

<210> SEQ ID NO 212
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 212

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp Asp Val Phe
            20                  25                  30

Thr Asn

<210> SEQ ID NO 213
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 213

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp Asp Val Phe
            20                  25                  30

Thr

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 214

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp Asp Val Phe
            20                  25                  30

<210> SEQ ID NO 215
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 215

Leu Glu Ala Asn Ile Ser Gln Ser Leu Glu Gln Ala Gln Ile Gln Gln
 1               5                  10                  15
```

```
Glu Lys Asn Met Tyr Glu Leu Gln Lys Leu Asn Ser Trp Asp Val
            20                  25                  30

<210> SEQ ID NO 216
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 216

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp Asp
            20                  25                  30

<210> SEQ ID NO 217
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 217

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser Trp
            20                  25

<210> SEQ ID NO 218
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 218

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser
            20                  25

<210> SEQ ID NO 219
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 219

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn
            20                  25

<210> SEQ ID NO 220
<211> LENGTH: 26
<212> TYPE: PRT
<213> ORGANISM: Artificial Sequence
<220> FEATURE:
<223> OTHER INFORMATION: Description of Artificial Sequence: synthetic
``` peptide

<400> SEQUENCE: 220

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu
            20                  25

<210> SEQ ID NO 221
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 221

Leu Glu Ala Asn Ile Ser Gln Ser Leu Glu Gln Ala Gln Ile Gln Gln
1               5                   10                  15

Glu Lys Asn Met Tyr Glu Leu Gln Lys
            20                  25

<210> SEQ ID NO 222
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 222

Leu Glu Ala Asn Ile Ser Gln Ser Leu Glu Gln Ala Gln Ile Gln Gln
1               5                   10                  15

Glu Lys Asn Met Tyr Glu Leu Gln
            20

<210> SEQ ID NO 223
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 223

Leu Glu Ala Asn Ile Ser Gln Ser Leu Glu Gln Ala Gln Ile Gln Gln
1               5                   10                  15

Glu Lys Asn Met Tyr Glu Leu
            20

<210> SEQ ID NO 224
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 224

Leu Glu Ala Asn Ile Ser Gln Ser Leu Glu Gln Ala Gln Ile Gln Gln
1               5                   10                  15

Glu Lys Asn Met Tyr Glu
            20

```
<210> SEQ ID NO 225
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 225

Leu Glu Ala Asn Ile Ser Gln Ser Leu Glu Gln Ala Gln Ile Gln Gln
 1               5                  10                  15

Glu Lys Asn Met Tyr
            20

<210> SEQ ID NO 226
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 226

Leu Glu Ala Asn Ile Ser Gln Ser Leu Glu Gln Ala Gln Ile Gln Gln
 1               5                  10                  15

Glu Lys Asn Met
            20

<210> SEQ ID NO 227
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 227

Leu Glu Ala Asn Ile Ser Gln Ser Leu Glu Gln Ala Gln Ile Gln Gln
 1               5                  10                  15

Glu Lys Asn

<210> SEQ ID NO 228
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 228

Leu Glu Ala Asn Ile Ser Gln Ser Leu Glu Gln Ala Gln Ile Gln Gln
 1               5                  10                  15

Glu Lys

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 229

Leu Glu Ala Asn Ile Ser Gln Ser Leu Glu Gln Ala Gln Ile Gln Gln
 1               5                  10                  15
```

Glu

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 230

Leu Glu Ala Asn Ile Ser Gln Ser Leu Glu Gln Ala Gln Ile Gln Gln
 1               5                  10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 231

Leu Glu Ala Asn Ile Ser Gln Ser Leu Glu Gln Ala Gln Ile Gln
 1               5                  10                  15

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 232

Leu Glu Ala Asn Ile Ser Gln Ser Leu Glu Gln Ala Gln Ile
 1               5                  10

<210> SEQ ID NO 233
<211> LENGTH: 13
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 233

Leu Glu Ala Asn Ile Ser Gln Ser Leu Glu Gln Ala Gln
 1               5                  10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: synthetic
    peptide

<400> SEQUENCE: 234

Leu Glu Ala Asn Ile Ser Gln Ser Leu Glu Gln Ala
 1               5                  10

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: synthetic -continued peptide

<400> SEQUENCE: 235

Leu Glu Ala Asn Ile Ser Gln Ser Leu Glu Gln
 1               5                  10

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 236

Leu Glu Ala Asn Ile Ser Gln Ser Leu Glu
 1               5                  10

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 237

Leu Glu Ala Asn Ile Ser Gln Ser Leu
 1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 238

Leu Glu Ala Asn Ile Ser Gln Ser
 1               5

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 239

Leu Glu Ala Asn Ile Ser Gln
 1               5

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 240

Leu Glu Ala Asn Ile Ser
 1               5

<210> SEQ ID NO 241

<211> LENGTH: 35
<212> TYPE: PRT
<213> ORGANISM: Artificial Sequence
<220> FEATURE:
<223> OTHER INFORMATION: Description of Artificial Sequence: synthetic peptide

<400> SEQUENCE: 241

Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
                20                  25                  30

Thr Asn Trp Leu
            35

<210> SEQ ID NO 242
<211> LENGTH: 34
<212> TYPE: PRT
<213> ORGANISM: Artificial Sequence
<220> FEATURE:
<223> OTHER INFORMATION: Description of Artificial Sequence: synthetic peptide

<400> SEQUENCE: 242

Ala Asn Ile Ser Gln Ser Leu Glu Gln Ala Gln Ile Gln Gln Glu
1               5                   10                  15

Lys Asn Met Tyr Glu Leu Gln Lys Leu Asn Ser Trp Asp Val Phe
                20                  25                  30

Thr Asn Trp Leu

<210> SEQ ID NO 243
<211> LENGTH: 33
<212> TYPE: PRT
<213> ORGANISM: Artificial Sequence
<220> FEATURE:
<223> OTHER INFORMATION: Description of Artificial Sequence: synthetic peptide

<400> SEQUENCE: 243

Asn Ile Ser Gln Ser Leu Glu Gln Ala Gln Ile Gln Gln Glu Lys
1               5                   10                  15

Asn Met Tyr Glu Leu Gln Lys Leu Asn Ser Trp Asp Val Phe Thr
                20                  25                  30

Asn Trp Leu

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: synthetic peptide

<400> SEQUENCE: 244

Ile Ser Gln Ser Leu Glu Gln Ala Gln Ile Gln Gln Glu Lys Asn
1               5                   10                  15

Met Tyr Glu Leu Gln Lys Leu Asn Ser Trp Asp Val Phe Thr Asn
                20                  25                  30

Trp Leu

<210> SEQ ID NO 245
<211> LENGTH: 31
<212> TYPE: PRT

-continued

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: synthetic peptide

<400> SEQUENCE: 245

Ser Gln Ser Leu Glu Gln Ala Gln Ile Gln Gln Glu Lys Asn Met
1               5                   10                  15

Tyr Glu Leu Gln Lys Leu Asn Ser Trp Asp Val Phe Thr Asn Trp
                20                  25                  30

Leu

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: synthetic peptide

<400> SEQUENCE: 246

Gln Ser Leu Glu Gln Ala Gln Ile Gln Gln Glu Lys Asn Met Tyr
1               5                   10                  15

Glu Leu Gln Lys Leu Asn Ser Trp Asp Val Phe Thr Asn Trp Leu
                20                  25                  30

<210> SEQ ID NO 247
<211> LENGTH: 29
<212> TYPE: PRT
<213> ORGANISM: Artificial Sequence
<220> FEATURE:
<223> OTHER INFORMATION: Description of Artificial Sequence: synthetic peptide

<400> SEQUENCE: 247

Ser Leu Glu Gln Ala Gln Ile Gln Gln Glu Lys Asn Met Tyr Glu
1               5                   10                  15

Leu Gln Lys Leu Asn Ser Trp Asp Val Phe Thr Asn Trp Leu
                20                  25

<210> SEQ ID NO 248
<211> LENGTH: 28
<212> TYPE: PRT
<213> ORGANISM: Artificial Sequence
<220> FEATURE:
<223> OTHER INFORMATION: Description of Artificial Sequence: synthetic peptide

<400> SEQUENCE: 248

Leu Glu Gln Ala Gln Ile Gln Gln Glu Lys Asn Met Tyr Glu Leu
1               5                   10                  15

Gln Lys Leu Asn Ser Trp Asp Val Phe Thr Asn Trp Leu
                20                  25

<210> SEQ ID NO 249
<211> LENGTH: 27
<212> TYPE: PRT
<213> ORGANISM: Artificial Sequence
<220> FEATURE:
<223> OTHER INFORMATION: Description of Artificial Sequence: synthetic peptide

<400> SEQUENCE: 249

Glu Gln Ala Gln Ile Gln Gln Glu Lys Asn Met Tyr Glu Leu Gln
1               5                   10                  15

```
Lys Leu Asn Ser Trp Asp Val Phe Thr Asn Trp Leu
            20                  25

<210> SEQ ID NO 250
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 250

Gln Ala Gln Ile Gln Gln Glu Lys Asn Met Tyr Glu Leu Gln Lys
 1               5                  10                  15

Leu Asn Ser Trp Asp Val Phe Thr Asn Trp Leu
            20                  25

<210> SEQ ID NO 251
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 251

Ala Gln Ile Gln Gln Glu Lys Asn Met Tyr Glu Leu Gln Lys Leu
 1               5                  10                  15

Asn Ser Trp Asp Val Phe Thr Asn Trp Leu
            20                  25

<210> SEQ ID NO 252
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 252

Gln Ile Gln Gln Glu Lys Asn Met Tyr Glu Leu Gln Lys Leu Asn
 1               5                  10                  15

Ser Trp Asp Val Phe Thr Asn Trp Leu
            20

<210> SEQ ID NO 253
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 253

Ile Gln Gln Glu Lys Asn Met Tyr Glu Leu Gln Lys Leu Asn Ser
 1               5                  10                  15

Trp Asp Val Phe Thr Asn Trp Leu
            20

<210> SEQ ID NO 254
<211> LENGTH: 22
<212> TYPE: PRT
<213> ORGANISM: Artificial Sequence
<220> FEATURE:
<223> OTHER INFORMATION: Description of Artificial Sequence: synthetic
```

-continued peptide

<400> SEQUENCE: 254

Gln Gln Glu Lys Asn Met Tyr Glu Leu Gln Lys Leu Asn Ser Trp
 1               5                  10                  15

Asp Val Phe Thr Asn Trp Leu
                20

<210> SEQ ID NO 255
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 255

Gln Glu Lys Asn Met Tyr Glu Leu Gln Lys Leu Asn Ser Trp Asp
 1               5                  10                  15

Val Phe Thr Asn Trp Leu
                20

<210> SEQ ID NO 256
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 256

Glu Lys Asn Met Tyr Glu Leu Gln Lys Leu Asn Ser Trp Asp Val
 1               5                  10                  15

Phe Thr Asn Trp Leu
                20

<210> SEQ ID NO 257
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 257

Lys Asn Met Tyr Glu Leu Gln Lys Leu Asn Ser Trp Asp Val Phe
 1               5                  10                  15

Thr Asn Trp Leu

<210> SEQ ID NO 258
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 258

Asn Met Tyr Glu Leu Gln Lys Leu Asn Ser Trp Asp Val Phe Thr
 1               5                  10                  15

Asn Trp Leu

<210> SEQ ID NO 259
<211> LENGTH: 17

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 259

Met Tyr Glu Leu Gln Lys Leu Asn Ser Trp Asp Val Phe Thr Asn
1               5                   10                  15

Trp Leu

<210> SEQ ID NO 260
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 260

Tyr Glu Leu Gln Lys Leu Asn Ser Trp Asp Val Phe Thr Asn Trp Leu
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 261

Glu Leu Gln Lys Leu Asn Ser Trp Asp Val Phe Thr Asn Trp Leu
1               5                   10                  15

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 262

Leu Gln Lys Leu Asn Ser Trp Asp Val Phe Thr Asn Trp Leu
1               5                   10

<210> SEQ ID NO 263
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 263

Gln Lys Leu Asn Ser Trp Asp Val Phe Thr Asn Trp Leu
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 264
```

Lys Leu Asn Ser Trp Asp Val Phe Thr Asn Trp Leu
 1               5                  10

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 265

Leu Asn Ser Trp Asp Val Phe Thr Asn Trp Leu
 1               5                  10

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 266

Asn Ser Trp Asp Val Phe Thr Asn Trp Leu
 1               5                  10

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 267

Ser Trp Asp Val Phe Thr Asn Trp Leu
 1               5

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 268

Trp Asp Val Phe Thr Asn Trp Leu
 1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 269

Asp Val Phe Thr Asn Trp Leu
 1               5

<210> SEQ ID NO 270
<211> LENGTH: 6
<212> TYPE: PRT
<213> ORGANISM: Artificial Sequence

```
<220> FEATURE:
<223> OTHER INFORMATION: Description of Artificial Sequence: synthetic
      peptide

<400> SEQUENCE: 270

Val Phe Thr Asn Trp Leu
 1               5

<210> SEQ ID NO 271
<211> LENGTH: 47
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 271

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
             20                  25                  30

Lys Tyr Lys Asn Ala Val Thr Glu Leu Gln Leu Leu Met Gln Ser
         35                  40                  45

<210> SEQ ID NO 272
<211> LENGTH: 46
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 272

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
             20                  25                  30

Lys Tyr Lys Asn Ala Val Thr Glu Leu Gln Leu Leu Met Gln
         35                  40                  45

<210> SEQ ID NO 273
<211> LENGTH: 45
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 273

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
             20                  25                  30

Lys Tyr Lys Asn Ala Val Thr Glu Leu Gln Leu Leu Met
         35                  40                  45

<210> SEQ ID NO 274
<211> LENGTH: 44
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 274
```

Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys Asn Ala Val Thr Glu Leu Gln Leu Leu
        35                  40

<210> SEQ ID NO 275
<211> LENGTH: 43
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 275

Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys Asn Ala Val Thr Glu Leu Gln Leu
        35                  40

<210> SEQ ID NO 276
<211> LENGTH: 42
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 276

Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys Asn Ala Val Thr Glu Leu Gln
        35                  40

<210> SEQ ID NO 277
<211> LENGTH: 41
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 277

Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys Asn Ala Val Thr Glu Leu
        35                  40

<210> SEQ ID NO 278
<211> LENGTH: 40
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 278

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr Lys Asn Ala Val Thr Glu
        35                  40

<210> SEQ ID NO 279
<211> LENGTH: 39
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 279

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr Lys Asn Ala Val Thr
        35

<210> SEQ ID NO 280
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 280

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr Lys Asn Ala Val
        35

<210> SEQ ID NO 281
<211> LENGTH: 37
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 281

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr Lys Asn Ala
        35

<210> SEQ ID NO 282
<211> LENGTH: 36
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 282

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr Lys Asn
        35

<210> SEQ ID NO 283
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 283

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr Lys
        35

<210> SEQ ID NO 284
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 284

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys Tyr

<210> SEQ ID NO 285
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 285

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

Lys

<210> SEQ ID NO 286
<211> LENGTH: 32
<212> TYPE: PRT
<213> ORGANISM: Artificial Sequence
<220> FEATURE:
<223> OTHER INFORMATION: Description of Artificial Sequence: synthetic
      peptide
```

-continued

```
<400> SEQUENCE: 286

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu Asp
            20                  25                  30

<210> SEQ ID NO 287
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 287

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu Leu
            20                  25                  30

<210> SEQ ID NO 288
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 288

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln Glu
            20                  25                  30

<210> SEQ ID NO 289
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 289

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys Gln
            20                  25

<210> SEQ ID NO 290
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 290

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile Lys
            20                  25

<210> SEQ ID NO 291
<211> LENGTH: 27
```

<212> TYPE: PRT
<213> ORGANISM: Artificial Sequence
<220> FEATURE:
<223> OTHER INFORMATION: Description of Artificial Sequence: synthetic
      peptide

<400> SEQUENCE: 291

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu Ile
            20                  25

<210> SEQ ID NO 292
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 292

Tyr Thr Ser Val Ile Thr Ile Glu Leu Ser Asn Ile Lys Glu Asn Lys
 1               5                  10                  15

Cys Asn Gly Thr Asp Ala Lys Val Lys Leu
            20                  25

<210> SEQ ID NO 293
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 293

Tyr Thr Ser Val Ile Thr Ile Glu Leu Ser Asn Ile Lys Glu Asn Lys
 1               5                  10                  15

Cys Asn Gly Thr Asp Ala Lys Val Lys
            20                  25

<210> SEQ ID NO 294
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 294

Tyr Thr Ser Val Ile Thr Ile Glu Leu Ser Asn Ile Lys Glu Asn Lys
 1               5                  10                  15

Cys Asn Gly Thr Asp Ala Lys Val
            20

<210> SEQ ID NO 295
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 295

Tyr Thr Ser Val Ile Thr Ile Glu Leu Ser Asn Ile Lys Glu Asn Lys
 1               5                  10                  15

Cys Asn Gly Thr Asp Ala Lys
            20

<210> SEQ ID NO 296
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 296

Tyr Thr Ser Val Ile Thr Ile Glu Leu Ser Asn Ile Lys Glu Asn Lys
 1               5                  10                  15

Cys Asn Gly Thr Asp Ala
            20

<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 297

Tyr Thr Ser Val Ile Thr Ile Glu Leu Ser Asn Ile Lys Glu Asn Lys
 1               5                  10                  15

Cys Asn Gly Thr Asp
            20

<210> SEQ ID NO 298
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 298

Tyr Thr Ser Val Ile Thr Ile Glu Leu Ser Asn Ile Lys Glu Asn Lys
 1               5                  10                  15

Cys Asn Gly Thr
            20

<210> SEQ ID NO 299
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 299

Tyr Thr Ser Val Ile Thr Ile Glu Leu Ser Asn Ile Lys Glu Asn Lys
 1               5                  10                  15

Cys Asn Gly

<210> SEQ ID NO 300
<211> LENGTH: 18
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 300

Tyr Thr Ser Val Ile Thr Ile Glu Leu Ser Asn Ile Lys Glu Asn Lys
 1               5                  10                  15
Cys Asn

<210> SEQ ID NO 301
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 301

Tyr Thr Ser Val Ile Thr Ile Glu Leu Ser Asn Ile Lys Glu Asn Lys
 1               5                  10                  15
Cys

<210> SEQ ID NO 302
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 302

Tyr Thr Ser Val Ile Thr Ile Glu Leu Ser Asn Ile Lys Glu Asn Lys
 1               5                  10                  15

<210> SEQ ID NO 303
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 303

Tyr Thr Ser Val Ile Thr Ile Glu Leu Ser Asn Ile Lys Glu Asn
 1               5                  10                  15

<210> SEQ ID NO 304
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 304

Tyr Thr Ser Val Ile Thr Ile Glu Leu Ser Asn Ile Lys Glu
 1               5                  10

<210> SEQ ID NO 305
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 305

Tyr Thr Ser Val Ile Thr Ile Glu Leu Ser Asn Ile Lys
 1               5                  10
```

```
<210> SEQ ID NO 306
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 306

Tyr Thr Ser Val Ile Thr Ile Glu Leu Ser Asn Ile
 1               5                  10

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 307

Tyr Thr Ser Val Ile Thr Ile Glu Leu Ser Asn
 1               5                  10

<210> SEQ ID NO 308
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 308

Tyr Thr Ser Val Ile Thr Ile Glu Leu Ser
 1               5                  10

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 309

Tyr Thr Ser Val Ile Thr Ile Glu Leu
 1               5

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 310

Tyr Thr Ser Val Ile Thr Ile Glu
 1               5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 311

Tyr Thr Ser Val Ile Thr Ile
  1               5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 312

Tyr Thr Ser Val Ile Thr
  1               5

<210> SEQ ID NO 313
<211> LENGTH: 47
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 313

Thr Ser Val Ile Thr Ile Glu Leu Ser Asn Ile Lys Glu Asn Lys
  1               5                  10                  15

Cys Asn Gly Thr Asp Ala Lys Val Lys Leu Ile Lys Gln Glu Leu Asp
                 20                  25                  30

Lys Tyr Lys Asn Ala Val Thr Glu Leu Gln Leu Leu Met Gln Ser Thr
             35                  40                  45

<210> SEQ ID NO 314
<211> LENGTH: 46
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 314

Ser Val Ile Thr Ile Glu Leu Ser Asn Ile Lys Glu Asn Lys Cys
  1               5                  10                  15

Asn Gly Thr Asp Ala Lys Val Lys Leu Ile Lys Gln Glu Leu Asp
                 20                  25                  30

Lys Tyr Lys Asn Ala Val Thr Glu Leu Gln Leu Leu Met Gln Ser Thr
             35                  40                  45

<210> SEQ ID NO 315
<211> LENGTH: 45
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 315

Val Ile Thr Ile Glu Leu Ser Asn Ile Lys Glu Asn Lys Cys Asn
  1               5                  10                  15

Gly Thr Asp Ala Lys Val Lys Leu Ile Lys Gln Glu Leu Asp Lys
                 20                  25                  30

Tyr Lys Asn Ala Val Thr Glu Leu Gln Leu Leu Met Gln Ser Thr
             35                  40                  45
```

-continued

<210> SEQ ID NO 316
<211> LENGTH: 44
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 316

Ile Thr Ile Glu Leu Ser Asn Ile Lys Glu Asn Lys Cys Asn Gly
 1               5                  10                  15

Thr Asp Ala Lys Val Lys Leu Ile Lys Gln Glu Leu Asp Lys Tyr
                20                  25                  30

Lys Asn Ala Val Thr Glu Leu Gln Leu Leu Met Gln Ser Thr
                35                  40

<210> SEQ ID NO 317
<211> LENGTH: 43
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 317

Thr Ile Glu Leu Ser Asn Ile Lys Glu Asn Lys Cys Asn Gly Thr
 1               5                  10                  15

Asp Ala Lys Val Lys Leu Ile Lys Gln Glu Leu Asp Lys Tyr Lys
                20                  25                  30

Asn Ala Val Thr Glu Leu Gln Leu Leu Met Gln Ser Thr
                35                  40

<210> SEQ ID NO 318
<211> LENGTH: 42
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 318

Ile Glu Leu Ser Asn Ile Lys Glu Asn Lys Cys Asn Gly Thr Asp
 1               5                  10                  15

Ala Lys Val Lys Leu Ile Lys Gln Glu Leu Asp Lys Tyr Lys Asn
                20                  25                  30

Ala Val Thr Glu Leu Gln Leu Leu Met Gln Ser Thr
                35                  40

<210> SEQ ID NO 319
<211> LENGTH: 41
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 319

Glu Leu Ser Asn Ile Lys Glu Asn Lys Cys Asn Gly Thr Asp Ala
 1               5                  10                  15

Lys Val Lys Leu Ile Lys Gln Glu Leu Asp Lys Tyr Lys Asn Ala
                20                  25                  30

Val Thr Glu Leu Gln Leu Leu Met Gln Ser Thr
                35                  40

<210> SEQ ID NO 320
<211> LENGTH: 40
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 320

Leu Ser Asn Ile Lys Glu Asn Lys Cys Asn Gly Thr Asp Ala Lys
 1               5                  10                  15

Val Lys Leu Ile Lys Gln Glu Leu Asp Lys Tyr Lys Asn Ala Val
                20                  25                  30

Thr Glu Leu Gln Leu Leu Met Gln Ser Thr
                35                  40

<210> SEQ ID NO 321
<211> LENGTH: 39
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 321

Ser Asn Ile Lys Glu Asn Lys Cys Asn Gly Thr Asp Ala Lys Val
 1               5                  10                  15

Lys Leu Ile Lys Gln Glu Leu Asp Lys Tyr Lys Asn Ala Val Thr
                20                  25                  30

Glu Leu Gln Leu Leu Met Gln Ser Thr
                35

<210> SEQ ID NO 322
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 322

Asn Ile Lys Glu Asn Lys Cys Asn Gly Thr Asp Ala Lys Val Lys
 1               5                  10                  15

Leu Ile Lys Gln Glu Leu Asp Lys Tyr Lys Asn Ala Val Thr Glu
                20                  25                  30

Leu Gln Leu Leu Met Gln Ser Thr
                35

<210> SEQ ID NO 323
<211> LENGTH: 37
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 323

Ile Lys Glu Asn Lys Cys Asn Gly Thr Asp Ala Lys Val Lys Leu
 1               5                  10                  15

Ile Lys Gln Glu Leu Asp Lys Tyr Lys Asn Ala Val Thr Glu Leu
                20                  25                  30

Gln Leu Leu Met Gln Ser Thr

<210> SEQ ID NO 324
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 324

Lys Glu Asn Lys Cys Asn Gly Thr Asp Ala Lys Val Lys Leu Ile
 1               5                  10                  15

Lys Gln Glu Leu Asp Lys Tyr Lys Asn Ala Val Thr Glu Leu Gln
                20                  25                  30

Leu Leu Met Gln Ser Thr
                35

<210> SEQ ID NO 325
<211> LENGTH: 34
<212> TYPE: PRT
<213> ORGANISM: Artificial Sequence
<220> FEATURE:
<223> OTHER INFORMATION: Description of Artificial Sequence: synthetic peptide

<400> SEQUENCE: 325

Asn Lys Cys Asn Gly Thr Asp Ala Lys Val Lys Leu Ile Lys Gln
 1               5                  10                  15

Glu Leu Asp Lys Tyr Lys Asn Ala Val Thr Glu Leu Gln Leu Leu
                20                  25                  30

Met Gln Ser Thr

<210> SEQ ID NO 326
<211> LENGTH: 33
<212> TYPE: PRT
<213> ORGANISM: Artificial Sequence
<220> FEATURE:
<223> OTHER INFORMATION: Description of Artificial Sequence: synthetic peptide

<400> SEQUENCE: 326

Lys Cys Asn Gly Thr Asp Ala Lys Val Lys Leu Ile Lys Gln Glu
 1               5                  10                  15

Leu Asp Lys Tyr Lys Asn Ala Val Thr Glu Leu Gln Leu Leu Met
                20                  25                  30

Gln Ser Thr

<210> SEQ ID NO 327
<211> LENGTH: 32
<212> TYPE: PRT
<213> ORGANISM: Artificial Sequence
<220> FEATURE:
<223> OTHER INFORMATION: Description of Artificial Sequence: synthetic peptide

<400> SEQUENCE: 327

Cys Asn Gly Thr Asp Ala Lys Val Lys Leu Ile Lys Gln Glu Leu
 1               5                  10                  15

Asp Lys Tyr Lys Asn Ala Val Thr Glu Leu Gln Leu Leu Met Gln
                20                  25                  30

Ser Thr

<210> SEQ ID NO 328
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 328

Asn Gly Thr Asp Ala Lys Val Lys Leu Ile Lys Gln Glu Leu Asp
 1               5                  10                  15

Lys Tyr Lys Asn Ala Val Thr Glu Leu Gln Leu Leu Met Gln Ser
                20                  25                  30

Thr

<210> SEQ ID NO 329
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 329

Gly Thr Asp Ala Lys Val Lys Leu Ile Lys Gln Glu Leu Asp Lys
 1               5                  10                  15

Tyr Lys Asn Ala Val Thr Glu Leu Gln Leu Leu Met Gln Ser Thr
                20                  25                  30

<210> SEQ ID NO 330
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 330

Thr Asp Ala Lys Val Lys Leu Ile Lys Gln Glu Leu Asp Lys Tyr
 1               5                  10                  15

Lys Asn Ala Val Thr Glu Leu Gln Leu Leu Met Gln Ser Thr
                20                  25

<210> SEQ ID NO 331
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 331

Asp Ala Lys Val Lys Leu Ile Lys Gln Glu Leu Asp Lys Tyr Lys
 1               5                  10                  15

Asn Ala Val Thr Glu Leu Gln Leu Leu Met Gln Ser Thr
                20                  25

<210> SEQ ID NO 332
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

```
<400> SEQUENCE: 332

Ala Lys Val Lys Leu Ile Lys Gln Glu Leu Asp Lys Tyr Lys Asn
 1               5                  10                  15
Ala Val Thr Glu Leu Gln Leu Leu Met Gln Ser Thr
                20                  25

<210> SEQ ID NO 333
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 333

Lys Val Lys Leu Ile Lys Gln Glu Leu Asp Lys Tyr Lys Asn Ala
 1               5                  10                  15
Val Thr Glu Leu Gln Leu Leu Met Gln Ser Thr
                20                  25

<210> SEQ ID NO 334
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 334

Val Lys Leu Ile Lys Gln Glu Leu Asp Lys Tyr Lys Asn Ala Val
 1               5                  10                  15
Thr Glu Leu Gln Leu Leu Met Gln Ser Thr
                20                  25

<210> SEQ ID NO 335
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 335

Lys Leu Ile Lys Gln Glu Leu Asp Lys Tyr Lys Asn Ala Val Thr
 1               5                  10                  15
Glu Leu Gln Leu Leu Met Gln Ser Thr
                20

<210> SEQ ID NO 336
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 336

Leu Ile Lys Gln Glu Leu Asp Lys Tyr Lys Asn Ala Val Thr Glu
 1               5                  10                  15
Leu Gln Leu Leu Met Gln Ser Thr
                20

<210> SEQ ID NO 337
<211> LENGTH: 22
```

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 337

Ile Lys Gln Glu Leu Asp Lys Tyr Lys Asn Ala Val Thr Glu Leu
 1               5                  10                  15

Gln Leu Leu Met Gln Ser Thr
                20

<210> SEQ ID NO 338
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 338

Lys Gln Glu Leu Asp Lys Tyr Lys Asn Ala Val Thr Glu Leu Gln
 1               5                  10                  15

Leu Leu Met Gln Ser Thr
                20

<210> SEQ ID NO 339
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 339

Gln Glu Leu Asp Lys Tyr Lys Asn Ala Val Thr Glu Leu Gln Leu
 1               5                  10                  15

Leu Met Gln Ser Thr
                20

<210> SEQ ID NO 340
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 340

Glu Leu Asp Lys Tyr Lys Asn Ala Val Thr Glu Leu Gln Leu Leu
 1               5                  10                  15

Met Gln Ser Thr

<210> SEQ ID NO 341
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 341

Leu Asp Lys Tyr Lys Asn Ala Val Thr Glu Leu Gln Leu Leu Met
 1               5                  10                  15

Gln Ser Thr
```

```
<210> SEQ ID NO 342
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 342

Asp Lys Tyr Lys Asn Ala Val Thr Glu Leu Gln Leu Leu Met Gln
 1               5                  10                  15

Ser Thr

<210> SEQ ID NO 343
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 343

Lys Tyr Lys Asn Ala Val Thr Glu Leu Gln Leu Leu Met Gln Ser Thr
 1               5                  10                  15

<210> SEQ ID NO 344
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 344

Tyr Lys Asn Ala Val Thr Glu Leu Gln Leu Leu Met Gln Ser Thr
 1               5                  10                  15

<210> SEQ ID NO 345
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 345

Lys Asn Ala Val Thr Glu Leu Gln Leu Leu Met Gln Ser Thr
 1               5                  10

<210> SEQ ID NO 346
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 346

Asn Ala Val Thr Glu Leu Gln Leu Leu Met Gln Ser Thr
 1               5                  10

<210> SEQ ID NO 347
<211> LENGTH: 12
<212> TYPE: PRT
<213> ORGANISM: Artificial Sequence
<220> FEATURE:
```

```
<223> OTHER INFORMATION: Description of Artificial Sequence: synthetic
      peptide

<400> SEQUENCE: 347

Ala Val Thr Glu Leu Gln Leu Leu Met Gln Ser Thr
 1               5                  10

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 348

Val Thr Glu Leu Gln Leu Leu Met Gln Ser Thr
 1               5                  10

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 349

Thr Glu Leu Gln Leu Leu Met Gln Ser Thr
 1               5                  10

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 350

Glu Leu Gln Leu Leu Met Gln Ser Thr
 1               5

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 351

Leu Gln Leu Leu Met Gln Ser Thr
 1               5

<210> SEQ ID NO 352
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 352

Gln Leu Leu Met Gln Ser Thr
 1               5
```

```
<210> SEQ ID NO 353
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 353

Leu Leu Met Gln Ser Thr
 1               5

<210> SEQ ID NO 354
<211> LENGTH: 37
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 354

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg Lys Ser Asp Glu Leu Leu
                35

<210> SEQ ID NO 355
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 355

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg Lys Ser Asp Glu Leu
                35

<210> SEQ ID NO 356
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 356

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg Lys Ser Asp Glu
                35

<210> SEQ ID NO 357
<211> LENGTH: 34
<212> TYPE: PRT
<213> ORGANISM: Artificial Sequence
<220> FEATURE:
```

<223> OTHER INFORMATION: Description of Artificial Sequence: synthetic
      peptide

<400> SEQUENCE: 357

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg Lys Ser Asp

<210> SEQ ID NO 358
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 358

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg Lys Ser

<210> SEQ ID NO 359
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 359

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg Lys

<210> SEQ ID NO 360
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 360

Phe Tyr Asp Pro Leu Val Phe Pro Ser Asp Glu Phe Asp Ala Ser
 1               5                  10                  15

Ile Ser Gln Val Asn Glu Lys Ile Asn Gln Ser Leu Ala Phe Ile
                20                  25                  30

Arg

<210> SEQ ID NO 361
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 361

Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala Phe Ile
                20                  25                  30

<210> SEQ ID NO 362
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 362

Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala Phe
                20                  25

<210> SEQ ID NO 363
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 363

Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu Ala
                20                  25

<210> SEQ ID NO 364
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 364

Phe Tyr Asp Pro Leu Val Phe Pro Ser Asp Glu Phe Asp Ala Ser
1               5                   10                  15

Ile Ser Gln Val Asn Glu Lys Ile Asn Gln Ser Leu
                20                  25

<210> SEQ ID NO 365
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 365

Phe Tyr Asp Pro Leu Val Phe Pro Ser Asp Glu Phe Asp Ala Ser
1               5                   10                  15

Ile Ser Gln Val Asn Glu Lys Ile Asn Gln Ser
                20                  25

<210> SEQ ID NO 366
<211> LENGTH: 25

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 366

Phe Tyr Asp Pro Leu Val Phe Pro Ser Asp Glu Phe Asp Ala Ser
 1               5                  10                  15

Ile Ser Gln Val Asn Glu Lys Ile Asn Gln
                20                  25

<210> SEQ ID NO 367
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 367

Phe Tyr Asp Pro Leu Val Phe Pro Ser Asp Glu Phe Asp Ala Ser
 1               5                  10                  15

Ile Ser Gln Val Asn Glu Lys Ile Asn
                20

<210> SEQ ID NO 368
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 368

Phe Tyr Asp Pro Leu Val Phe Pro Ser Asp Glu Phe Asp Ala Ser
 1               5                  10                  15

Ile Ser Gln Val Asn Glu Lys Ile
                20

<210> SEQ ID NO 369
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 369

Phe Tyr Asp Pro Leu Val Phe Pro Ser Asp Glu Phe Asp Ala Ser
 1               5                  10                  15

Ile Ser Gln Val Asn Glu Lys
                20

<210> SEQ ID NO 370
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 370

Phe Tyr Asp Pro Leu Val Phe Pro Ser Asp Glu Phe Asp Ala Ser
 1               5                  10                  15
```

Ile Ser Gln Val Asn Glu
            20

<210> SEQ ID NO 371
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 371

Phe Tyr Asp Pro Leu Val Phe Pro Ser Asp Glu Phe Asp Ala Ser
 1               5                  10                  15

Ile Ser Gln Val Asn
            20

<210> SEQ ID NO 372
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 372

Phe Tyr Asp Pro Leu Val Phe Pro Ser Asp Glu Phe Asp Ala Ser
 1               5                  10                  15

Ile Ser Gln Val

<210> SEQ ID NO 373
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 373

Phe Tyr Asp Pro Leu Val Phe Pro Ser Asp Glu Phe Asp Ala Ser
 1               5                  10                  15

Ile Ser Gln

<210> SEQ ID NO 374
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 374

Phe Tyr Asp Pro Leu Val Phe Pro Ser Asp Glu Phe Asp Ala Ser
 1               5                  10                  15

Ile Ser

<210> SEQ ID NO 375
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 375

-continued

Phe Tyr Asp Pro Leu Val Phe Pro Ser Asp Glu Phe Asp Ala Ser
1               5                   10                  15

Ile

<210> SEQ ID NO 376
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 376

Phe Tyr Asp Pro Leu Val Phe Pro Ser Asp Glu Phe Asp Ala Ser
1               5                   10                  15

<210> SEQ ID NO 377
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 377

Phe Tyr Asp Pro Leu Val Phe Pro Ser Asp Glu Phe Asp Ala
1               5                   10

<210> SEQ ID NO 378
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 378

Phe Tyr Asp Pro Leu Val Phe Pro Ser Asp Glu Phe Asp
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 379

Phe Tyr Asp Pro Leu Val Phe Pro Ser Asp Glu Phe
1               5                   10

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 380

Phe Tyr Asp Pro Leu Val Phe Pro Ser Asp Glu
1               5                   10

<210> SEQ ID NO 381
<211> LENGTH: 10
<212> TYPE: PRT

```
<213> ORGANISM: Artificial Sequence
<220> FEATURE:
<223> OTHER INFORMATION: Description of Artificial Sequence: synthetic
      peptide

<400> SEQUENCE: 381

Phe Tyr Asp Pro Leu Val Phe Pro Ser Asp
 1               5                  10

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 382

Phe Tyr Asp Pro Leu Val Phe Pro Ser
 1               5

<210> SEQ ID NO 383
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 383

Phe Tyr Asp Pro Leu Val Phe Pro
 1               5

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 384

Phe Tyr Asp Pro Leu Val Phe
 1               5

<210> SEQ ID NO 385
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 385

Phe Tyr Asp Pro Leu Val
 1               5

<210> SEQ ID NO 386
<211> LENGTH: 36
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 386

Tyr Asp Pro Leu Val Phe Pro Ser Asp Glu Phe Asp Ala Ser Ile
 1               5                  10                  15
```

-continued

```
Ser Gln Val Asn Glu Lys Ile Asn Gln Ser Leu Ala Phe Ile Arg
            20                  25                  30

Lys Ser Asp Glu Leu Leu
            35

<210> SEQ ID NO 387
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 387

Asp Pro Leu Val Phe Pro Ser Asp Glu Phe Asp Ala Ser Ile Ser
 1               5                  10                  15

Gln Val Asn Glu Lys Ile Asn Gln Ser Leu Ala Phe Ile Arg Lys
            20                  25                  30

Ser Asp Glu Leu Leu
            35

<210> SEQ ID NO 388
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 388

Pro Leu Val Phe Pro Ser Asp Glu Phe Asp Ala Ser Ile Ser Gln
 1               5                  10                  15

Val Asn Glu Lys Ile Asn Gln Ser Leu Ala Phe Ile Arg Lys Ser
            20                  25                  30

Asp Glu Leu Leu

<210> SEQ ID NO 389
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 389

Leu Val Phe Pro Ser Asp Glu Phe Asp Ala Ser Ile Ser Gln Val
 1               5                  10                  15

Asn Glu Lys Ile Asn Gln Ser Leu Ala Phe Ile Arg Lys Ser Asp
            20                  25                  30

Glu Leu Leu

<210> SEQ ID NO 390
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 390

Val Phe Pro Ser Asp Glu Phe Asp Ala Ser Ile Ser Gln Val Asn
 1               5                  10                  15
```

-continued

Glu Lys Ile Asn Gln Ser Leu Ala Phe Ile Arg Lys Ser Asp Glu
            20                  25                  30

Leu Leu

<210> SEQ ID NO 391
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 391

Phe Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
            20                  25                  30

<210> SEQ ID NO 392
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 392

Pro Ser Asp Glu Phe Asp Ala Ser Ile Ser Gln Val Asn Glu Lys
 1               5                  10                  15

Ile Asn Gln Ser Leu Ala Phe Ile Arg Lys Ser Asp Glu Leu Leu
            20                  25                  30

<210> SEQ ID NO 393
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 393

Ser Asp Glu Phe Asp Ala Ser Ile Ser Gln Val Asn Glu Lys Ile
 1               5                  10                  15

Asn Gln Ser Leu Ala Phe Ile Arg Lys Ser Asp Glu Leu Leu
            20                  25

<210> SEQ ID NO 394
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 394

Asp Glu Phe Asp Ala Ser Ile Ser Gln Val Asn Glu Lys Ile Asn
 1               5                  10                  15

Gln Ser Leu Ala Phe Ile Arg Lys Ser Asp Glu Leu Leu
            20                  25

<210> SEQ ID NO 395
<211> LENGTH: 27
<212> TYPE: PRT
<213> ORGANISM: Artificial Sequence
<220> FEATURE:

<223> OTHER INFORMATION: Description of Artificial Sequence: synthetic
      peptide

<400> SEQUENCE: 395

Glu Phe Asp Ala Ser Ile Ser Gln Val Asn Glu Lys Ile Asn Gln
 1               5                  10                  15

Ser Leu Ala Phe Ile Arg Lys Ser Asp Glu Leu Leu
                20                  25

<210> SEQ ID NO 396
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 396

Phe Asp Ala Ser Ile Ser Gln Val Asn Glu Lys Ile Asn Gln Ser
 1               5                  10                  15

Leu Ala Phe Ile Arg Lys Ser Asp Glu Leu Leu
                20                  25

<210> SEQ ID NO 397
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 397

Asp Ala Ser Ile Ser Gln Val Asn Glu Lys Ile Asn Gln Ser Leu
 1               5                  10                  15

Ala Phe Ile Arg Lys Ser Asp Glu Leu Leu
                20                  25

<210> SEQ ID NO 398
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 398

Ala Ser Ile Ser Gln Val Asn Glu Lys Ile Asn Gln Ser Leu Ala
 1               5                  10                  15

Phe Ile Arg Lys Ser Asp Glu Leu Leu
                20

<210> SEQ ID NO 399
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 399

Ser Ile Ser Gln Val Asn Glu Lys Ile Asn Gln Ser Leu Ala Phe
 1               5                  10                  15

Ile Arg Lys Ser Asp Glu Leu Leu
                20

```
<210> SEQ ID NO 400
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 400

Ile Ser Gln Val Asn Glu Lys Ile Asn Gln Ser Leu Ala Phe Ile
 1               5                  10                  15
Arg Lys Ser Asp Glu Leu Leu
            20

<210> SEQ ID NO 401
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 401

Ser Gln Val Asn Glu Lys Ile Asn Gln Ser Leu Ala Phe Ile Arg
 1               5                  10                  15
Lys Ser Asp Glu Leu Leu
            20

<210> SEQ ID NO 402
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 402

Gln Val Asn Glu Lys Ile Asn Gln Ser Leu Ala Phe Ile Arg Lys
 1               5                  10                  15
Ser Asp Glu Leu Leu
            20

<210> SEQ ID NO 403
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 403

Val Asn Glu Lys Ile Asn Gln Ser Leu Ala Phe Ile Arg Lys Ser
 1               5                  10                  15
Asp Glu Leu Leu

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 404

Asn Glu Lys Ile Asn Gln Ser Leu Ala Phe Ile Arg Lys Ser Asp
```

-continued

```
                1               5                  10                  15
Glu Leu Leu

<210> SEQ ID NO 405
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 405

Glu Lys Ile Asn Gln Ser Leu Ala Phe Ile Arg Lys Ser Asp Glu
  1               5                  10                  15

Leu Leu

<210> SEQ ID NO 406
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 406

Lys Ile Asn Gln Ser Leu Ala Phe Ile Arg Lys Ser Asp Glu Leu Leu
  1               5                  10                  15

<210> SEQ ID NO 407
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 407

Ile Asn Gln Ser Leu Ala Phe Ile Arg Lys Ser Asp Glu Leu Leu
  1               5                  10                  15

<210> SEQ ID NO 408
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 408

Asn Gln Ser Leu Ala Phe Ile Arg Lys Ser Asp Glu Leu Leu
  1               5                  10

<210> SEQ ID NO 409
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 409

Gln Ser Leu Ala Phe Ile Arg Lys Ser Asp Glu Leu Leu
  1               5                  10

<210> SEQ ID NO 410
<211> LENGTH: 12
```

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 410

Ser Leu Ala Phe Ile Arg Lys Ser Asp Glu Leu Leu
 1               5                  10

<210> SEQ ID NO 411
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 411

Leu Ala Phe Ile Arg Lys Ser Asp Glu Leu Leu
 1               5                  10

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 412

Ala Phe Ile Arg Lys Ser Asp Glu Leu Leu
 1               5                  10

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 413

Phe Ile Arg Lys Ser Asp Glu Leu Leu
 1               5

<210> SEQ ID NO 414
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 414

Ile Arg Lys Ser Asp Glu Leu Leu
 1               5

<210> SEQ ID NO 415
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 415

Arg Lys Ser Asp Glu Leu Leu
```

```
                                1               5

<210> SEQ ID NO 416
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 416

Lys Ser Asp Glu Leu Leu
 1               5

<210> SEQ ID NO 417
<211> LENGTH: 35
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 417

Ile Thr Leu Asn Asn Ser Val Ala Leu Asp Pro Ile Asp Ile Ser
 1               5                   10                  15

Ile Glu Leu Asn Lys Ala Lys Ser Asp Leu Glu Glu Ser Lys Glu
                20                  25                  30

Trp Ile Arg Arg Ser
                35

<210> SEQ ID NO 418
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 418

Ile Thr Leu Asn Asn Ser Val Ala Leu Asp Pro Ile Asp Ile Ser
 1               5                   10                  15

Ile Glu Leu Asn Lys Ala Lys Ser Asp Leu Glu Glu Ser Lys Glu
                20                  25                  30

Trp Ile Arg Arg

<210> SEQ ID NO 419
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 419

Ile Thr Leu Asn Asn Ser Val Ala Leu Asp Pro Ile Asp Ile Ser
 1               5                   10                  15

Ile Glu Leu Asn Lys Ala Lys Ser Asp Leu Glu Glu Ser Lys Glu
                20                  25                  30

Trp Ile Arg

<210> SEQ ID NO 420
<211> LENGTH: 32
<212> TYPE: PRT
<213> ORGANISM: Artificial Sequence
```

-continued

```
<220> FEATURE:
<223> OTHER INFORMATION: Description of Artificial Sequence: synthetic
      peptide

<400> SEQUENCE: 420

Ile Thr Leu Asn Asn Ser Val Ala Leu Asp Pro Ile Asp Ile Ser
 1               5                  10                  15

Ile Glu Leu Asn Lys Ala Lys Ser Asp Leu Glu Glu Ser Lys Glu
                20                  25                  30

Trp Ile

<210> SEQ ID NO 421
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 421

Ile Thr Leu Asn Asn Ser Val Ala Leu Asp Pro Ile Asp Ile Ser
 1               5                  10                  15

Ile Glu Leu Asn Lys Ala Lys Ser Asp Leu Glu Glu Ser Lys Glu
                20                  25                  30

Trp

<210> SEQ ID NO 422
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 422

Ile Thr Leu Asn Asn Ser Val Ala Leu Asp Pro Ile Asp Ile Ser
 1               5                  10                  15

Ile Glu Leu Asn Lys Ala Lys Ser Asp Leu Glu Glu Ser Lys Glu
                20                  25                  30

<210> SEQ ID NO 423
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 423

Ile Thr Leu Asn Asn Ser Val Ala Leu Asp Pro Ile Asp Ile Ser
 1               5                  10                  15

Ile Glu Leu Asn Lys Ala Lys Ser Asp Leu Glu Glu Ser Lys
                20                  25

<210> SEQ ID NO 424
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 424

Ile Thr Leu Asn Asn Ser Val Ala Leu Asp Pro Ile Asp Ile Ser
```

```
                 1               5                  10                 15
Ile Glu Leu Asn Lys Ala Lys Ser Asp Leu Glu Glu Ser
                20                  25

<210> SEQ ID NO 425
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 425

Ile Thr Leu Asn Asn Ser Val Ala Leu Asp Pro Ile Asp Ile Ser
 1               5                  10                  15

Ile Glu Leu Asn Lys Ala Lys Ser Asp Leu Glu Glu
                20                  25

<210> SEQ ID NO 426
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 426

Ile Thr Leu Asn Asn Ser Val Ala Leu Asp Pro Ile Asp Ile Ser
 1               5                  10                  15

Ile Glu Leu Asn Lys Ala Lys Ser Asp Leu Glu
                20                  25

<210> SEQ ID NO 427
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 427

Ile Thr Leu Asn Asn Ser Val Ala Leu Asp Pro Ile Asp Ile Ser
 1               5                  10                  15

Ile Glu Leu Asn Lys Ala Lys Ser Asp Leu
                20                  25

<210> SEQ ID NO 428
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 428

Ile Thr Leu Asn Asn Ser Val Ala Leu Asp Pro Ile Asp Ile Ser
 1               5                  10                  15

Ile Glu Leu Asn Lys Ala Lys Ser Asp
                20

<210> SEQ ID NO 429
<211> LENGTH: 23
<212> TYPE: PRT
<213> ORGANISM: Artificial Sequence
<220> FEATURE:
```

```
<223> OTHER INFORMATION: Description of Artificial Sequence: synthetic
      peptide

<400> SEQUENCE: 429

Ile Thr Leu Asn Asn Ser Val Ala Leu Asp Pro Ile Asp Ile Ser
 1               5                  10                  15

Ile Glu Leu Asn Lys Ala Lys Ser
                20

<210> SEQ ID NO 430
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 430

Ile Thr Leu Asn Asn Ser Val Ala Leu Asp Pro Ile Asp Ile Ser
 1               5                  10                  15

Ile Glu Leu Asn Lys Ala Lys
                20

<210> SEQ ID NO 431
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 431

Ile Thr Leu Asn Asn Ser Val Ala Leu Asp Pro Ile Asp Ile Ser
 1               5                  10                  15

Ile Glu Leu Asn Lys Ala
                20

<210> SEQ ID NO 432
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 432

Ile Thr Leu Asn Asn Ser Val Ala Leu Asp Pro Ile Asp Ile Ser
 1               5                  10                  15

Ile Glu Leu Asn Lys
                20

<210> SEQ ID NO 433
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 433

Ile Thr Leu Asn Asn Ser Val Ala Leu Asp Pro Ile Asp Ile Ser
 1               5                  10                  15

Ile Glu Leu Asn
```

<210> SEQ ID NO 434
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 434

Ile Thr Leu Asn Asn Ser Val Ala Leu Asp Pro Ile Asp Ile Ser
 1               5                  10                  15

Ile Glu Leu

<210> SEQ ID NO 435
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 435

Ile Thr Leu Asn Asn Ser Val Ala Leu Asp Pro Ile Asp Ile Ser
 1               5                  10                  15

Ile Glu

<210> SEQ ID NO 436
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 436

Ile Thr Leu Asn Asn Ser Val Ala Leu Asp Pro Ile Asp Ile Ser
 1               5                  10                  15

Ile

<210> SEQ ID NO 437
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 437

Ile Thr Leu Asn Asn Ser Val Ala Leu Asp Pro Ile Asp Ile Ser
 1               5                  10                  15

<210> SEQ ID NO 438
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 438

Ile Thr Leu Asn Asn Ser Val Ala Leu Asp Pro Ile Asp Ile
 1               5                  10

<210> SEQ ID NO 439
<211> LENGTH: 13
<212> TYPE: PRT

```
<213> ORGANISM: Artificial Sequence
<220> FEATURE:
<223> OTHER INFORMATION: Description of Artificial Sequence: synthetic
      peptide

<400> SEQUENCE: 439

Ile Thr Leu Asn Asn Ser Val Ala Leu Asp Pro Ile Asp
 1               5                  10

<210> SEQ ID NO 440
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 440

Ile Thr Leu Asn Asn Ser Val Ala Leu Asp Pro Ile
 1               5                  10

<210> SEQ ID NO 441
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 441

Ile Thr Leu Asn Asn Ser Val Ala Leu Asp Pro
 1               5                  10

<210> SEQ ID NO 442
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 442

Ile Thr Leu Asn Asn Ser Val Ala Leu Asp
 1               5                  10

<210> SEQ ID NO 443
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 443

Ile Thr Leu Asn Asn Ser Val Ala Leu
 1               5

<210> SEQ ID NO 444
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 444

Ile Thr Leu Asn Asn Ser Val Ala
 1               5
```

```
<210> SEQ ID NO 445
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 445

Ile Thr Leu Asn Asn Ser Val
 1               5

<210> SEQ ID NO 446
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 446

Ile Thr Leu Asn Asn Ser
 1               5

<210> SEQ ID NO 447
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 447

Thr Leu Asn Asn Ser Val Ala Leu Asp Pro Ile Asp Ile Ser Ile
 1               5                  10                  15

Glu Leu Asn Lys Ala Lys Ser Asp Leu Glu Glu Ser Lys Glu Trp
                20                  25                  30

Ile Arg Arg Ser

<210> SEQ ID NO 448
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 448

Leu Asn Asn Ser Val Ala Leu Asp Pro Ile Asp Ile Ser Ile Glu
 1               5                  10                  15

Leu Asn Lys Ala Lys Ser Asp Leu Glu Glu Ser Lys Glu Trp Ile
                20                  25                  30

Arg Arg Ser

<210> SEQ ID NO 449
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 449

Asn Asn Ser Val Ala Leu Asp Pro Ile Asp Ile Ser Ile Glu Leu
```

Asn Lys Ala Lys Ser Asp Leu Glu Glu Ser Lys Glu Trp Ile Arg
            20                  25                  30

Arg Ser

<210> SEQ ID NO 450
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 450

Asn Ser Val Ala Leu Asp Pro Ile Asp Ile Ser Ile Glu Leu Asn
 1               5                  10                  15

Lys Ala Lys Ser Asp Leu Glu Glu Ser Lys Glu Trp Ile Arg Arg
            20                  25                  30

Ser

<210> SEQ ID NO 451
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 451

Ser Val Ala Leu Asp Pro Ile Asp Ile Ser Ile Glu Leu Asn Lys
 1               5                  10                  15

Ala Lys Ser Asp Leu Glu Glu Ser Lys Glu Trp Ile Arg Arg Ser
            20                  25                  30

<210> SEQ ID NO 452
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 452

Val Ala Leu Asp Pro Ile Asp Ile Ser Ile Glu Leu Asn Lys Ala
 1               5                  10                  15

Lys Ser Asp Leu Glu Glu Ser Lys Glu Trp Ile Arg Arg Ser
            20                  25

<210> SEQ ID NO 453
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 453

Ala Leu Asp Pro Ile Asp Ile Ser Ile Glu Leu Asn Lys Ala Lys
 1               5                  10                  15

Ser Asp Leu Glu Glu Ser Lys Glu Trp Ile Arg Arg Ser
            20                  25

<210> SEQ ID NO 454

```
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 454

Leu Asp Pro Ile Asp Ile Ser Ile Glu Leu Asn Lys Ala Lys Ser
 1               5                  10                  15

Asp Leu Glu Glu Ser Lys Glu Trp Ile Arg Arg Ser
                20                  25

<210> SEQ ID NO 455
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 455

Asp Pro Ile Asp Ile Ser Ile Glu Leu Asn Lys Ala Lys Ser Asp
 1               5                  10                  15

Leu Glu Glu Ser Lys Glu Trp Ile Arg Arg Ser
                20                  25

<210> SEQ ID NO 456
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 456

Pro Ile Asp Ile Ser Ile Glu Leu Asn Lys Ala Lys Ser Asp Leu
 1               5                  10                  15

Glu Glu Ser Lys Glu Trp Ile Arg Arg Ser
                20                  25

<210> SEQ ID NO 457
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 457

Ile Asp Ile Ser Ile Glu Leu Asn Lys Ala Lys Ser Asp Leu Glu
 1               5                  10                  15

Glu Ser Lys Glu Trp Ile Arg Arg Ser
                20

<210> SEQ ID NO 458
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 458

Asp Ile Ser Ile Glu Leu Asn Lys Ala Lys Ser Asp Leu Glu Glu
 1               5                  10                  15
```

Ser Lys Glu Trp Ile Arg Arg Ser
            20

<210> SEQ ID NO 459
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 459

Ile Ser Ile Glu Leu Asn Lys Ala Lys Ser Asp Leu Glu Glu Ser
 1               5                  10                  15

Lys Glu Trp Ile Arg Arg Ser
            20

<210> SEQ ID NO 460
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 460

Ser Ile Glu Leu Asn Lys Ala Lys Ser Asp Leu Glu Glu Ser Lys
 1               5                  10                  15

Glu Trp Ile Arg Arg Ser
            20

<210> SEQ ID NO 461
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 461

Ile Glu Leu Asn Lys Ala Lys Ser Asp Leu Glu Glu Ser Lys Glu
 1               5                  10                  15

Trp Ile Arg Arg Ser
            20

<210> SEQ ID NO 462
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 462

Glu Leu Asn Lys Ala Lys Ser Asp Leu Glu Glu Ser Lys Glu Trp
 1               5                  10                  15

Ile Arg Arg Ser

<210> SEQ ID NO 463
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

```
<400> SEQUENCE: 463

Leu Asn Lys Ala Lys Ser Asp Leu Glu Glu Ser Lys Glu Trp Ile
 1               5                  10                  15

Arg Arg Ser

<210> SEQ ID NO 464
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 464

Asn Lys Ala Lys Ser Asp Leu Glu Glu Ser Lys Glu Trp Ile Arg
 1               5                  10                  15

Arg Ser

<210> SEQ ID NO 465
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 465

Lys Ala Lys Ser Asp Leu Glu Glu Ser Lys Glu Trp Ile Arg Arg Ser
 1               5                  10                  15

<210> SEQ ID NO 466
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 466

Ala Lys Ser Asp Leu Glu Glu Ser Lys Glu Trp Ile Arg Arg Ser
 1               5                  10                  15

<210> SEQ ID NO 467
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 467

Lys Ser Asp Leu Glu Glu Ser Lys Glu Trp Ile Arg Arg Ser
 1               5                  10

<210> SEQ ID NO 468
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 468

Ser Asp Leu Glu Glu Ser Lys Glu Trp Ile Arg Arg Ser
 1               5                  10
```

<210> SEQ ID NO 469
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 469

Asp Leu Glu Glu Ser Lys Glu Trp Ile Arg Arg Ser
 1               5                  10

<210> SEQ ID NO 470
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 470

Leu Glu Glu Ser Lys Glu Trp Ile Arg Arg Ser
 1               5                  10

<210> SEQ ID NO 471
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 471

Glu Glu Ser Lys Glu Trp Ile Arg Arg Ser
 1               5                  10

<210> SEQ ID NO 472
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 472

Glu Ser Lys Glu Trp Ile Arg Arg Ser
 1               5

<210> SEQ ID NO 473
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 473

Ser Lys Glu Trp Ile Arg Arg Ser
 1               5

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 474

Lys Glu Trp Ile Arg Arg Ser
 1               5

<210> SEQ ID NO 475
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 475

Glu Trp Ile Arg Arg Ser
 1               5

<210> SEQ ID NO 476
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 476

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys Leu Lys
                20                  25                  30

Glu Ala Ile Arg

<210> SEQ ID NO 477
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 477

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys Leu Lys
                20                  25                  30

Glu Ala Ile

<210> SEQ ID NO 478
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 478

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys Leu Lys
                20                  25                  30

Glu Ala

<210> SEQ ID NO 479

```
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 479

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys Leu Lys
                20                  25                  30

Glu

<210> SEQ ID NO 480
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 480

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys Leu Lys
                20                  25                  30

<210> SEQ ID NO 481
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 481

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys Leu
                20                  25

<210> SEQ ID NO 482
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 482

Ala Leu Gly Val Ala Thr Ser Ala Gln Ile Thr Ala Ala Val Ala
 1               5                  10                  15

Leu Val Glu Ala Lys Gln Ala Arg Ser Asp Ile Glu Lys
                20                  25

<210> SEQ ID NO 483
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 483
```

```
Ala Leu Gly Val Ala Thr Ser Ala Gln Ile Thr Ala Ala Val Ala
1               5                   10                  15

Leu Val Glu Ala Lys Gln Ala Arg Ser Asp Ile Glu
            20                  25

<210> SEQ ID NO 484
<211> LENGTH: 26
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 484

Ala Leu Gly Val Ala Thr Ser Ala Gln Ile Thr Ala Ala Val Ala
1               5                   10                  15

Leu Val Glu Ala Lys Gln Ala Arg Ser Asp Ile
            20                  25

<210> SEQ ID NO 485
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 485

Ala Leu Gly Val Ala Thr Ser Ala Gln Ile Thr Ala Ala Val Ala
1               5                   10                  15

Leu Val Glu Ala Lys Gln Ala Arg Ser Asp
            20                  25

<210> SEQ ID NO 486
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 486

Ala Leu Gly Val Ala Thr Ser Ala Gln Ile Thr Ala Ala Val Ala
1               5                   10                  15

Leu Val Glu Ala Lys Gln Ala Arg Ser
            20

<210> SEQ ID NO 487
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 487

Ala Leu Gly Val Ala Thr Ser Ala Gln Ile Thr Ala Ala Val Ala
1               5                   10                  15

Leu Val Glu Ala Lys Gln Ala Arg
            20

<210> SEQ ID NO 488
<211> LENGTH: 22
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 488

Ala Leu Gly Val Ala Thr Ser Ala Gln Ile Thr Ala Ala Val Ala
 1               5                  10                  15
Leu Val Glu Ala Lys Gln Ala
             20

<210> SEQ ID NO 489
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 489

Ala Leu Gly Val Ala Thr Ser Ala Gln Ile Thr Ala Ala Val Ala
 1               5                  10                  15
Leu Val Glu Ala Lys Gln
             20

<210> SEQ ID NO 490
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 490

Ala Leu Gly Val Ala Thr Ser Ala Gln Ile Thr Ala Ala Val Ala
 1               5                  10                  15
Leu Val Glu Ala Lys
             20

<210> SEQ ID NO 491
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 491

Ala Leu Gly Val Ala Thr Ser Ala Gln Ile Thr Ala Ala Val Ala
 1               5                  10                  15
Leu Val Glu Ala

<210> SEQ ID NO 492
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 492

Ala Leu Gly Val Ala Thr Ser Ala Gln Ile Thr Ala Ala Val Ala
 1               5                  10                  15
Leu Val Glu
```

<210> SEQ ID NO 493
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 493

Ala Leu Gly Val Ala Thr Ser Ala Gln Ile Thr Ala Ala Val Ala
 1               5                  10                  15

Leu Val

<210> SEQ ID NO 494
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 494

Ala Leu Gly Val Ala Thr Ser Ala Gln Ile Thr Ala Ala Val Ala
 1               5                  10                  15

Leu

<210> SEQ ID NO 495
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 495

Ala Leu Gly Val Ala Thr Ser Ala Gln Ile Thr Ala Ala Val Ala
 1               5                  10                  15

<210> SEQ ID NO 496
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 496

Ala Leu Gly Val Ala Thr Ser Ala Gln Ile Thr Ala Ala Val
 1               5                  10

<210> SEQ ID NO 497
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 497

Ala Leu Gly Val Ala Thr Ser Ala Gln Ile Thr Ala Ala
 1               5                  10

<210> SEQ ID NO 498
<211> LENGTH: 12
<212> TYPE: PRT
<213> ORGANISM: Artificial Sequence
<220> FEATURE:

<223> OTHER INFORMATION: Description of Artificial Sequence: synthetic
      peptide

<400> SEQUENCE: 498

Ala Leu Gly Val Ala Thr Ser Ala Gln Ile Thr Ala
  1               5                  10

<210> SEQ ID NO 499
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 499

Ala Leu Gly Val Ala Thr Ser Ala Gln Ile Thr
  1               5                  10

<210> SEQ ID NO 500
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 500

Ala Leu Gly Val Ala Thr Ser Ala Gln Ile
  1               5                  10

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 501

Ala Leu Gly Val Ala Thr Ser Ala Gln
  1               5

<210> SEQ ID NO 502
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 502

Ala Leu Gly Val Ala Thr Ser Ala
  1               5

<210> SEQ ID NO 503
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 503

Ala Leu Gly Val Ala Thr Ser
  1               5

<210> SEQ ID NO 504
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 504

Ala Leu Gly Val Ala Thr
 1               5

<210> SEQ ID NO 505
<211> LENGTH: 34
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 505

Leu Gly Val Ala Thr Ser Ala Gln Ile Thr Ala Ala Val Ala Leu
 1               5                  10                  15

Val Glu Ala Lys Gln Ala Arg Ser Asp Ile Glu Lys Leu Lys Glu
                20                  25                  30

Ala Ile Arg Asp

<210> SEQ ID NO 506
<211> LENGTH: 33
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 506

Gly Val Ala Thr Ser Ala Gln Ile Thr Ala Ala Val Ala Leu Val
 1               5                  10                  15

Glu Ala Lys Gln Ala Arg Ser Asp Ile Glu Lys Leu Lys Glu Ala
                20                  25                  30

Ile Arg Asp

<210> SEQ ID NO 507
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 507

Val Ala Thr Ser Ala Gln Ile Thr Ala Ala Val Ala Leu Val Glu
 1               5                  10                  15

Ala Lys Gln Ala Arg Ser Asp Ile Glu Lys Leu Lys Glu Ala Ile
                20                  25                  30

Arg Asp

<210> SEQ ID NO 508
<211> LENGTH: 31
<212> TYPE: PRT
<213> ORGANISM: Artificial Sequence
<220> FEATURE:
<223> OTHER INFORMATION: Description of Artificial Sequence: synthetic
      peptide -continued

```
<400> SEQUENCE: 508

Ala Thr Ser Ala Gln Ile Thr Ala Ala Val Ala Leu Val Glu Ala
 1               5                  10                  15
Lys Gln Ala Arg Ser Asp Ile Glu Lys Leu Lys Glu Ala Ile Arg Asp
            20                  25                  30

<210> SEQ ID NO 509
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 509

Thr Ser Ala Gln Ile Thr Ala Ala Val Ala Leu Val Glu Ala Lys
 1               5                  10                  15
Gln Ala Arg Ser Asp Ile Glu Lys Leu Lys Glu Ala Ile Arg Asp
            20                  25                  30

<210> SEQ ID NO 510
<211> LENGTH: 29
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 510

Ser Ala Gln Ile Thr Ala Ala Val Ala Leu Val Glu Ala Lys Gln
 1               5                  10                  15
Ala Arg Ser Asp Ile Glu Lys Leu Lys Glu Ala Ile Arg Asp
            20                  25

<210> SEQ ID NO 511
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 511

Ala Gln Ile Thr Ala Ala Val Ala Leu Val Glu Ala Lys Gln Ala
 1               5                  10                  15
Arg Ser Asp Ile Glu Lys Leu Lys Glu Ala Ile Arg Asp
            20                  25

<210> SEQ ID NO 512
<211> LENGTH: 27
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 512

Gln Ile Thr Ala Ala Val Ala Leu Val Glu Ala Lys Gln Ala Arg
 1               5                  10                  15
Ser Asp Ile Glu Lys Leu Lys Glu Ala Ile Arg Asp
            20                  25

<210> SEQ ID NO 513
<211> LENGTH: 26
```

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 513

Ile Thr Ala Ala Val Ala Leu Val Glu Ala Lys Gln Ala Arg Ser
 1               5                  10                  15

Asp Ile Glu Lys Leu Lys Glu Ala Ile Arg Asp
            20                  25

<210> SEQ ID NO 514
<211> LENGTH: 25
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 514

Thr Ala Ala Val Ala Leu Val Glu Ala Lys Gln Ala Arg Ser Asp
 1               5                  10                  15

Ile Glu Lys Leu Lys Glu Ala Ile Arg Asp
            20                  25

<210> SEQ ID NO 515
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 515

Ala Ala Val Ala Leu Val Glu Ala Lys Gln Ala Arg Ser Asp Ile
 1               5                  10                  15

Glu Lys Leu Lys Glu Ala Ile Arg Asp
            20

<210> SEQ ID NO 516
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 516

Ala Val Ala Leu Val Glu Ala Lys Gln Ala Arg Ser Asp Ile Glu
 1               5                  10                  15

Lys Leu Lys Glu Ala Ile Arg Asp
            20

<210> SEQ ID NO 517
<211> LENGTH: 22
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 517

Val Ala Leu Val Glu Ala Lys Gln Ala Arg Ser Asp Ile Glu Lys
 1               5                  10                  15
```

Leu Lys Glu Ala Ile Arg Asp
            20

<210> SEQ ID NO 518
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 518

Ala Leu Val Glu Ala Lys Gln Ala Arg Ser Asp Ile Glu Lys Leu
 1               5                  10                  15

Lys Glu Ala Ile Arg Asp
            20

<210> SEQ ID NO 519
<211> LENGTH: 20
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 519

Leu Val Glu Ala Lys Gln Ala Arg Ser Asp Ile Glu Lys Leu Lys
 1               5                  10                  15

Glu Ala Ile Arg Asp
            20

<210> SEQ ID NO 520
<211> LENGTH: 19
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 520

Val Glu Ala Lys Gln Ala Arg Ser Asp Ile Glu Lys Leu Lys Glu
 1               5                  10                  15

Ala Ile Arg Asp

<210> SEQ ID NO 521
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 521

Glu Ala Lys Gln Ala Arg Ser Asp Ile Glu Lys Leu Lys Glu Ala
 1               5                  10                  15

Ile Arg Asp

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 522

```
Ala Lys Gln Ala Arg Ser Asp Ile Glu Lys Leu Lys Glu Ala Ile
 1               5                  10                  15

Arg Asp
```

<210> SEQ ID NO 523
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 523

```
Lys Gln Ala Arg Ser Asp Ile Glu Lys Leu Lys Glu Ala Ile Arg Asp
 1               5                  10                  15
```

<210> SEQ ID NO 524
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 524

```
Gln Ala Arg Ser Asp Ile Glu Lys Leu Lys Glu Ala Ile Arg Asp
 1               5                  10                  15
```

<210> SEQ ID NO 525
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 525

```
Ala Arg Ser Asp Ile Glu Lys Leu Lys Glu Ala Ile Arg Asp
 1               5                  10
```

<210> SEQ ID NO 526
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 526

```
Arg Ser Asp Ile Glu Lys Leu Lys Glu Ala Ile Arg Asp
 1               5                  10
```

<210> SEQ ID NO 527
<211> LENGTH: 12
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 527

```
Ser Asp Ile Glu Lys Leu Lys Glu Ala Ile Arg Asp
 1               5                  10
```

<210> SEQ ID NO 528
<211> LENGTH: 11

-continued

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 528

Asp Ile Glu Lys Leu Lys Glu Ala Ile Arg Asp
 1               5                  10

<210> SEQ ID NO 529
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 529

Ile Glu Lys Leu Lys Glu Ala Ile Arg Asp
 1               5                  10

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 530

Glu Lys Leu Lys Glu Ala Ile Arg Asp
 1               5

<210> SEQ ID NO 531
<211> LENGTH: 8
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 531

Lys Leu Lys Glu Ala Ile Arg Asp
 1               5

<210> SEQ ID NO 532
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 532

Leu Lys Glu Ala Ile Arg Asp
 1               5

<210> SEQ ID NO 533
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 533

Lys Glu Ala Ile Arg Asp
```

<210> SEQ ID NO 534
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 534

Tyr Thr Gly Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 535
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 535

Tyr Thr Asn Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 536
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 536

Tyr Thr Ser Ile Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 537
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 537

Tyr Thr Ser Leu Ile Tyr Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

<210> SEQ ID NO 538
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 538

Tyr Thr Ser Leu Ile His Arg Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 539
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 539

Tyr Thr Ser Leu Ile His Asn Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 540
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 540

Tyr Thr Ser Leu Ile His Thr Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 541
<211> LENGTH: 36
<212> TYPE: PRT
<213> ORGANISM: Artificial Sequence
<220> FEATURE:
<223> OTHER INFORMATION: Description of Artificial Sequence: synthetic peptide

<400> SEQUENCE: 541

Tyr Thr Ser Leu Ile His Ser Leu Leu Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

```
Trp Asn Trp Phe
        35

<210> SEQ ID NO 542
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 542

Ser Asn Leu Leu Arg Ala Ile Glu Ala Gln Gln His Leu Leu Gln Leu
  1               5                  10                  15

Thr Val Trp Gln Ile Lys Gln Leu Gln Ala Arg Ile Leu Ala Val Glu
             20                  25                  30

Arg Tyr Leu Lys Asp Gln
        35

<210> SEQ ID NO 543
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 543

Asn Asn Leu Leu Arg Ala Ile Asp Ala Gln Gln His Leu Leu Gln Leu
  1               5                  10                  15

Thr Val Trp Gln Ile Lys Gln Leu Gln Ala Arg Ile Leu Ala Val Glu
             20                  25                  30

Arg Tyr Leu Lys Asp Gln
        35

<210> SEQ ID NO 544
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 544

Asn Asn Leu Leu Arg Ala Ile Gln Ala Gln Gln His Leu Leu Gln Leu
  1               5                  10                  15

Thr Val Trp Gln Ile Lys Gln Leu Gln Ala Arg Ile Leu Ala Val Glu
             20                  25                  30

Arg Tyr Leu Lys Asp Gln
        35

<210> SEQ ID NO 545
<211> LENGTH: 38
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 545

Asn Asn Leu Leu Arg Ala Ile Glu Ala Gln Gln His Met Leu Gln Leu
  1               5                  10                  15

Thr Val Trp Gln Ile Lys Gln Leu Gln Ala Arg Ile Leu Ala Val Glu
```

-continued

```
                20              25              30
Arg Tyr Leu Lys Asp Gln
        35
```

US 7,582,301 B1

LONG-LASTING ANTIVIRAL FUSION INHIBITOR PEPTIDE CONJUGATES COMPRISING ALBUMIN AND HUMAN IMMUNODEFICIENCY VIRUS (HIV) PEPTIDES

FIELD OF THE INVENTION

This invention relates to modified peptides that are inhibitors of viral activity and/or exhibit antifusogenic properties. In particular, this invention relates to modified peptide inhibitors of human immunodeficiency virus (HIV), respiratory syncytial virus (RSV), human parainfluenza virus (HPV), measles virus (MeV), and simian immunodeficiency virus (SIV) with long duration of action for the treatment of the respective viral infections. The invention also relates to conjugates of the modified peptides and endogenous carriers, particularly conjugates of the modified peptides and various mobile blood components, particularly mobile endogenous proteins.

BACKGROUND OF THE INVENTION

Membrane fusion events, while commonplace in normal cell biological processes, are also involved in a variety of disease states, including, for example the entry of enveloped viruses into cells. Peptides are known that inhibit or otherwise disrupt membrane fusion-associated events, including, for example, inhibiting retroviral transmission to uninfected cells. As an example, the synthetic peptides DP-107 and DP-178 derived from separate domains within the human immunodeficiency virus type 1 ("HIV-1") transmembrane ("TM") glycoprotein gp41, are potent inhibitors of HIV-1 infection and HIV induced cell-cell fusion.

Lambert, et al., "Peptides from Conserved Regions of Paramyxovirus Fusion (F) Proteins are Potent Inhibitors of Viral Fusion," Proc. Natl. Acad. Science U.S.A., Mar. 5, 1996, Vol. 93 (5), pp. 2186-91, discloses that the synthetic peptides DP-107 and DP-178 (T-20), derived from separate domains within the human immunodeficiency virus type 1 (HIV-1) transmembrane (TM) protein, gp41, are potent inhibitors of HIV-1 infection and fusion. Using a computer searching strategy (computerized antiviral searching technology, C.A.S.T.) based on the predicted secondary structure of DP-107 and DP-178 (T-20), Lambert, et al. identified conserved heptad repeat domains analogous to the DP-107 and DP-178 regions of HIV-1 gp41 within the glycoproteins of other fusogenic viruses. Antiviral peptides derived from three representative paramyxoviruses, respiratory syncytial virus (RSV), human parainfluenza virus type 3 (HPIV-3), and measles virus (MV) blocked homologous virus-mediated syncytium formation and exhibited $EC_{50}$ values in the range 0.015-0.250 µM. Moreover, these peptides were highly selective for the virus of origin.

U.S. Pat. Nos. 6,013,263, 6,017,536 and 6,020,459 incorporated herein in their entirety, likewise disclose that the 36 amino acid peptide DP178 corresponding to amino acids 638 to 673 of gp41 from the HIV-1 isolate LAI (HIV-1$_{LAI}$), and the 38 amino acid peptide DP107 corresponding to amino acids 558-595 of gp41 from the HIV-1$_{LAI}$, both exhibit potent anti-HIV-1 activity.

While many of the anti-viral or anti-fusogenic peptides described in the art exhibit potent anti-viral and/or anti-fusogenic activity, these peptides suffer from short plasma half-lifes in vivo, primarily due to rapid serum clearance and peptidase and protease activity. This in turn greatly reduces the effective anti-viral activity of the peptides. There is therefore a need for a method of prolonging the half-life of existing anti-viral and/or anti-fusogenic peptides and providing for longer duration of action of these peptides in vivo.

SUMMARY OF THE INVENTION

The present invention meets these and other needs and is directed to modified peptides having anti-viral activity and/or anti-fusogenic activity. These modified peptides provide for an increased stability in vivo and a reduced susceptibility to peptidase or protease degradation. These modified peptides thereby minimize, e.g., the need for more frequent, or even continual, administration of the peptides. The products of varying embodiments of the present invention can be used, e.g., as a prophylactic against and/or treatment for infection of a number of viruses, including human immunodeficiency virus (HIV), human respiratory syncytial virus (RSV), human parainfluenza virus (HPV), measles virus (MeV) and simian immunodeficiency virus (SIV). Modification of other peptides involved in viral transfection (e.g., Hepatitis, Epstein Barr and other related viruses) is also within the scope of the invention.

This invention relates to chemically reactive modifications of peptides exhibiting anti-viral and/or anti-fusogenic activity such that the modified peptides can react with available functionalities on blood components to form stable covalent bonds. In one embodiment of the invention, the modified peptides comprise a reactive group which is reactive with amino groups, hydroxyl groups, or thiol groups on blood components to form stable covalent bonds. In another embodiment of the invention, the reactive group can be a maleimide which is reactive with a thiol group on a blood protein, including a mobile blood protein such as albumin.

In particular, the invention relates to such chemically reactive modifications of DP107 and DP178 peptides and analogs thereof, including peptides comprised of amino acid sequences from other (non-HIV) viruses that correspond to the gp41 region of HIV from which DP107 and DP178 are derived and that exhibit anti-viral or anti-fusogenic activity. More particularly, these peptides can exhibit anti-viral activity against, among others, human respiratory syncytial virus (RSV), human parainfluenza virus (HPV), measles virus (MeV) and simian immunodeficiency virus (SIV). The invention also relates to such chemically reactive modifications of the peptides of SEQ ID NO:1 to SEQ ID NO:86.

The invention also relates to compositions for use in the prevention and/or treatment of viral infection comprising a peptide that exhibits anti-viral activity modified with a reactive group as described. More particularly, the invention relates to such compositions for use in the prevention and/or treatment of AIDS, human respiratory syncytial virus (RSV), human parainfluenza virus (HPV), measles virus (MeV) and simian immunodeficiency virus (SIV).

BRIEF DESCRIPTION OF THE TABLES

The invention will be better understood by reference to the Tables, in which:

Table 1 lists the commonly occurring amino acids together with their one letter and three letter abbreviations, and common protecting groups.

Table 2 shows DP178 carboxy truncations including SEQ ID NO:1 and 87-116.

Table 3 shows DP178 amino truncations including SEQ ID NO:1 and 117-146.

Table 4 shows DP107 carboxy truncations including SEQ ID NO:2 and 147-178.

Table 5 shows DP107 amino truncations including SEQ ID NO:2 and 179-210.

Table 6 shows HIV-2$_{NIHZ}$ DP178 analog carboxy truncations including SEQ ID NO:7 and 211-240.

Table 7 shows HIV-2$_{NIHZ}$ DP178 analog amino truncations including SEQ ID NO:7 and 241-270.

Table 8 shows RSV F2 region DP107 analog carboxy truncations including SEQ ID NO:13 and 271-312.

Table 9 shows RSV F2 region DP107 analog amino truncations including SEQ ID NO:313-353.

Table 10 shows RSV F1 region DP178 analog carboxy truncations including SEQ ID NO:354-385.

Table 11 shows RSV F1 region DP178 analog amino truncations including SEQ ID NO:386-416.

Table 12 shows HPV3 F1 region DP178 analog carboxy truncations including SEQ ID NO:417-446.

Table 13 shows HPV3 F1 region DP178 analog amino truncations including SEQ ID NO:447-475.

Table 14 shows HPV3 F1 region DP107 analog carboxy truncations including SEQ ID NO:476-504.

Table 15 shows HPV3 F1 region DP107 analog amino truncations including SEQ ID NO:505-533.

Table 16 shows representative anti-RSV peptides of SEQ ID NO:15-30.

Table 17 shows representative anti-HPV3 peptides of SEQ ID NO:33-62.

Table 18 shows representative anti-SIV peptides of SEQ ID NO:64-73.

Table 19 shows representative anti-MeV peptides of SEQ ID NO:76-86.

BRIEF DESCRIPTION OF SEQUENCE LISTING

The invention will be better understood by reference to the Sequence Listing, in which:
SEQ ID NO:1 shows the peptide sequence of DP178;
SEQ ID NO:2 shows the peptide sequence of DP107;
SEQ ID NO:3-7 show peptide sequences of certain DP178 analogs;
SEQ ID NO:8-9 show peptide sequences of certain DP107 analogs;
SEQ ID NO:10-30 show the peptide sequences of RSV F1 region and F2 region corresponding to DP178 and DP107, and representative anti-RSV peptides;
SEQ ID NO:31-62 show the peptide sequences of HPIV3 F1 region corresponding to DP178 and DP107, and representative anti-HPIV3 peptides;
SEQ ID NO:63-73 show peptide sequences of SIV corresponding to DP178 and representative anti-SIV peptides;
SEQ ID NO:74-86 show peptide sequences of MeV corresponding to DP178 and representative anti-MeV peptides;
SEQ ID NO:87-116 show peptide sequences of DP178 carboxy truncations;
SEQ ID NO:117-146 show peptide sequences of DP178 amino truncations;
SEQ ID NO:147-178 show peptide sequences of DP107 carboxy truncations;
SEQ ID NO:179-210 show peptide sequences of DP107 amino truncations;
SEQ ID NO:211-240 show peptide sequences of HIV-2$_{NIHZ}$ DP178 analog carboxy truncations;
SEQ ID NO:241-270 show peptide sequences of HIV-2$_{NIHZ}$ DP178 analog amino truncations;
SEQ ID NO:271-312 show peptide sequences of RSV F2 region DP107 analog carboxy truncations;
SEQ ID NO:313-353 show peptide sequences of RSV F2 region DP107 analog amino truncations;
SEQ ID NO:354-385 show peptide sequences of RSV F1 region DP178 analog carboxy truncations;
SEQ ID NO:386-416 show peptide sequences of RSV F1 region DP178 analog amino truncations;
SEQ ID NO:417-446 show peptide sequences of HPV3 F1 region DP178 analog carboxy truncations;
SEQ ID NO:447-475 show peptide sequences of HPV3 F1 region DP178 analog amino truncations;
SEQ ID NO:476-504 show peptide sequences of HPV3 F1 region DP107 analog carboxy truncations;
SEQ ID NO:505-533 show peptide sequences of HPV3 F1 region DP107 analog amino truncations;
SEQ ID NO:534-541 show peptide sequences of DP178 with deletion and insertion of an amino acid; and
SEQ ID NO:542-545 show peptide sequences of DP107 with deletion and insertion of an amino acid.

DETAILED DESCRIPTION OF THE INVENTION

To ensure a complete understanding of the invention the following definitions are provided:

Anti-viral peptides: As used herein, anti-viral peptides shall refer to peptides that inhibit viral infection of cells, by, for example, inhibiting cell-cell fusion or free virus infection. The route of infection may involve membrane fusion, as occurs in the case of enveloped viruses, or some other fusion event involving viral and cellular structures. Peptides that inhibit viral infection by a particular virus may be referenced with respect to that particular virus, e.g., anti-HIV peptide, anti-RSV peptide, etc.

Antifusogenic peptides: Antifusogenic peptides are peptides demonstrating an ability to inhibit or reduce the level of membrane fusion events between two or more entities, e.g., virus-cell or cell-cell, relative to the level of membrane fusion that occurs in the absence of the peptide.

HIV and anti-HIV peptides: The human immunodeficiency virus (HIV), which is responsible for acquired immune deficiency syndrome (AIDS), is a member of the lentivirus family of retroviruses. There are two prevalent types of HIV, HIV-1 and HIV-2, with various strain of each having been identified. HIV targets CD-4+ cells, and viral entry depends on binding of the HIV protein gp41 to CD-4+ cell surface receptors. Anti-HIV peptides refer to peptides that exhibit anti-viral activity against HIV, including inhibiting CD-4+ cell infection by free virus and/or inhibiting HIV-induced syncytia formation between infected and uninfected CD-4+ cells.

SIV and anti-SIV peptides: Simian immunodeficiency viruses (SIV) are lentiviruses that cause acquired immunodeficiency syndrome (AIDS)-like illnesses in susceptible monkeys. Anti-SIV peptides are peptides that exhibit anti-viral activity against SIV, including inhibiting of infection of cells by the SIV virus and inhibiting syncytia formation between infected and uninfected cells.

RSV and anti-RSV peptides: Respiratory syncytial virus (RSV) is a respiratory pathogen, especially dangerous in infants and small children where it can cause bronchiolitis (inflammation of the small air passages) and pneumonia. RSVs are negative sense, single stranded RNA viruses and are members of the Paramyxoviridae family of viruses. The route of infection of RSV is typically through the mucous membranes by the respiratory tract, i.e., nose, throat, windpipe and bronchi and bronchioles. Anti-RSV peptides are peptides that exhibit anti-viral activity against RSV, including inhibiting mucous membrane cell infection by free RSV virus and syncytia formation between infection and uninfected cells.

HPV and anti-HPV peptides: Human parainfluenza virus (HPIV or HPV), like RSV, is another leading cause of respiratory tract disease, and like RSVs, are negative sense, single stranded RNA viruses that are members of the Paramyxoviridae family of viruses. There are four recognized serotypes of HPIV—HPIV-1, HPIV-2, HPIV-3 and HPIV-4. HPIV-1 is the leading cause of croup in children, and both HPIV-1 and HPIV-2 cause upper and lower respiratory tract illnesses. HPIV-3 is more often associated with bronchiolitis and pneumonia. Anti-HPV peptides are peptides that exhibit anti-viral activity against HPV, including inhibiting infection by free HPV virus and syncytia formation between infected and uninfected cells.

MeV and anti-Mev peptides: Measles virus (VM or MeV) is an enveloped negative, single-stranded RNA virus belonging to the Paramyxoviridae family of viruses. Like RSV and HPV, MeV causes respiratory disease, and also produces an immuno-suppression responsible for additional, opportunistic infections. In some cases, MeV can establish infection of the brain leading to severe neurological complications. Anti-MeV peptides are peptides that exhibit anti-viral activity against MeV, including inhibiting infection by free MeV virus and syncytia formation between infected and uninfected cells.

DP-178 and DP178 analogs: Unless otherwise indicated explicitly or by context, DP-178 means the 36 amino acid DP-178 peptide corresponding to amino acid residues 638-673 of the gp41 glycoprotein of HIV-1 isolate LAI ($HIV_{LAI}$) and having the sequence:

YTSLIHSLIEESQNQQEKNEQELLELDKWASLWNWF (SEQ ID NO:1)

as well as truncations, deletions and/or insertions thereof. Truncations of the DP178 peptide may comprise peptides of between 3-36 amino acids. Deletions consist of the removal of one or more amino acid residues from the DP178 peptide, and may involve the removal of a single contiguous portion of the peptide sequence or multiple portions. Insertions may comprise single amino acid residues or stretches of residues and may be made at the carboxy or amino terminal end of the DP178 peptide or at a position internal to the peptide.

DP178 peptide analogs are peptides whose amino acid sequences are comprised of the amino acid sequences of peptide regions of viruses other than $HIV\text{-}1_{LAI}$ that correspond to the gp41 region from which DP178 was derived, as well as an truncations, deletions or insertions thereof. Such other viruses may include, but are not limited to, other HIV isolates such as $HIV\text{-}2_{NIHZ}$, respiratory syncytial virus (RSV), human parainfluenza virus (HPV), simian immunodeficiency virus (SIV), and measles virus (MeV). DP178 analogs also refer to those peptide sequences identified or recognized by the ALLMOTI5, 107×178×4 and PLZIP search motifs described in U.S. Pat. Nos. 6,013,263, 6,017,536 and 6,020,459 and incorporated herein, having structural and/or amino acid motif similarity to DP178. DP178 analogs further refer to peptides described as "DP178-like" as that term is defined in U.S. Pat. Nos. 6,013,263, 6,017,536 and 6,020,459.

DP-107 and DP107 analogs: Unless otherwise indicated explicitly or by context, DP-107 means the 38 amino acid DP-107 peptide corresponding to amino acid residues 558-595 of the gp41 protein of HIV-1 isolate LAI ($HIV_{LAI}$) and having the sequence:

NNLLRAIEAQQHLLQLTVWQIKQLQA-RILAVERYLKDQ (SEQ ID NO:2)

as well as truncations, deletions and/or insertions thereof. Truncations of the DP107 peptide may comprise peptides of between 3-38 amino acids. Deletions consist of the removal of one or more amino acid residues from the DP107 peptide, and may involve the removal of a single contiguous portion of the peptide sequence or multiple portions. Insertions may comprise single amino acid residues or stretches of residues and may be made at the carboxy or amino terminal end of the DP107 peptide or at a position internal to the peptide.

DP107 peptide analogs are peptides whose amino acid sequences are comprised of the amino acid sequences of peptide regions of viruses other than $HIV\text{-}1_{LAI}$ that correspond to the gp41 region from which DP107 was derived, as well as truncations, deletions and/or insertions thereof. Such other viruses may include, but are not limited to, other HIV isolates such as $HIV\text{-}2_{NIHZ}$, respiratory syncytial virus (RSV), human parainfluenza virus (HPV), simian immunodeficiency virus (SIV), and measles virus (MeV). DP107 analogs also refer to those peptide sequences identified or recognized by the ALLMOTI5, 107×178×4 and PLZIP search motifs described in U.S. Pat. Nos. 6,013,263, 6,017,536 and 6,020,459 and incorporated herein, having structural and/or amino acid motif similarity to DP107. DP107 analogs further refer to peptides described as "DP 107-like" as that term is defined in U.S. Pat. Nos. 6,013,263, 6,017,536 and 6,020,459.

Reactive Groups: Reactive groups are chemical groups capable of forming a covalent bond. Such reactive groups are coupled or bonded to a DP-107 or DP-178 peptide or analogs thereof or other anti-viral or anti-fusogenic peptide of interest. Reactive groups will generally be stable in an aqueous environment and will usually be carboxy, phosphoryl, or convenient acyl group, either as an ester or a mixed anhydride, or an imidate, thereby capable of forming a covalent bond with functionalities such as an amino group, a hydroxy or a thiol at the target site on mobile blood components. For the most part, the esters will involve phenolic compounds, or be thiol esters, alkyl esters, phosphate esters, or the like.

Functionalities: Functionalities are groups on blood components to which reactive groups on modified anti-viral peptides react to form covalent bonds. Functionalities include hydroxyl groups for bonding to ester reactive entities; thiol groups for bonding to maleimides, imidates and thioester groups; amino groups for bonding to carboxy, phosphoryl or acyl groups and carboxyl groups for bonding to amino groups.

Blood Components: Blood components may be either fixed or mobile. Fixed blood components are non-mobile blood components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding 5, more usually one minute. These blood components are not membrane-associated and are present in the blood for extended periods of time and are present in a minimum concentration of at least 0.1 μg/ml. Mobile blood components include serum albumin, transferrin, ferritin and immunoglobulin's such as IgM and IgG. The half-life of mobile blood components is at least about 12 hours.

Protective Groups: Protective groups are chemical moieties utilized to protect peptide derivatives from reacting with themselves. Various protective groups are disclosed herein and in U.S. Pat. No. 5,493,007, which is hereby incorporated by reference. Such protective groups include acetyl, fluorenylmethyloxycarbonyl (Fmoc), t-butyloxycarbonyl (Boc), benzyloxycarbonyl (CBZ), and the like. The specific protected amino acids are depicted in Table 1.

TABLE 1

NATURAL AMINO ACIDS AND THEIR ABBREVIATIONS

| Name | 3-Letter Abbreviation | 1-Letter Abbreviation | Modified Amino Acids |
|---|---|---|---|
| Alanine | Ala | A | Fmoc-Ala-OH |
| Arginine | Arg | R | Fmoc-Arg(Pbf)-OH |
| Asparagine | Asn | N | Fmoc-Asn(Trt)-OH |
| Aspartic acid | Asp | D | Asp(tBu)-OH |
| Cysteine | Cys | C | Fmoc-Cys(Trt) |
| Glutamic acid | Glu | E | Fmoc-Glu(tBu)-OH |
| Glutamine | Gln | Q | Fmoc-Gln(Trt)-OH |
| Glycine | Gly | G | Fmoc-Gly-OH |
| Histidine | His | H | Fmoc-His(Trt)-OH |
| Isoleucine | Ile | I | Fmoc-Ile-OH |
| Leucine | Leu | L | Fmoc-Leu-OH |
| Lysine | Lys | Z | Boc-Lys(Aloc)-OH |
| Lysine | Lys | X | Fmoc-Lys(Aloc)-OH |
| Lysine | Lys | K | Fmoc-Lys(Mtt)-OH |
| Methionine | Met | M | Fmoc-Met-OH |
| Phenylalanine | Phe | F | Fmoc-Phe-OH |
| Proline | Pro | P | Fmoc-Pro-OH |
| Serine | Ser | S | Fmoc-Ser(tBu)-OH |
| Threonine | Thr | T | Fmoc-Thr(tBu)-OH |
| Tryptophan | Trp | W | Fmoc-Trp(Boc)-OH |
| Tyrosine | Tyr | Y | Boc-Tyr(tBu)-OH |
| Valine | Val | V | Fmoc-Val-OH |

Linking Groups: Linking (spacer) groups are chemical moieties that link or connect reactive entities to antiviral or antifusogenic peptides. Linking groups may comprise one or more alkyl moeities, alkoxy moeity, alkenyl moeity, alkynyl moeity or amino moeity substituted by alkyl moeities, cycloalkyl moeity, polycyclic moeity, aryl moeity, polyaryl moeities, substituted aryl moeities, heterocyclic moeities, and substituted heterocyclic moeities. Linking groups may also comprise poly ethoxy amino acids, such as AEA ((2-amino) ethoxy acetic acid) or a preferred linking group AEEA ([2-(2-amino) ethoxy)] ethoxy acetic acid.

Sensitive Functional Groups—A sensitive functional group is a group of atoms that represents a potential reaction site on an antiviral and/or antifusogenic peptide. If present, a sensitive functional group may be chosen as the attachment point for the linker-reactive group modification. Sensitive functional groups include but are not limited to carboxyl, amino, thiol, and hydroxyl groups.

Modified Peptides—A modified peptide is an antiviral and/or antifusogenic peptide that has been modified by attaching a reactive group. The reactive group may be attached to the peptide either via a linking group, or optionally without using a linking group. It is also contemplated that one or more additional amino acids may be added to the peptide to facilitate the attachment of the reactive entity. Modified peptides may be administered in vivo such that conjugation with blood components occurs in vivo, or they may be first conjugated to blood components in vitro and the resulting conjugated peptide (as defined below) administered in vivo.

Conjugated Peptides—A conjugated peptide is a modified peptide that has been conjugated to a blood component via a covalent bond formed between the reactive group of the modified peptide and the functionalities of the blood component, with or without a linking group. As used throughout this application, the term "conjugated peptide" can be made more specific to refer to particular conjugated peptides, for example "conjugated DP178" or "conjugated DP107."

Taking into account these definitions, the present invention takes advantage of the properties of existing anti-viral and antifusogenic peptides. The viruses that may be inhibited by the peptides include, but are not limited to all strains of viruses listed, e.g., in U.S. Pat. Nos. 6,013,263, 6,017,536 and 6,020,459 at Tables V-VII and IX-XIV therein. These viruses include, e.g., human retroviruses, including HIV-1, HIV-2, and human T-lympocyte viruses (HTLV-I and HTLV-II), and non-human retroviruses, including bovine leukosis virus, feline sarcoma virus, feline leukemia virus, simian immunodeficiency virus (SIV), simian sarcoma virus, simian leukemia, and sheep progress pneumonia virus. Non-retroviral viruses may also be inhibited by the peptides of the present invention, including human respiratory syncytial virus (RSV), canine distemper virus, Newcastle Disease virus, human parainfluenza virus (HPIV), influenza viruses, measles viruses (MeV), Epstein-Barr viruses, hepatitis B viruses, and simian Mason-Pfizer viruses. Non-enveloped viruses may also be inhibited by the peptides of the present invention, and include, but are not limited to, picornaviruses such as polio viruses, hepatitis A virus, enteroviruses, echoviruses, coxsackie viruses, papovaviruses such as papilloma virus, parvoviruses, adenoviruses, and reoviruses.

As an example, the mechanism of action of HIV fusion peptides has been described as discussed in the background section of this application and antiviral and antifusogenic properties of the peptides have been well established. A synthetic peptide corresponding to the carboxyl-terminal ectodomain sequence (for instance, amino acid residues 643-678 of HIV-1 class B, of the LAI strain or residues 638-673 from similar strain as well as residues 558-595) has been shown to inhibit virus-mediated cell-cell fusion completely at low concentration. The fusion peptide competes with the leucine zipper region of the native viral gp41 thus resulting in the interference of the fusion/infection of the virus into the cell.

The focus of the present invention is to modify a selected anti-viral and/or antifusogenic peptide with the DAC (Drug Activity Complex) technology to confer to this peptide improved bio-availability, extended half-life and better distribution through selective conjugation of the peptide onto a protein carrier but without modifying the peptide's anti-viral properties. The carrier of choice (but not limited to) for this invention would be albumin conjugated through its free thiol by an anti-viral and/or antifusogenic peptide modified with a maleimide moiety.

Several peptide sequences have been described in the literature as highly potent for the prevention of HIV-1 fusion/infection. As examples, peptide DP178 binds to a conformation of gp41 that is relevant for fusion. Thus in one embodiment of the invention, DP178 and DP178-like peptides are modified. Likewise, other embodiments of the invention include modification of DP107 and DP107-like peptide for use against HIV, as well as peptides analagous to DP107 and DP178 that are found in RSV, HPV, MeV and SIV viruses.

1. DP178 and DP107

A. DP178 Peptides

The DP178 peptide corresponds to amino acid residues 638 to 673 of the transmembrane protein gp41 from the HIV-1$_{LAI}$ isolate, and has the 36 amino acid sequence (reading from amino to carboxy terminus):

NH$_2$-YTSLIHSLIEESQNQQEKNEQELLELDK-WASLWNWF-COOH (SEQ ID NO:1)

In addition to the full-length DP178 36-mer, the peptides of this invention include truncations of the DP178 peptide comprising peptides of between 3 and 36 amino acid residues (i.e., peptides ranging in size from a tripeptide to a 36-mer polypeptide), These truncated peptides are shown in Tables 2 and 3.

In addition amino acid substitutions of the DP178 peptide are also within the scope of the invention. HIV-1 and HIV-2 enveloped proteins are structurally distinct, but there exists a striking amino acid conservation within the DP178-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the DP178 peptides of the invention. Utilizing the DP178 and DP178 analog sequences described herein, the skilled artisan can readily compile DP178 consensus sequences and ascertain from these, conserved amino acid residues which would represent preferred amino acid substitutions.

The amino acid substitutions may be of a conserved or non-conserved nature. Conserved amino acid substitutions consist of replacing one or more amino acids of the DP178 peptide sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the DP178 peptide sequence with amino acids possessing dissimilar charge, size, and/or hydrophobicity characteristics, such as, for example, a glutamic acid (E) to valine (V) substitution.

Amino acid insertions of DP178 may consist of single amino acid residues or stretches of residues. The insertions may be made at the carboxy or amino terminal end of the DP178 or DP178 truncated peptides, as well as at a position internal to the peptide.

Such insertions will generally range from 2 to 15 amino acids in length. It contemplated that insertions made at either the carboxy or amino terminus of the peptide of interest may be of a broader size range, with about 2 to about 50 amino acids being preferred. One or more such insertions may be introduced into DP178 or DP178 truncations, as long as such insertions result in peptides which may still be recognized by the 107×178×4, ALLMOTI5 or PLZIP search motifs described above.

Preferred amino or carboxy terminal insertions are peptides ranging from about 2 to about 50 amino acid residues in length, corresponding to gp41 protein regions either amino to or carboxy to the actual DP178 gp41 amino acid sequence, respectively. Thus, a preferred amino terminal or carboxy terminal amino acid insertion would contain gp41 amino acid sequences found immediately amino to or carboxy to the DP178 region of the gp41 protein.

Deletions of DP178 or DP178 truncations are also within the scope of this invention. Such deletions consist of the removal of one or more amino acids from the DP178 or DP178-like peptide sequence, with the lower limit length of the resulting peptide sequence being 4 to 6 amino acids.

Such deletions may involve a single contiguous or greater than one discrete portion of the peptide sequences. One or more such deletions may be introduced into DP178 or DP178 truncations, as long as such deletions result in peptides which may still be recognized by the 107×178×4, ALLMOTI5 or PLZIP search motifs described above.

B. DP107 Peptides

DP107 is a 38 amino acid peptide which exhibits potent antiviral activity, and corresponds to residues 558 to 595 of HIV-1$_{LAI}$ isolate transmembrane (TM) gp41 glycoprotein, as shown here:

NH$_2$-NNLLRAIEAQQHLLQLTVWQIKQLQA-RILAVERYLKDQ-COOH (SEQ ID NO:2)

In addition to the full-length DP107 38-mer, the DP107 peptides include truncations of the DP107 peptide comprising peptides of between 3 and 38 amino acid residues (i.e., peptides ranging in size from a tripeptide to a 38-mer polypeptide), These peptides are shown in Tables 4 and 5, below.

In addition, amino acid substitutions of the DP178 peptide are also within the scope of the invention. As for DP178, there also exists a striking amino acid conservation within the DP107-corresponding regions of HIV-1 and HIV-2, again of a periodic nature, suggesting conservation of structure and/or function. Therefore, one possible class of amino acid substitutions includes those amino acid changes predicted to stabilize the structure of the DP107 peptides of the invention. Utilizing the DP107 and DP107 analog sequences described herein, the skilled artisan can readily compile DP107 consensus sequences and ascertain from these, conserved amino acid residues which would represent preferred amino acid substitutions.

The amino acid substitutions may be of a conserved or non-conserved nature. Conserved amino acid substitutions consist of replacing one or more amino acids of the DP107 peptide sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the DP107 peptide sequence with amino acids possessing dissimilar charge, size, and/or hydrophobicity characteristics, such as, for example, a glutamic acid (E) to valine (V) substitution.

Amino acid insertions may consist of single amino acid residues or stretches of residues. The insertions may be made at the carboxy or amino terminal end of the DP107 or DP107 truncated peptides, as well as at a position internal to the peptide.

Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into DP107 or DP107 truncations, as long as such insertions result in peptides which may still be recognized by the 107×178×4, ALLMOTI5 or PLZIP search motifs described above.

Preferred amino or carboxy terminal insertions are peptides ranging from about 2 to about 50 amino acid residues in length, corresponding to gp41 protein regions either amino to or carboxy to the actual DP107 gp41 amino acid sequence, respectively. Thus, a preferred amino terminal or carboxy terminal amino acid insertion would contain gp41 amino acid sequences found immediately amino to or carboxy to the DP107 region of the gp41 protein.

Deletions of DP107 or DP107 truncations are also within the scope of this invention. Such deletions consist of the removal of one or more amino acids from the DP107 or DP107-like peptide sequence, with the lower limit length of the resulting peptide sequence being 4 to 6 amino acids.

Such deletions may involve a single contiguous or greater than one discrete portion of the peptide sequences. One or more such deletions may be introduced into DP107 or DP107 truncations, as long as such deletions result in peptides which may still be recognized by the 107×178×4, ALLMOTI5 or PLZIP search motifs.

DP107 and DP107 truncations are more fully described in U.S. Pat. No. 5,656,480, which is incorporated herein by reference in its entirety 2. DP107 and DP178 Analogs Peptides corresponding to analogs of the DP178, DP178 truncations, DP107 and DP107 truncation sequences of the invention, described, above, may be found in other viruses, including, for example, non-HIV-1 enveloped viruses, non-enveloped viruses and other non-viral organisms.

Such DP178 and DP107 analogs may, for example, correspond to peptide sequences present in transmembrane ("TM") proteins of enveloped viruses and may, correspond to peptide sequences present in non enveloped and nonviral organisms. Such peptides may exhibit antifusogenic activity, antiviral activity, most particularly antiviral activity which is specific to the virus in which their native sequences are found, or may exhibit an ability to modulate intracellular processes involving coiled-coil peptide structures.

A. DP178 Analogs

DP178 analogs are peptides whose amino acid sequences are comprised of the amino acid sequences of peptide regions of, for example, other (i.e., other than HIV-1) viruses that correspond to the gp41 peptide region from which DP178 was derived. Such viruses may include, but are not limited to, other HIV-1 isolates and HIV-2 isolates.

DP178 analogs derived from the corresponding gp41 peptide region of other (i.e., non HIV-1LAI) HIV-1 isolates may include, for example, peptide sequences as shown below.

$NH_2$-YTNTIYTLLEESQNQQEKNEQELLELDK-WASLWNWF-COOH (SEQ ID NO:3)

$NH_2$-YTGIIYNLLEESQNQQEKNEQELLELDK-WANLWNWF-COOH (SEQ ID NO:4)

$NH_2$-YTSLIYSLLEKSQIQQEKNEQELLELDK-WASLWNWF-COOH(SEQ ID NO:5)

The peptides of SEQ ID NO:3, SEQ ID NO:4 and SEQ ID NO:5 are derived from HIV-1$_{SF2}$, HIV-1$_{RF}$, and HIV-1$_{MN}$, respectively. Other DP178 analogs include those derived from HIV-2, including the peptides of SEQ ID NO:6 and SEQ ID NO:7, which are derived from HIV-2$_{ROD}$ and HIV-2$_{NIHZ}$, respectively. Still other useful analogs include the peptides of SEQ ID NO:8 and SEQ ID NO:9, which have been demonstrated to exhibit anti-viral activity.

In the present invention, it is preferred that the DP178 analogs represent peptides whose amino acid sequences correspond to the DP178 region of the gp41 protein, it is also contemplated that the peptides disclosed herein may, additionally, include amino acid sequences, ranging from about 2 to about 50 amino acid residues in length, corresponding to gp41 protein regions either amino to or carboxy to the actual DP178 amino acid sequence.

Table 6 and Table 7 show some possible truncations of the HIV-2$_{NIHZ}$ DP178 analog, which may comprise peptides of between 3 and 36 amino acid residues (i.e., peptides ranging in size from a tripeptide to a 36-mer polypeptide). Peptide sequences in these tables are listed from amino (left) to carboxy (right) terminus.

B. Additional DP178 Analogs and DP107 Analogs

DP178 and DP107 analogs are recognized or identified, for example, by utilizing one or more of the 107×178×4, ALLMOTI5 or PLZIP computer-assisted search strategies described above. The search strategy identifies additional peptide regions which are predicted to have structural and/or amino acid sequence features similar to those of DP107 and/or DP178.

The search strategies are described fully in the example presented in Section 9 of U.S. Pat. Nos. 6,013,263, 6,017,536 and 6,020,459. While this search strategy is based, in part, on a primary amino acid motif deduced from DP107 and DP178, it is not based solely on searching for primary amino acid sequence homologies, as such protein sequence homologies exist within, but not between major groups of viruses. For example, primary amino acid sequence homology is high within the TM protein of different strains of HIV-1 or within the TM protein of different isolates of simian immunodeficiency virus (SIV).

The computer search strategy disclosed in U.S. Pat. Nos. 6,013,263, 6,017,536 and 6,020,459 successfully identified regions of proteins similar to DP107 or DP 178. This search strategy was designed to be used with a commercially-available sequence database package, preferably PC/Gene.

In U.S. Pat. Nos. 6,013,263, 6,017,536 and 6,020,459, a series of se arch motifs, the 107×178×4, ALLMOTI5 and PLZIP motifs, were designed and engineered to range in stringency from strict to broad, with 107×178×4 being preferred. The sequences identified via such search motifs, such as those listed in Tables V-XIV, of U.S. Pat. Nos. 6,013,263, 6,017,536 and 6,020,459 and included in this application by incorporation by reference, potentially exhibit antifusogenic, such as antiviral, activity, may additionally be useful in the identification of antifusogenic, such as antiviral, compounds.

3. Other Anti-Viral Peptides

A. Anti-RSV Peptides

Anti-RSV peptides include DP178 and/or DP107 analogs identified from corresponding peptide sequences in RSV which have further been identified to inhibit viral infection by RSV. Such peptides of interest include the peptides of Table 16 and peptides of SEQ ID NO:10 to SEQ ID NO: 30. Of particular interest are the following peptides:

YTSVITIELSNIKENKCNGAKVKLIKQELDKYK (SEQ ID NO:14)

TSVITIELSNIKENKCNGAKVKLIKQELDKYKN (SEQ ID NO:15)

VITIELSNIKENKCNGAKVKLIKQELDKYKNAV (SEQ ID NO:16)

IALLSTNKAVVSLSNGVSVLTSKVLDLKNYIDK (SEQ ID NO:29)

The peptide of SEQ ID NO:10 is derived from the F2 region of RSV and was identified in U.S. Pat. Nos. 6,103,236 and 6,020,459 using the search motifs described as corresponding to DP107 and DP178 peptides (i.e., "DP107/178 like"). The peptides of SEQ ID NO:14 to SEQ ID NO:16 each have amino acid sequences contained within the peptide of SEQ ID NO:10 and each has been shown to exhibit anti-RSV activity, in particular, inhibiting fusion and syncytia formation between RSV-infected and uninfected Hep-2 cells at concentrations of less than 50 µg/ml.

The peptide of SEQ ID NO:11 is derived from the F1 region of RSV and was identified in U.S. Pat. Nos. 6,103,236 and 6,020,459 using the search motifs described as corresponding to DP107 (i.e., "DP107-like"). The peptide of SEQ ID NO:29 contains amino acid sequences contained within the peptide of SEQ ID NO:10 and likewise has been shown to exhibit anti-RSV activity, in particular, inhibiting fusion and syncytia formation between RSV-infected and uninfected Hep-2 cells at concentrations of less than 50 µg/ml.

B. Anti-HPIV Peptides

Anti-HPIV peptides include DP178 and/or DP107 analogs identified from corresponding peptide sequences in HPIV and which have further been identified to inhibit viral infection by HPIV. Such peptides of interest include the peptides of Table 17 and SEQ ID NO:31 to SEQ ID NO:62. Of particular interest are the following peptides:

VEAKQARSDIEKLKEAIRDTNKAVQSVQSSIGNLI (SEQ ID NO:52)
RSDIEKLKEAIRDTNKAVQSVQSSIGNLIVAIKSV (SEQ ID NO:58)
NSVALDPIDISIELNKAKSDLEESKEWIRRSNQKL (SEQ ID NO:35)
ALDPIDISIELNKAKSDLEESKEWIRRSNQKLDSI (SEQ ID NO:38)
LDPIDISIELNKAKSDLEESKEWIRRSNQKLDSIG (SEQ ID NO:39)
DPIDISIELNKAKSDLEESKEWIRRSNQKLDSIGN (SEQ ID NO:40)

PIDISIELNKAKSDLEESKEWIRRSNQKLDSIGNW (SEQ ID NO:41)

IDISIELNKAKSDLEESKEWIRRSNQKLDSIGNWH (SEQ ID NO:42)

The peptide of SEQ ID NO:31 is derived from the F1 region of HPIV-3 and was identified in U.S. Pat. Nos. 6,103,236 and 6,020,459 using the search motifs described as corresponding to DP107 (i.e., "DP107-like"). The peptides of SEQ ID NO:52 and SEQ ID NO:58 each have amino acid sequences contained within the peptide of SEQ ID NO:31 and each has been shown to exhibit anti-HPIV-3 activity, in particular, inhibiting fusion and syncytia formation between HPIV-3-infected Hep2 cells and uninfected CV-1W cells at concentrations of less than 1 μg/ml.

The peptide of SEQ ID NO:32 is also derived from the F1 region of HPIV-3 and was identified in U.S. Pat. Nos. 6,103,236 and 6,020,459 using the search motifs described as corresponding to DP178 (i.e., "DP178-like"). The peptides of SEQ ID NO:35 and SEQ ID NO:38 to SEQ ID NO:42 each have amino acid sequences contained within the peptide of SEQ ID NO:32 and each also has been shown to exhibit anti-HPIV-3 activity, in particular, inhibiting fusion and syncytia formation between HPIV-3-infected Hep2 cells and uninfected CV-1W cells at concentrations of less than 1 μg/ml.

C. Anti-MeV Peptides

Anti-MeV peptides are DP178 and/or DP107 analogs identified from corresponding peptide sequences in measles virus (MeV) which have further been identified to inhibit viral infection by the measles virus. Such peptides of particular interest include the peptides of Table 19 and peptides of SEQ ID NO:74 to SEQ ID NO:86. Of particular interest are the peptides listed below.

HRIDLGPPISLERLDVGTNLGNAIAKLEAKELLE (SEQ ID NO:77)

IDLGPPISLERLDVGTNLGNAIAKLEAKELLESS (SEQ ID NO:79)

LGPPISLERLDVGTNLGNAIAKLEAKELLESSDQ (SEQ ID NO:81)

PISLERLDVGTNLGNAIAKLEAKELLESSDQILR (SEQ ID NO:84)

Sequences derived from measles virus were identified in U.S. Pat. Nos. 6,103,236 and 6,020,459 using the search motifs described as corresponding to DP178 (i.e., "DP178-like"). The peptides of SEQ ID NO:77, SEQ ID NO:79, SEQ ID NO:81 and SEQ ID NO:83 each have amino acid sequences so identified, and each has been shown to exhibit anti-MeV activity, in particular, inhibiting fusion and syncytia formation between MeV-infected Hep2 and uninfected Vero cells at concentrations of less than 1 μg/ml.

D. Anti-SIV Peptides

Anti-SIV peptides are DP178 and/or DP107 analogs identified from corresponding peptide sequences in SIV which have further been identified to inhibit viral infection by SIV. Such peptides of interest include the peptides of Table 18 and peptides of SEQ ID NO:63 to SEQ ID NO:73. Of particular interest are the following peptides:

WQEWERKVDFLEENITALLEEA-QIQQEKNMYELQK (SEQ ID NO:64)

QEWERKVDFLEENITALLEEAQIQQEKNMYELQKL (SEQ ID NO:65)

EWERKVDFLEENITALLEEAQIQQEKNMYELQKLN (SEQ ID NO:66)

WERKVDFLEENITALLEEAQIQQEKNMYELQKLNS (SEQ ID NO:67)

ERKVDFLEENITALLEEAQIQQEKNMYELQKLNSW (SEQ ID NO:68)

RKVDFLEENITALLEEAQIQQEKNMY-ELQKLNSWD (SEQ ID NO:69)

KVDFLEENITALLEEAQIQQEKNMY-ELQKLNSWDV (SEQ ID NO:70)

VDFLEENITALLEEAQIQQEKNMYELQKLNSWDVF (SEQ ID NO:71)

DFLEENITALLEEAQIQQEKNMYELQKLNSWDVFG (SEQ ID NO:72)

FLEENITALLEEAQIQQEKNMYELQKLNSWDVFGN (SEQ ID NO:73)

Sequences derived from SIV transmembrane fusion protein were identified in U.S. Pat. Nos. 6,103,236 and 6,020,459 using the search motifs described as corresponding to DP178 (i.e., "DP178-like"). The peptides of SEQ ID NO:64 to SEQ ID NO:73 each have amino acid sequences so identified, and each has been shown to exhibit potent anti-SIV activity as crude peptides.

4. Modification of Anti-Viral and Antifusogenic Peptides

The invention contemplates modifying peptides that exhibit anti-viral and/or antifusogenic activity, including such modifications of DP-107 and DP-178 and analogs thereof. Such modified peptides can react with the available reactive functionalities on blood components via covalent linkages. The invention also relates to such modifications, such combinations with blood components, and methods for their use. These methods include extending the effective therapeutic life of the conjugated anti-viral peptides derivatives as compared to administration of the unconjugated peptides to a patient. The modified peptides are of a type designated as a DAC (Drug Affinity Complex) which comprises the anti-viral peptide molecule and a linking group together with a chemically reactive group capable of reaction with a reactive functionality of a mobile blood protein. By reaction with the blood component or protein the modified peptide, or DAC, may be delivered via the blood to appropriate sites or receptors.

To form covalent bonds with functionalities on the protein, one may use as a reactive group a wide variety of active carboxyl groups, particularly esters, where the hydroxyl moiety is physiologically acceptable at the levels required to modify the peptide. While a number of different hydroxyl groups may be employed in these reactive groups, the most convenient would be N-hydroxysuccinimide or (NHS), N-hydroxy-sulfosuccinimide (sulfo-NHS). In preferred embodiments of this invention, the functionality on the protein will be a thiol group and the reactive group will be a maleimido-containing group such as gamma-maleimide-butyralamide (GMBA) or maleimidopropionic acid (MPA)

Primary amines are the principal targets for NHS esters. Accessible α-amine groups present on the N-termini of proteins react with NHS esters. However, α-amino groups on a protein may not be desirable or available for the NHS coupling. While five amino acids have nitrogen in their side chains, only the ε-amine of lysine reacts significantly with NHS esters. An amide bond is formed when the NHS ester conjugation reaction reacts with primary amines releasing N-hydroxysuccinimide as demonstrated in the schematic below.

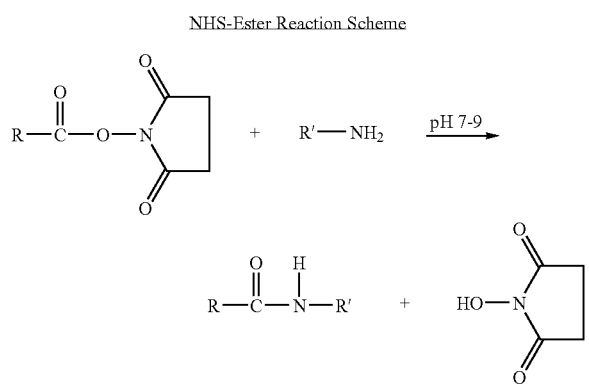

NHS-Ester Reaction Scheme

In the preferred embodiments of this invention, the functional group on this protein will be a thiol group and the chemically reactive group will be a maleimido-containing group such as MPA or GMBA (gamma-maleimide-butyralamide). The maleimido group is most selective for sulfhydryl groups on peptides when the pH of the reaction mixture is kept between 6.5 and 7.4. At pH 7.0, the rate of reaction of maleimido groups with sulfhydryls is 1000-fold faster than with amines. A stable thioether linkage between the maleimido group and the sulfhydryl is formed which cannot be cleaved under physiological conditions, as demonstrated in the following schematic.

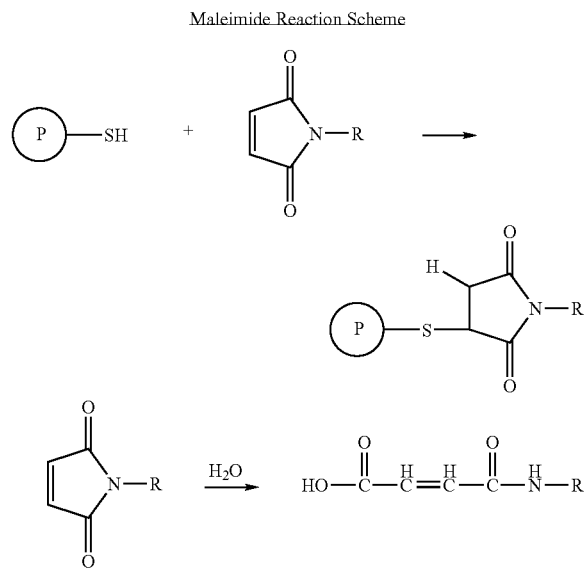

Maleimide Reaction Scheme

A. Specific Labeling.

Preferably, the modified peptides of this invention are designed to specifically react with thiol groups on mobile blood proteins. Such reaction is preferably established by covalent bonding of the peptide modified with a maleimide link (e.g. prepared from GMBS, MPA or other maleimides) to a thiol group on a mobile blood protein such as serum albumin or IgG.

Under certain circumstances, specific labeling with maleimides offers several advantages over non-specific labeling of mobile proteins with groups such as NHS and sulfo-NHS. Thiol groups are less abundant in vivo than amino groups. Therefore, the maleimide-modified peptides of this invention, i.e., maleimide peptides, will covalently bond to fewer proteins. For example, in albumin (the most abundant blood protein) there is only a single thiol group. Thus, peptide-maleimide-albumin conjugates will tend to comprise approximately a 1:1 molar ratio of peptide to albumin. In addition to albumin, IgG molecules (class II) also have free thiols. Since IgG molecules and serum albumin make up the majority of the soluble protein in blood they also make up the majority of the free thiol groups in blood that are available to covalently bond to maleimide-modified peptides.

Further, even among free thiol-containing blood proteins, including IgGs, specific labeling with maleimides leads to the preferential formation of peptide-maleimide-albumin conjugates, due to the unique characteristics of albumin itself. The single free thiol group of albumin, highly conserved among species, is located at amino acid residue 34 ($Cys^{34}$). It has been demonstrated recently that the $Cys^{34}$ of albumin has increased reactivity relative to free thiols on other free thiol-containing proteins. This is due in part to the very low pK value of 5.5 for the $Cys^{34}$ of albumin. This is much lower than typical pK values for cysteine residues in general, which are typically about 8. Due to this low pK, under normal physiological conditions $Cys^{34}$ of albumin is predominantly in the ionized form, which dramatically increases its reactivity. In addition to the low pK value of $Cys^{34}$, another factor which enhances the reactivity of $Cys^{34}$ is its location, which is in a crevice close to the surface of one loop of region V of albumin. This location makes $Cys^{34}$ very available to ligands of all kinds, and is an important factor in $Cys^{34}$'s biological role as free radical trap and free thiol scavenger. These properties make $Cys^{34}$ highly reactive with maleimide-peptides, and the reaction rate acceleration can be as much as 1000-fold relative to rates of reaction of maleimide-peptides with other free-thiol containing proteins.

Another advantage of peptide-maleimide-albumin conjugates is the reproducibility associated with the 1:1 loading of peptide to albumin specifically at $Cys^{34}$. Other techniques, such as glutaraldehyde, DCC, EDC and other chemical activations of, e.g, free amines, lack this selectivity. For example, albumin contains 52 lysine residues, 25-30 of which are located on the surface of albumin and therefore accessible for conjugation. Activating these lysine residues, or alternatively modifying peptides to couple through these lysine residues, results in a heterogenous population of conjugates. Even if 1:1 molar ratios of peptide to albumin are employed, the yield will consist of multiple conjugation products, some containing 0, 1, 2 or more peptides per albumin, and each having peptides randomly coupled at any one or more of the 25-30 available lysine sites. Given the numerous possible combinations, characterization of the exact composition and nature of each conjugate batch becomes difficult, and batch-to-batch reproducibility is all but impossible, making such conjugates less desirable as a therapeutic. Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al., "The Loading Rate Determines Tumor Targeting properties of Methotrexate-Albumin Conjugates in Rats," *Anti-Cancer Drugs*, Vol. 8, pp. 677-685 (1988), incorporated herein in its entirety, the authors report that a 1:1 ratio of the anti-cancer methotrexate to albumin conjugated via glutaraldehyde gave the most promising results. These conjugates were preferentially taken up by tumor cells, whereas conjugates bearing 5:1 to 20:1 methotrexate molecules had altered HPLC profiles and were quickly taken up by the liver in vivo. It is postulated that at these higher ratios, conformational changes to albumin diminish its effectiveness as a therapeutic carrier.

Through controlled administration of maleimide-peptides in vivo, one can control the specific labeling of albumin and IgG in vivo. In typical administrations, 80-90% of the administered maleimide-peptides will label albumin and less than 5% will label IgG. Trace labeling of free thiols such as glutathione will also occur. Such specific labeling is preferred for in vivo use as it permits an accurate calculation of the estimated half-life of the administered agent.

In addition to providing controlled specific in vivo labeling, maleimide-peptides can provide specific labeling of serum albumin and IgG ex vivo. Such ex vivo labeling involves the addition of maleimide-peptides to blood, serum or saline solution containing serum albumin and/or IgG. Once conjugation has occurred ex vivo with the maleimide-peptides, the blood, serum or saline solution can be readministered to the patient's blood for in vivo treatment.

In contrast to NHS-peptides, maleimide-peptides are generally quite stable in the presence of aqueous solutions and in the presence of free amines. Since maleimide-peptides will only react with free thiols, protective groups are generally not necessary to prevent the maleimide-peptides from reacting with itself. In addition, the increased stability of the modified peptide permits the use of further purification steps such as HPLC to prepare highly purified products suitable for in vivo use. Lastly, the increased chemical stability provides a product with a longer shelf life.

B. Non-Specific Labeling.

The anti-viral peptides of the invention may also be modified for non-specific labeling of blood components. Bonds to amino groups will also be employed, particularly with the formation of amide bonds for non-specific labeling. To form such bonds, one may use as a chemically reactive group a wide variety of active carboxyl groups, particularly esters, where the hydroxyl moiety is physiologically acceptable at the levels required. While a number of different hydroxyl groups may be employed in these linking agents, the most convenient would be N-hydroxysuccinimide (NHS) and N-hydroxy-sulfosuccinimide (sulfo-NHS).

Other linking agents which may be utilized are described in U.S. Pat. No. 5,612,034, which is hereby incorporated herein.

The various sites with which the chemically reactive group of the modified peptides may react in vivo include cells, particularly red blood cells (erythrocytes) and platelets, and proteins, such as immunoglobulins, including IgG and IgM, serum albumin, ferritin, steroid binding proteins, transferrin, thyroxin binding protein, $\alpha$-2-macroglobulin, and the like. Those receptors with which the modified peptides react, which are not long-lived, will generally be eliminated from the human host within about three days. The proteins indicated above (including the proteins of the cells) will remain at least three days, and may remain five days or more (usually not exceeding 60 days, more usually not exceeding 30 days) particularly as to the half life, based on the concentration in the blood.

For the most part, reaction will be with mobile components in the blood, particularly blood proteins and cells, more particularly blood proteins and erythrocytes. By "mobile" is intended that the component does not have a fixed situs for any extended period of time, generally not exceeding 5 minutes, more usually one minute, although some of the blood component may be relatively stationary for extended periods of time. Initially, there will be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

The desired conjugates of non-specific modified peptides to blood components may be prepared in vivo by administration of the modified peptides to the patient, which may be a human or other mammal. The administration may be done in the form of a bolus or introduced slowly over time by infusion using metered flow or the like.

If desired, the subject conjugates may also be prepared ex vivo by combining blood with modified peptides of the present invention, allowing covalent bonding of the modified peptides to reactive functionalities on blood components and then returning or administering the conjugated blood to the host. Moreover, the above may also be accomplished by first purifying an individual blood component or limited number of components, such as red blood cells, immunoglobulins, serum albumin, or the like, and combining the component or components ex vivo with the chemically reactive modified peptides. The functionalized blood or blood component may then be returned to the host to provide in vivo the subject therapeutically effective conjugates. The blood also may be treated to prevent coagulation during handling ex vivo.

5. Synthesis of Modified Anti-Viral and Anti-Fusogenic Peptides

A. Peptide Synthesis

Anti-viral and/or anti-fusogenic peptides according to the present invention may be synthesized by standard methods of solid phase peptide chemistry known to those of ordinary skill in the art. For example, peptides may be synthesized by solid phase chemistry techniques following the procedures described by Steward and Young (Steward, J. M. and Young, J. D., Solid Phase Peptide Synthesis, 2nd Ed., Pierce Chemical Company, Rockford, Ill., (1984) using an Applied Biosystem synthesizer. Similarly, multiple peptide fragments may be synthesized then linked together to form larger peptides. These synthetic peptides can also be made with amino acid substitutions at specific locations.

For solid phase peptide synthesis, a summary of the many techniques may be found in J. M. Stewart and J. D. Young, Solid Phase Peptide Synthesis, W.H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, Vol. 1, Academic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α, α-dimethyl-3,5-dimethoxybenzyloxycarbonyl, o-nitrophenylsulfenyl, 2-cyano-t-butyloxycarbonyl, and the like. The 9-fluorenyl-methyloxycarbonyl (Fmoc) protecting group is particularly preferred for the synthesis of the peptides of the present invention. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzenesulfonyl, Cbz, Boc, and adamantyloxycarbonyl; for tyrosine, benzyl, o-bromobenzyloxycarbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of α-C-terminal carboxy peptides is 4-hydroxymethylphenoxymethyl-copoly(styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours at a temperature of between 10° and 50° C. in a solvent such as dichloromethane or DMF.

When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. The preferred method for coupling to the deprotected 4-(2',4'-dimethoxyphenyl-Fmoc-aminomethyl)phenoxy-acetamidoethyl resin is O-benzotriazol-1-yl-N,N,N',N'-tetramethyluroniumhexafluoro-phosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art. In a preferred embodiment, the α-N-terminal amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluorophosphate (HBTU, 1 equiv.) and 1-hydroxybenzotriazole (HOBT, 1 equiv.).

At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thioanisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide is purified by a sequence of chromatographic steps employing any or all of the following types: ion exchange on a weakly basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilylsilica bonded phase column packing.

Molecular weights of these ITPs are determined using Fast Atom Bombardment (FAB) Mass Spectroscopy.

(1) N-Terminal Protective Groups

As discussed above, the term "N-protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene, "Protective Groups In Organic Synthesis," (John Wiley & Sons, New York (1981)), which is hereby incorporated by reference. Additionally, protecting groups can be used as pro-drugs which are readily cleaved in vivo, for example, by enzymatic hydrolysis, to release the biologically active parent. α-N-protecting groups comprise loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like.

(2) Carboxy Protective Groups

As discussed above, the term "carboxy protecting group" refers to a carboxylic acid protecting ester or amide group employed to block or protect the carboxylic acid functionality while the reactions involving other functional sites of the compound are performed. Carboxy protecting groups are disclosed in Greene, "Protective Groups in Organic Synthesis" pp. 152-186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$-$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

Representative amide carboxy protecting groups are aminocarbonyl and loweralkylaminocarbonyl groups.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester. Preferred amide carboxy protecting groups are loweralkylaminocarbonyl groups. For example, aspartic acid may be protected at the α-C-terminal by an acid labile group (e.g. t-butyl) and protected at the β-C-terminal by a hydrogenation labile group (e.g. benzyl) then deprotected selectively during synthesis.

B. Peptide Modification

The manner of producing the modified peptides of the present invention will vary widely, depending upon the nature of the various elements comprising the peptide. The synthetic procedures will be selected so as to be simple, provide for high yields, and allow for a highly purified stable product. Normally, the chemically reactive group will be created at the last stage of the synthesis, for example, with a carboxyl group, esterification to form an active ester. Specific methods for the production of modified peptides of the present invention are described below.

Specifically, the selected peptide is first assayed for anti-viral activity, and then is modified with the linking group only at either the N-terminus, C-terminus or interior of the peptide. The anti-viral activity of this modified peptide-linking group is then assayed. If the anti-viral activity is not reduced dramatically (i.e., reduced less than 10-fold), then the stability of the modified peptide-linking group is measured by its in vivo lifetime. If the stability is not improved to a desired level, then the peptide is modified at an alternative site, and the procedure is repeated until a desired level of anti-viral and stability is achieved.

More specifically, each peptide selected to undergo modification with a linker and a reactive entity group will be modified according to the following criteria: if a terminal carboxylic group is available on the peptide and is not critical for the retention of anti-viral activity, and no other sensitive functional group is present on the peptide, then the carboxylic acid will be chosen as attachment point for the linker-reactive group modification. If the terminal carboxylic group is involved in anti-viral activity, or if no carboxylic acids are available, then any other sensitive functional group not critical for the retention of anti-viral activity will be selected as the attachment point for the linker-reactive entity modification. If several sensitive functional groups are available on a peptide, a combination of protecting groups will be used in such a way that after addition of the linker/reactive entity and deprotection of all the protected sensitive functional groups, retention of anti-viral activity is still obtained. If no sensitive functional groups are available on the peptide, or if a simpler modification route is desired, synthetic efforts will allow for a modification of the original peptide in such a way that retention of anti-viral is maintained. In this case the modification will occur at the opposite end of the peptide An NHS derivative may be synthesized from a carboxylic acid in absence of other sensitive functional groups in the peptide. Specifically, such a peptide is reacted with N-hydroxysuccinimide in anhydrous $CH_2Cl_2$ and EDC, and the product is purified by chromatography or recrystallized from the appropriate solvent system to give the NHS derivative.

Alternatively, an NHS derivative may be synthesized from a peptide that contains an amino and/or thiol group and a carboxylic acid. When a free amino or thiol group is present in the molecule, it is preferable to protect these sensitive functional groups prior to perform the addition of the NHS derivative. For instance, if the molecule contains a free amino group, a transformation of the amine into a Fmoc or preferably into a tBoc protected amine is necessary prior to perform the chemistry described above. The amine functionality will not be deprotected after preparation of the NHS derivative. Therefore this method applies only to a compound whose amine group is not required to be freed to induce the desired anti-viral effect. If the amino group needs to be freed to retain the original properties of the molecule, then another type of chemistry described below has to be performed.

In addition, an NHS derivative may be synthesized from a peptide containing an amino or a thiol group and no carboxylic acid. When the selected molecule contains no carboxylic acid, an array of bifunctional linkers can be used to convert the molecule into a reactive NHS derivative. For instance, ethylene glycol-bis(succinimydylsuccinate) (EGS) and triethylamine dissolved in DMF and added to the free amino containing molecule (with a ratio of 10:1 in favor of EGS) will produce the mono NHS derivative. To produce an NHS derivative from a thiol derivatized molecule, one can use N-[-maleimidobutyryloxy]succinimide ester (GMBS) and triethylamine in DMF. The maleimido group will react with the free thiol and the NHS derivative will be purified from the reaction mixture by chromatography on silica or by HPLC.

An NHS derivative may also be synthesized from a peptide containing multiple sensitive functional groups. Each case will have to be analyzed and solved in a different manner. However, thanks to the large array of protecting groups and bifunctional linkers that are commercially available, this invention is applicable to any peptide with preferably one chemical step only to modify the peptide (as described above) or two steps (as described above involving prior protection of a sensitive group) or three steps (protection, activation and deprotection). Under exceptional circumstances only, would multiple steps (beyond three steps) synthesis be required to transform a peptide into an active NHS or maleimide derivative.

A maleimide derivative may also be synthesized from a peptide containing a free amino group and a free carboxylic acid. To produce a maleimide derivative from a amino derivatized molecule, one can use N-[γ-maleimidobutyryloxy]succinimide ester (GMBS) and triethylamine in DMF. The succinimide ester group will react with the free amino and the maleimide derivative will be purified from the reaction mixture by crystallization or by chromatography on silica or by HPLC.

Finally, a maleimide derivative may be synthesized from a peptide containing multiple other sensitive functional groups and no free carboxylic acids. When the selected molecule contains no carboxylic acid, an array of bifunctional crosslinking reagents can be used to convert the molecule into a reactive NHS derivative. For instance maleimidopropionic acid (MPA) can be coupled to the free amine to produce a maleimide derivative through reaction of the free amine with the carboxylic group of MPA using HBTU/HOBt/DIEA activation in DMF.

Many other commercially available heterobifunctional crosslinking reagents can alternatively be used when needed. A large number of bifunctional compounds are available for linking to entities. Illustrative reagents include: azidobenzoyl hydrazide, N-[4-(p-azidosalicylamino)butyl]-3'-[2'-pyridyldithio)propionamide), bis-sulfosuccinimidyl suberate, dimethyl adipimidate, disuccinimidyl tartrate, N-y-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl 4-[N-maleimidomethyl]cyclohexane-1-carboxylate.

6. Uses of Modified Anti-Viral Peptides

Modified anti-viral peptides of the invention may be used as a therapeutic agent in the treatment of patients who are suffering from viral infection, and can be administered to patients according to the methods described below and other methods known in the art. Effective therapeutic dosages of the modified peptides may be determined through procedures well known by those in the art and will take into consideration any concerns over potential toxicity of the peptide.

The modified peptides can also be administered prophylactically to previously uninfected individuals. This can be advantageous in cases where an individual has been subjected to a high risk of exposure to a virus, as can occur when individual has been in contact with an infected individual where there is a high risk of viral transmission. This can be especially advantageous where there is known cure for the virus, such as the HIV virus. As a example, prophylactic administration of a modified anti-HIV peptide would be advantageous in a situation where a health care worker has been exposed to blood from an HIV-infected individual, or in other situations where an individual engaged in high-risk activities that potentially expose that individual to the HIV virus.

7. Administration of Modified Anti-Viral and Anti-Fusogenic Peptides

Generally, the modified peptides will be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The subject modified peptides will for the most part be administered parenterally, such as intravenously (IV), intraarterially (IA), intramuscularly (IM), subcutaneously (SC), or the like. Administration may in appropriate situations be by transfusion. In some instances, where reaction of the functional group is relatively slow, administration may be oral, nasal, rectal, transdermal or aerosol, where the nature of the conjugate allows for transfer to the vascular system. Usually a single injection will be employed although more than one injection may be used, if desired. The modified peptides may be administered by any convenient means, including syringe, trocar, catheter, or the like.

The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the modified peptide be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

By bonding to long-lived components of the blood, such as immunoglobulin, serum albumin, red blood cells and platelets, a number of advantages ensue. The activity of the peptide is extended for days to weeks. Only one administration need be given during this period of time. Greater specificity can be achieved, since the active compound will be primarily bound to large molecules, where it is less likely to be taken up intracellularly to interfere with other physiological processes.

8. Monitoring the Presence of Modified Peptides

The blood of the mammalian host may be monitored for the presence of the modified peptide compound one or more times. By taking a portion or sample of the blood of the host, one may determine whether the peptide has become bound to the long-lived blood components in sufficient amount to be therapeutically active and, thereafter, the level of the peptide compound in the blood. If desired, one may also determine to which of the blood components the peptide is bound. This is particularly important when using non-specific modified peptides. For specific maleimide-modified peptides, it is much simpler to calculate the half life of serum albumin and IgG.

A. Immuno Assays

Another aspect of this invention relates to methods for determining the concentration of the anti-viral peptides and/or analogs, or their derivatives and conjugates in biological samples (such as blood) using antibodies specific for the peptides, peptide analogs or their derivatives and conjugates, and to the use of such antibodies as a treatment for toxicity potentially associated with such peptides, analogs, and/or their derivatives or conjugates. This is advantageous because the increased stability and life of the peptides in vivo in the patient might lead to novel problems during treatment, including increased possibility for toxicity.

The use of anti-therapeutic agent antibodies, either monoclonal or polyclonal, having specificity for a particular peptide, peptide analog or derivative thereof, can assist in mediating any such problem. The antibody may be generated or derived from a host immunized with the particular peptide, analog or derivative thereof, or with an immunogenic fragment of the agent, or a synthesized immunogen corresponding to an antigenic determinant of the agent. Preferred antibodies will have high specificity and affinity for native, modified and conjugated forms of the peptide, peptide analog or derivative. Such antibodies can also be labeled with enzymes, fluorochromes, or radiolabels.

Antibodies specific for modified peptides may be produced by using purified peptides for the induction of peptide-specific antibodies. By induction of antibodies, it is intended not only the stimulation of an immune response by injection into animals, but analogous steps in the production of synthetic antibodies or other specific binding molecules such as screening of recombinant immunoglobulin libraries. Both monoclonal and polyclonal antibodies can be produced by procedures well known in the art.

The anti-peptide antibodies may be used to treat toxicity induced by administration of the modified peptide, analog or derivative thereof, and may be used ex vivo or in vivo. Ex vivo methods would include immuno-dialysis treatment for toxicity employing anti-therapeutic agent antibodies fixed to solid supports. In vivo methods include administration of anti-therapeutic agent antibodies in amounts effective to induce clearance of antibody-agent complexes.

The antibodies may be used to remove the modified peptides, analogs or derivatives thereof, and conjugates thereof, from a patient's blood ex vivo by contacting the blood with the antibodies under sterile conditions. For example, the antibodies can be fixed or otherwise immobilized on a column matrix and the patient's blood can be removed from the patient and passed over the matrix. The modified peptide, peptide analogs, derivatives or conjugates will bind to the antibodies and the blood containing a low concentration of peptide, analog, derivative or conjugate, then may be returned to the patient's circulatory system. The amount of peptide compound removed can be controlled by adjusting the pressure and flow rate.

Preferential removal of the peptides, analogs, derivatives and conjugates from the plasma component of a patient's blood can be effected, for example, by the use of a semipermeable membrane, or by otherwise first separating the plasma component from the cellular component by ways known in the art prior to passing the plasma component over a matrix containing the anti-therapeutic antibodies. Alternatively the preferential removal of peptide-conjugated blood cells, including red blood cells, can be effected by collecting and concentrating the blood cells in the patient's blood and contacting those cells with fixed anti-therapeutic antibodies to the exclusion of the serum component of the patient's blood.

The anti-therapeutic antibodies can be administered in vivo, parenterally, to a patient that has received the peptide, analogs, derivatives or conjugates for treatment. The antibodies will bind peptide compounds and conjugates. Once bound the peptide activity will be hindered if not completely blocked thereby reducing the biologically effective concentration of peptide compound in the patient's bloodstream and minimizing harmful side effects. In addition, the bound antibody-peptide complex will facilitate clearance of the peptide compounds and conjugates from the patient's blood stream.

The invention having been fully described can be further appreciated and understood with reference to the following non-limiting examples.

Example 1

Preparation of a Modified DP178

Synthesis of YTSLIHSLIEESQNQQEKNEQEL-LELDKWASLWNWFK(MPA)-NH$_2$

In this example, DP178 (SEQ ID NO:1) is synthesized and modified to include a linker and maleimide group according to the following synthesis scheme. As reported in U.S. Pat. Nos. 6,013,236 and 6,020,459, DP178 is a potent inhibitor of HIV-1, and inhibits both cell-induced syncytia formation between HIV-1 infected and uninfected cells and infection of uninfected cells be cell-free HIV-1 virus.

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Phe-OH, Fmoc-Trp(Boc)-OH, Fmoc-Asn(Trt)-OH, Fmoc-Trp(Boc)-OH, Fmoc-Leu-OH, Fmoc-Ser(tBu)-OH, Fmoc-Ala-OH, Fmoc-Trp(Boc)-OH, Fmoc-Lys(Boc)-OH, Fmoc-Asp(tBu)-OH, Fmoc-Leu-OH, Fmoc-Glu(tBu)-OH, Fmoc-Leu-OH, Fmoc-Leu-OH, Fmoc-Glu(tBu)-OH, Fmoc-Gln(Trt)-OH, Fmoc-Glu(tBu)-OH, Fmoc-Met-OH, Fmoc-Lys(Boc)-OH, Fmoc-Glu(tBu)-OH, Fmoc-Gln(Trt)-OH, Fmoc-Asn(Trt)-OH, Fmoc-Lys(Boc)-OH, Fmoc-Glu(tBu)-OH; Fmoc-Gln(Trt)-OH, Fmoc-Gln(Trt)-OH, Fmoc-Asn(Trt)-OH, Fmoc-Gln(Trt)-OH, Fmoc-Ser(tBu)-OH, Fmoc-Glu(tBu)-OH, Fmoc-Glu(tBu)-OH, Fmoc-Ile-OH, Fmoc-Leu-OH, Fmoc-Ser(tBu)-OH, Fmoc-His(Boc)-OH, Fmoc-Ile-OH, Fmoc-Leu-OH, Fmoc-Ser(tBu)-OH, Fmoc-Thr(tBu)-OH, Fmoc-Tyr(tBu)-OH. They are dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group is achieved using a solution of 20% (IV) piperidine in N,N-dimethylformamide (DMF) for 20 minutes (step 1). At the end of the synthesis. The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm to afford the desired modified peptide (i.e., DAC) in >95% purity, as determined by RP-HPLC.

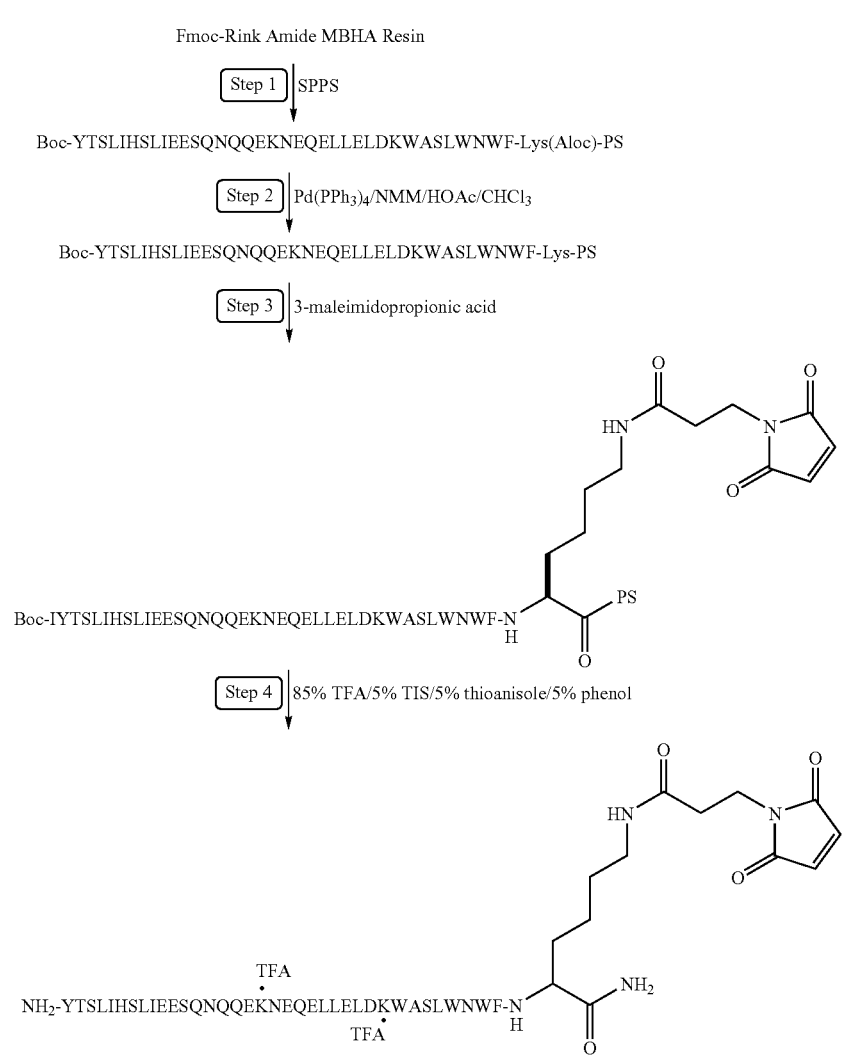

Example 2

Preparation of a Modified DP107

Synthesis of NNLLRAIEAQQHLLQLTVW-QIKQLQARILAVERYLKDQK(MPA)NH$_2$

In this example, DP107 (SEQ ID NO:2) is synthesized and modified to include a linker and maleimide group according to the following synthesis scheme. As reported in U.S. Pat. Nos. 6,013,236 and 6,020,459, DP107 exhibits potent antiviral activity against HIV.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Gln(Trt)-OH, Fmoc-Asp(tBu)-OH, Fmoc-Lys(Boc)-OH, Fmoc-Leu-OH, Fmoc-Tyr(tBu)-OH, Fmoc-Arg(Pbf)-OH, Fmoc-Glu(tBu)-OH, Fmoc-Val-OH, Fmoc-Ala-OH, Fmoc-Leu-OH, Fmoc-Ile-OH, Fmoc-Arg(Pbf)-OH, Fmoc-Ala-OH, Fmoc-Gln(Trt)-OH, Fmoc-Leu-OH, Fmoc-Gln(Trt)-OH, Fmoc-Lys(Boc)-OH, Fmoc-Ile-OH, Fmoc-Gln(Trt)-OH, Fmoc-Trp(Boc)-OH, Fmoc-Val-OH, Fmoc-Thr(tBu)-OH, Fmoc-Leu-OH, Fmoc-Gln(Trt)-OH, Fmoc-Leu-OH, Fmoc-Leu-OH, Fmoc-His(Boc)-OH, Fmoc-Gln(Trt)-OH, Fmoc-Gln(Trt)-OH, Fmoc-Ala-OH, Fmoc-Glu(tBu)-OH, Fmoc-Ile-OH, Fmoc-Ala-OH, Fmoc-Arg(Pbf)-OH, Fmoc-Leu-OH, Fmoc-Leu-OH, Fmoc-Asn(Trt)-OH, Fmoc-Asn(Trt)-OH, They are dissolved in N,N-dimethylformamide (DMF) and, according to the sequence, activated using O-benzotriazol-1-yl-N,N, N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). At the end of the synthesis. The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired modified peptide (i.e., DAC) in >95% purity, as determined by RP-HPLC.

DP-107 C

Fmoc-Rink Amide MBHA Resin

Step 1 | SPPS

Boc-NNLLRAIEAQQHLLQLTVWQIKQLQARILAVERYLKDQ-Lys(Aloc)-PS

Step 2 | Pd(PPh$_3$)$_4$/NMM/HOAc/CHCl$_3$

Boc-NNLLRAIEAQQHLLQLTVWQIKQLQARILAVERYLKDQ-Lys-PS

Step 3 | 3-maleimidopropionic acid

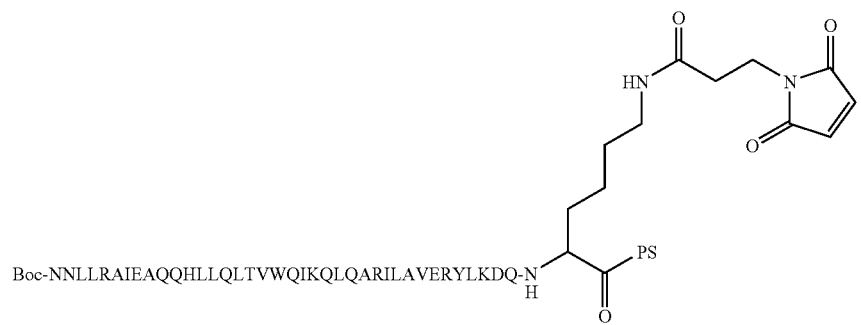

Step 4 | 85% TFA/5% TIS/5% thioanisole/5% phenol

-continued

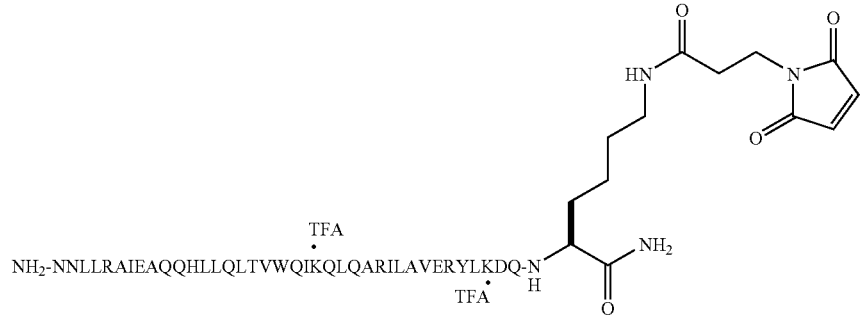

Example 3

Preparation of a Modified Anti-RSV Peptide (C Terminal)

In this example, the peptide VITIELSNIKENKCN-GAKVKLIKQELDKYKNAV (SEQ ID NO:16) is modified to include a linker and maleimide group according to the synthesis scheme set forth below. As reported in U.S. Pat. Nos. 6,013,236 and 6,020,459, the native sequence (SEQ ID NO.) inhibits viral infection of respiratory syncytial virus (RSV), including inhibiting fusion and syncytia formation between RSV-infected and uninfected Hep-2 cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Val-OH, Fmoc-Ala-OH, Fmoc-Asn(Trt)-OH, Fmoc-Lys(Boc)-OH, Fmoc-Tyr(tBu)-OH, Fmoc-Lys(Boc)-OH, Fmoc-Asp(tBu)-OH, Fmoc-Leu-OH, Fmoc-Glu(tBu)-OH, Fmoc-Gln(Trt)-OH, Fmoc-Lys(Boc)-OH, Fmoc-Ile-OH, Fmoc-Leu-OH, Fmoc-Lys(Boc)-OH, Fmoc-Val-OH, Fmoc-Lys(Boc)-OH, Fmoc-Ala-OH, Fmoc-Gly-OH, Fmoc-Asn(Trt)-OH, Fmoc-Cys(Trt)-OH, Fmoc-Lys(Boc)-OH, Fmoc-Asn(Trt)-OH, Fmoc-Glu(tBu)-OH, Fmoc-Lys(Boc)-OH, Fmoc-Ile-OH, Fmoc-Asn(Trt)-OH, Fmoc-Ser(tBu)-OH, Fmoc-Leu-OH, Fmoc-Glu(tBu)-OH, Fmoc-Ile-OH, Fmoc-Thr(tBu)-OH, Fmoc-Ile-OH, Fmoc-Val-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired modified peptide (i.e., DAC) in >95% purity, as determined by RP-HPLC.

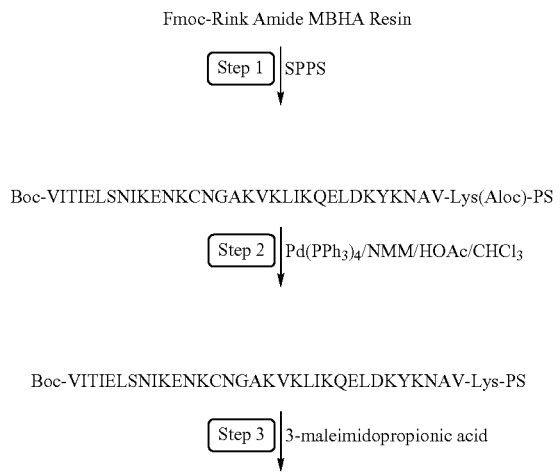

-continued

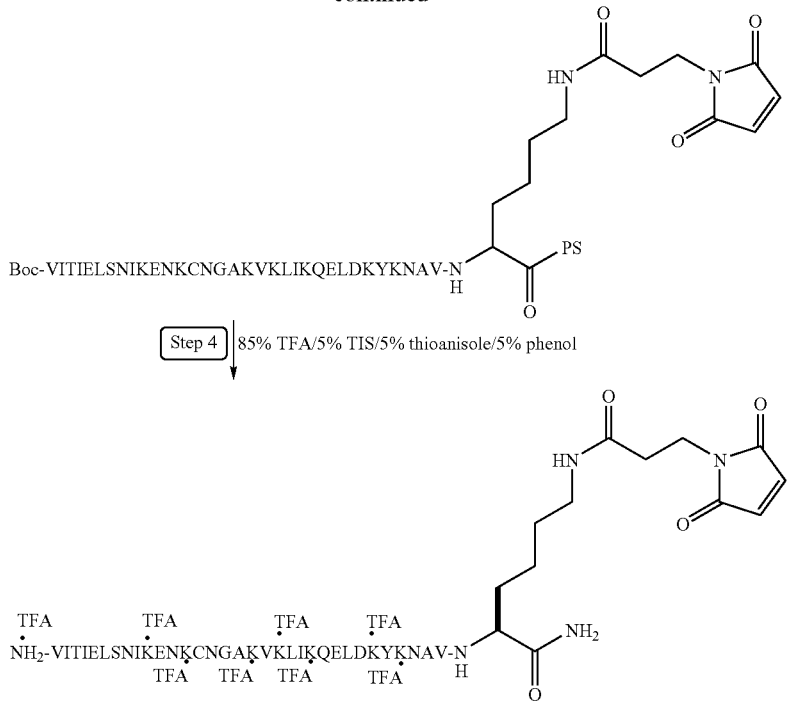
Example 4
Preparation of a Modified Anti-RSV Peptide (T-N Terminal)

In this example, the peptide VITIELSNIKENKCNGAKVKLIKQELDKYKNAV (SEQ ID NO:17), which corresponds to the peptide of SEQ ID NO:16 but where a Cysteine (C) has been substituted for the Methionine (M), residue is synthesized and modified to include a linker and maleimide group according to the synthesis scheme set forth below. As reported in U.S. Pat. Nos. 6,013,236 and 6,020,459, the native sequence (SEQ ID NO:16) inhibits viral infection of respiratory syncytial virus (RSV), including inhibiting fusion and syncytia formation between RSV-infected and uninfected Hep-2 cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Val-OH, Fmoc-Ala-OH, Fmoc-Asn(Trt)-OH, Fmoc-Lys(Boc)-OH, Fmoc-Tyr(tBu)-OH, Fmoc-Lys(Boc)-OH, Fmoc-Asp(tBu)-OH, Fmoc-Leu-OH, Fmoc-Glu(tBu)-OH, Fmoc-Gln(Trt)-OH, Fmoc-Lys(Boc)-OH, Fmoc-Ile-OH, Fmoc-Leu-OH, Fmoc-Lys(Boc)-OH, Fmoc-Val-OH, Fmoc-Lys(Boc)-OH, Fmoc-Ala-OH, Fmoc-Gly-OH, Fmoc-Asn(Trt)-OH, Fmoc-Met-OH, Fmoc-Lys(Boc)-OH, Fmoc-Asn(Trt)-OH, Fmoc-Glu(tBu)-OH, Fmoc-Lys(Boc)-OH, Fmoc-Ile-OH, Fmoc-Asn(Trt)-OH, Fmoc-Ser(tBu)-OH, Fmoc-Leu-OH, Fmoc-Glu(tBu)-OH, Fmoc-Ile-OH, Fmoc-Thr(tBu)-OH, Fmoc-Ile-OH, Fmoc-Val-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired modified peptide (i.e., DAC) in >95% purity, as determined by RP-HPLC.

DAC:RSV

Fmoc-Rink Amide MBHA Resin

Step 1 SPPS

-continued
Fmoc-VITIELSNIKENKMNGAKVKLIKQELDKYKNAV-PS

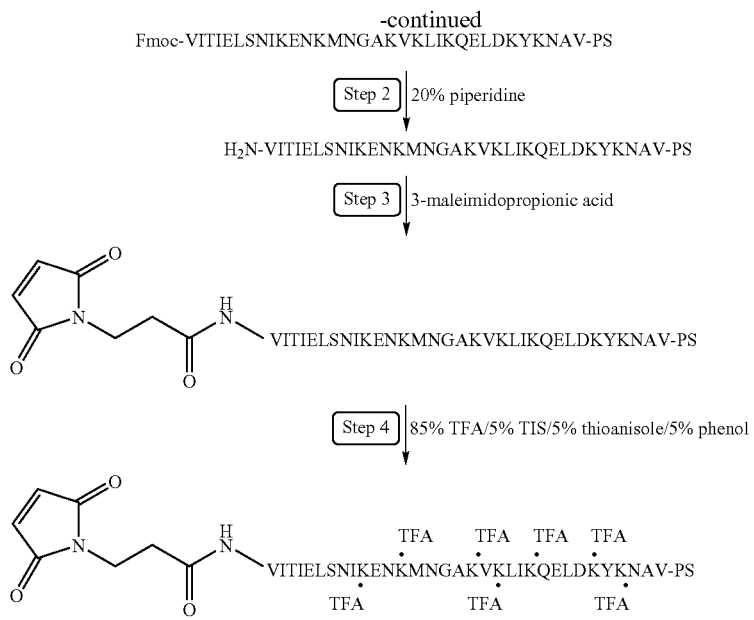

Example 5

Preparation of a Modified Anti-RSV Peptide

In this example, the peptide SEQ ID NO:14 is synthesized and modified to include a linker and maleimide group according to the synthesis scheme set forth below. As reported in U.S. Pat. Nos. 6,013,236 and 6,020,459, SEQ ID NO:14 inhibits viral infection of respiratory syncytial virus (RSV), including inhibiting fusion and syncytia formation between RSV-infected and uninfected Hep-2 cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Lys (Boc)-OH, Fmoc-Tyr(tBu)-OH, Fmoc-Lys(Boc)-OH, Fmoc-Asp(tBu)-OH, Fmoc-Leu-OH, Fmoc-U Glu(tBu)-OH, Fmoc-Gln(Trt)-OH, Fmoc-Lys(Boc)-OH, Fmoc-Ile-OH, Fmoc-Leu-OH, Fmoc-Lys(Boc)-OH, Fmoc-Val-OH, Fmoc-Lys(Boc)-OH, Fmoc-Ala-OH, Fmoc-Gly-OH, Fmoc-Asn (Trt)-OH, Fmoc-Cys(Trt)-OH, Fmoc-Lys(Boc)-OH, Fmoc-Asn(Trt)-OH, Fmoc-Glu(tBu)-OH, Fmoc-Lys(Boc)-OH, Fmoc-Ile-OH, Fmoc-Asn(Trt)-OH, Fmoc-Ser(tBu)-OH, Fmoc-Leu-OH, Fmoc-Glu(tBu)-OH, Fmoc-Ile-OH, Fmoc-Thr(tBu)-OH, Fmoc-Ile-OH, Fmoc-Val-OH, Fmoc-Ser (tBu)-OH, Fmoc-Thr(tBu)-OH, Fmoc-Tyr(tBu)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at 214 and 254 nm to afford the desired modified peptide (i.e., DAC) in >95% purity, as determined by RP-HPLC.

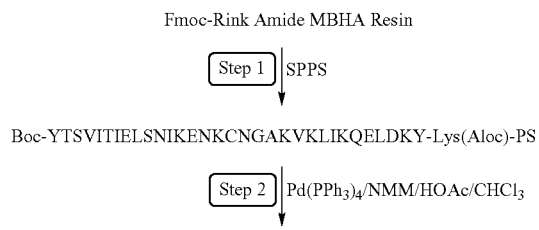

Boc--YTSVITIELSNIKENKCNGAKVKLIKQELDKY-Lys-PS

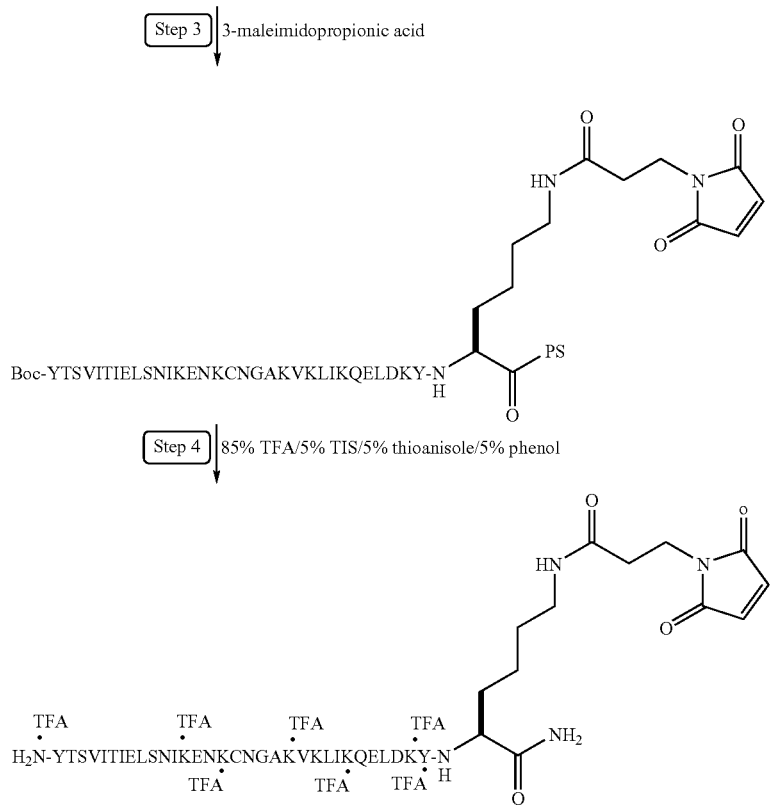

Example 6

T-143

Preparation of a Modified Anti-RSV Peptide

In this example, the peptide SEQ ID NO:15 is synthesized and modified to include a linker and maleimide group according to the synthesis scheme set forth below. As reported in U.S. Pat. Nos. 6,013,236 and 6,020,459, SEQ ID NO:15 inhibits viral infection of respiratory syncytial virus (RSV), including inhibiting fusion and syncytia formation between RSV-infected and uninfected Hep-2 cells.

Solid phase peptide synthesis of the modified peptide analog on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Asn(Trt)-OH, Fmoc-Lys(Boc)-OH, Fmoc-Tyr(tBu)-OH, Fmoc-Lys(Boc)-OH, Fmoc-Asp(tBu)-OH, Fmoc-Leu-OH, Fmoc-Glu(tBu)-OH, Fmoc-Gln(Trt)-OH, Fmoc-Lys(Boc)-OH, Fmoc-Ile-OH, Fmoc-Leu-OH, Fmoc-Lys(Boc)-OH, Fmoc-Val-OH, Fmoc-Lys(Boc)-OH, Fmoc-Ala-OH, Fmoc-Gly-OH, Fmoc-Asn(Trt)-OH, Fmoc-Cys(Trt)-OH, Fmoc-Lys(Boc)-OH, Fmoc-Asn(Trt)-OH, Fmoc-Glu(tBu)-OH, Fmoc-Lys(Boc)-OH, Fmoc-Ile-OH, Fmoc-Asn(Trt)-OH, Fmoc-Ser(tBu)-OH, Fmoc-Leu-OH, Fmoc-Glu(tBu)-OH, Fmoc-Ile-OH, Fmoc-Thr(tBu)-OH, Fmoc-Ile-OH, Fmoc-Val-OH, Fmoc-Ser(tBu)-OH, Fmoc-Thr(tBu)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethyl-formamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm to afford the desired modified peptide (i.e., DAC) in >95% purity, as determined by RP-HPLC.

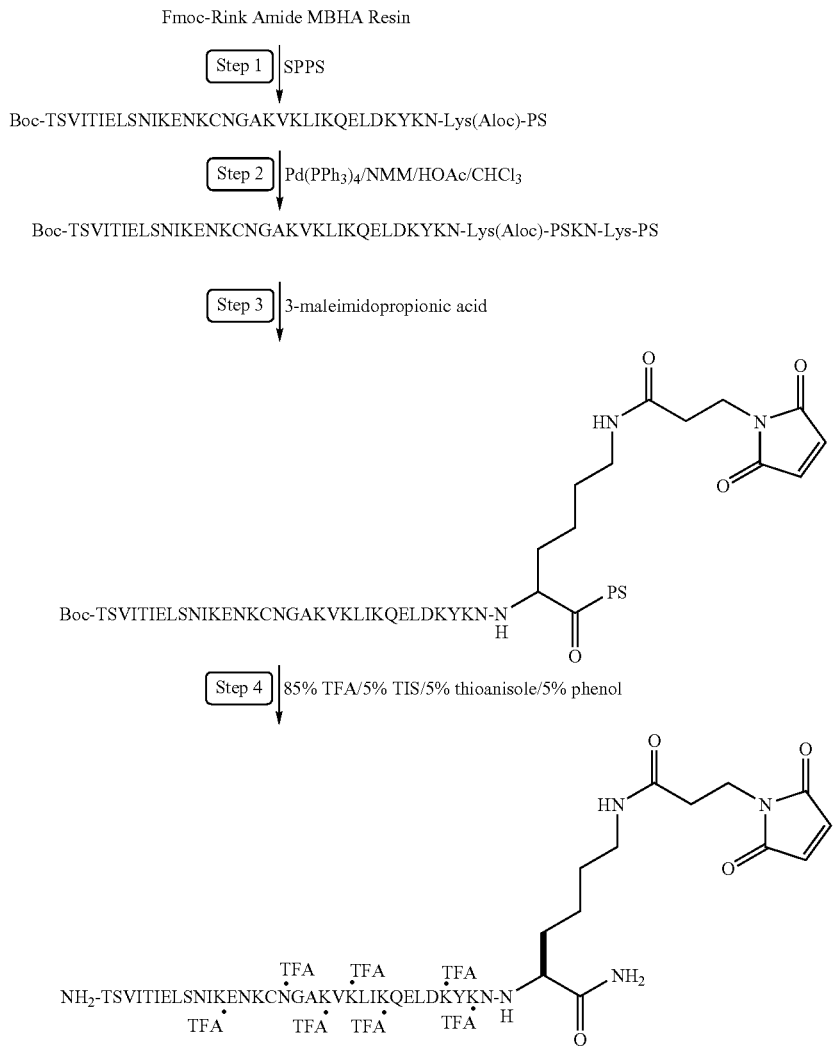

Example 7

Preparation of a Modified Anti-RSV Peptide (C Terminal)

In this example, the peptide SEQ ID NO:17), which corresponds to SEQ ID NO:16 with a cysteine (C) substituted for the Methionine (M), is synthesized and modified to include a linker and maleimide group according to the synthesis scheme set forth below. As reported in U.S. Pat. Nos. 6,013,236 and 6,020,459, the native sequence SEQ ID NO:16. inhibits viral infection of respiratory syncytial virus (RSV), including inhibiting fusion and syncytia formation between RSV-infected and uninfected Hep-2 cells.

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Val-OH, Fmoc-Ala-OH, Fmoc-Asn(Trt)-OH, Fmoc-Lys(Boc)-OH, Fmoc-Tyr(tBu)-OH, Fmoc-Lys(Boc)-OH, Fmoc-Asp (tBu)-OH, Fmoc-Leu-OH, Fmoc-Glu(tBu)-OH, Fmoc-Gln (Trt)-OH, Fmoc-Lys(Boc)-OH, Fmoc-Ile-OH, Fmoc-Leu-OH, Fmoc-Lys(Boc)-OH, Fmoc-Val-OH, Fmoc-Lys(Boc)-OH, Fmoc-Ala-OH, Fmoc-Gly-OH, Fmoc-Asn(Trt)-OH, Fmoc-Met-OH, Fmoc-Lys(Boc)-OH, Fmoc-Asn(Trt)-OH, Fmoc-Glu(tBu)-OH, Fmoc-Lys(Boc)-OH, Fmoc-Ile-OH, Fmoc-Asn(Trt)-OH, Fmoc-Ser(tBu)-OH, Fmoc-Leu-OH, Fmoc-Glu(tBu)-OH, Fmoc-Ile-OH, Fmoc-Thr(tBu)-OH, Fmoc-Ile-OH, Fmoc-Val-OH. They are dissolved in N,N-dimethylformamide (DMF) and, according to the sequence, activated using O-benzotriazol-1-yl-N,N, N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85%

TFA/5% TIS/5% thioanisole and 5% phenol, followed by precipitation by dry-ice cold Et₂O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

thesis, a Symphony Peptide Synthesizer and Fmoc protected Rink Amide MBHA. The following protected amino acids are sequentially added to resin: Fmoc-Lys(Aloc)-OH, Fmoc-Lys (Boc)-OH, Fmoc-Asp(tBu)-OH, Fmoc-Ile-OH, Fmoc-Tyr (tBu)-OH, Fmoc-Asn(Trt)-OH, Fmoc-Lys(Boc)-OH, Fmoc-Leu-OH, Fmoc-Asp(tBu)-OH, Fmoc-Leu-OH, Fmoc-Val-OH, Fmoc-Lys(Boc)-OH, Fmoc-Ser(tBu)-OH, Fmoc-Thr(tBu)-OH, Fmoc-Leu-OH, Fmoc-Val-OH, Fmoc-Ser(tBu)-OH, Fmoc-Val-OH, Fmoc-Gly-OH, Fmoc-Asn(Trt)-OH, Fmoc-Ser(tBu)-OH, Fmoc-Leu-OH, Fmoc-Ser(tBu)-OH,

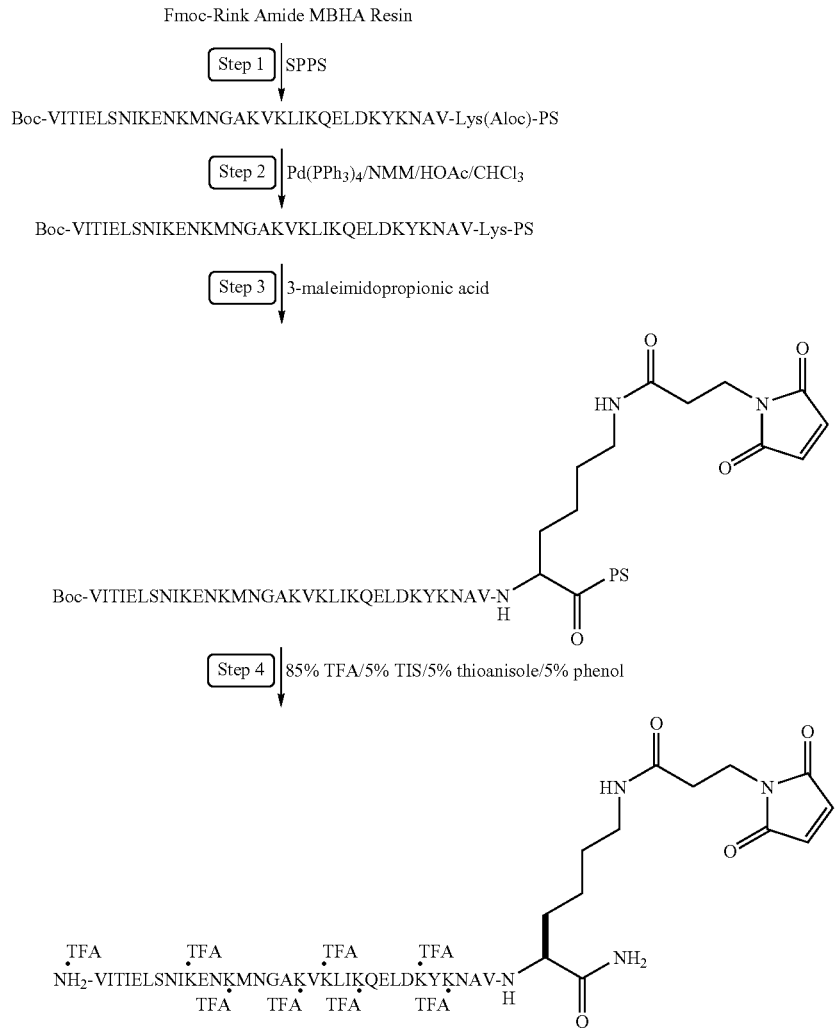

Example 8

Preparation of a Modified Anti-RSV Peptide

In this example, the peptide SEQ ID NO:29. is synthesized and modified to include a linker and maleimide group according to the synthesis scheme set forth below. As reported in U.S. Pat. Nos. 6,013,236 and 6,020,459, SEQ ID NO:29 inhibits viral infection of respiratory syncytial virus (RSV), including inhibiting fusion and syncytia formation between RSV-infected and uninfected Hep-2 cells.

Solid phase peptide synthesis of the modified peptide on a 100 μmole scale is performed using manual solid-phase syn- Fmoc-Val-OH, Fmoc-Val-OH, Fmoc-Ala-OH, Fmoc-Lys (Boc)-OH, Fmoc-Asn(Trt)-OH, Fmoc-Thr(tBu)-OH, Fmoc-Ser(tBu)-OH, Fmoc-Leu-OH, Fmoc-Leu-OH, Fmoc-Ala-OH, Fmoc-Ile-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:

HOAc (18:1:0.5) for 2 h (Step 2). The resin is then washed with CHCl₃ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et₂O (Step 4). The product is purified by preparative reversed phased HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Example 9

T-173

Preparation of a Modified Anti-HPIV Peptide

In this example, the peptide SEQ ID NO:52. is synthesized and modified to include a linker and maleimide group according to the synthesis scheme set forth below. As reported in U.S. Pat. Nos. 6,013,236 and 6,020,459, SEQ ID NO:52 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 μmole scale is performed using manual solid-phase synthesis, a Symphony Peptide Synthesizer and Fmoc protected

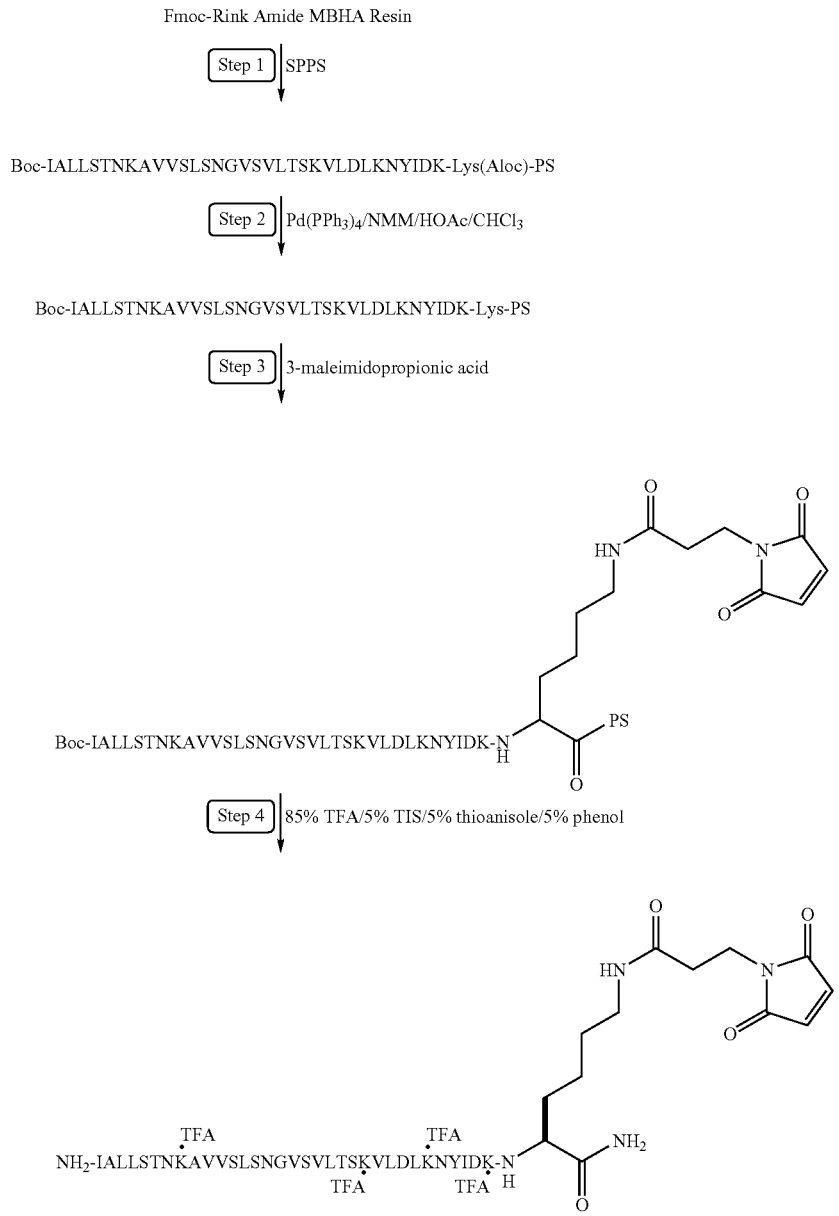

Rink Amide MBHA. The following protected amino acids are sequentially added to resin: Fmoc-Lys(Aloc)-OH, Fmoc-Ile-OH, Fmoc-Leu-OH, Fmoc-Asn(Trt)-OH, Fmoc-Gly-OH, Fmoc-Ile-OH, Fmoc-Ser(tBu)-OH, Fmoc-Ser(tBu)-OH, Fmoc-Gln(Trt)-OH, Fmoc-Val-OH, Fmoc-Ser(tBu)-OH, Fmoc-Gln(Trt)-OH, Fmoc-Val-OH, Fmoc-Ala-OH, Fmoc-Lys(Boc)-OH, Fmoc-Asn(Trt)-OH, Fmoc-Thr(tBu)-OH, Fmoc-Asp(tBu)-OH, Fmoc-Arg(Pbf)-OH, Fmoc-Ile-OH, Fmoc-Ala-OH, Fmoc-Glu(tBu)-OH, Fmoc-Lys(Boc)-OH, Fmoc-Leu-OH, Fmoc-Lys(Boc)-OH, Fmoc-Glu(tBu)-OH, Fmoc-Ile-OH, Fmoc-Asp(tBu)-OH, Fmoc-Ser(tBu)-OH, Fmoc-Arg(Pbf)-OH, Fmoc-Ala-OH, Fmoc-Gln(Trt)-OH, Fmoc-Lys(Boc)-OH, Fmoc-Ala-OH, Fmoc-Glu(tBu)-OH, Fmoc-Val-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18: 1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

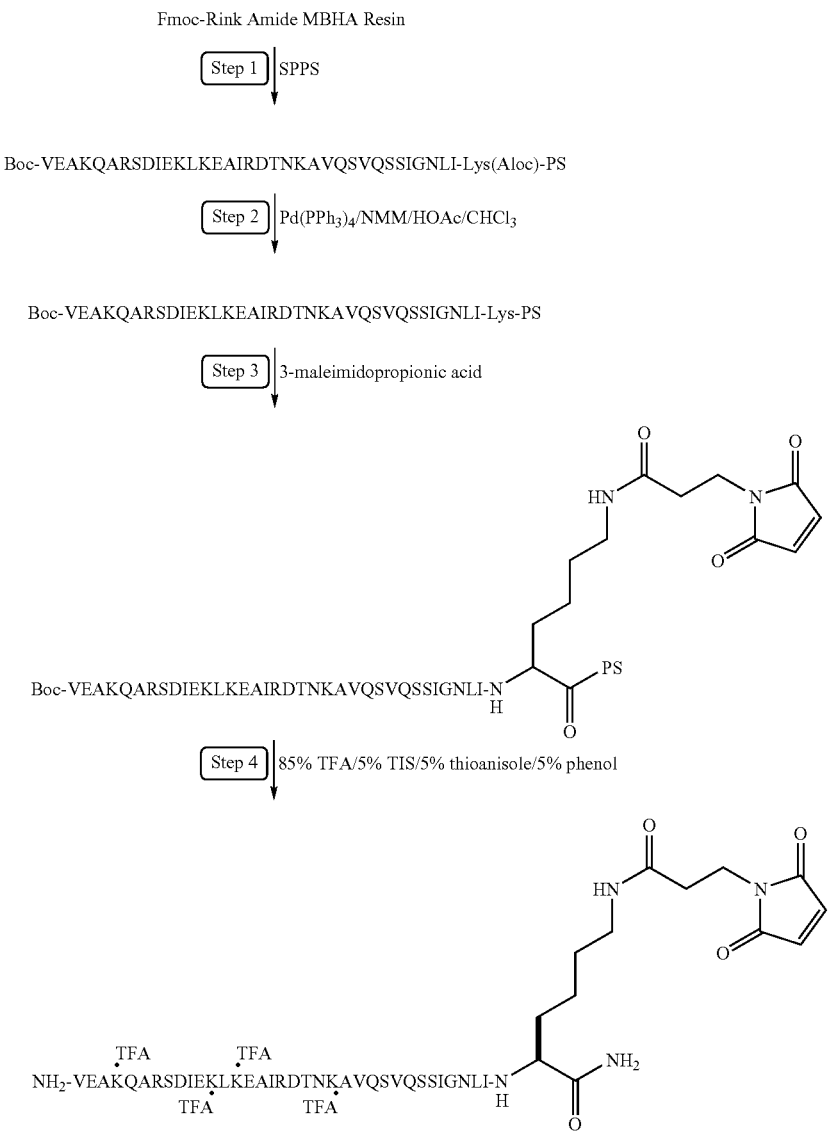

Example 10

Preparation of a Modified Anti-HPIV Peptide

In this example, the peptide SEQ ID NO:58 is synthesized and modified to include a linker and maleimide group according to the synthesis scheme set forth below. As reported in U.S. Pat. Nos. 6,013,236 and 6,020,459, SEQ ID NO:58 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Val-OH, Fmoc-Ser(tBu)-OH, Fmoc-Lys(Boc)-OH, Fmoc-Ile-OH, Fmoc-Ala-OH, Fmoc-Val-OH, Fmoc-Ile-OH, Fmoc-Leu-OH, Fmoc-Asn(Trt)-OH, Fmoc-Gly-OH, Fmoc-Ile-OH, Fmoc-Ser(tBu)-OH, Fmoc-Ser(tBu)-OH, Fmoc-Gln(Trt)-OH, Fmoc-Val-OH, Fmoc-Ser(tBu)-OH, Fmoc-Gln(Trt)-OH, Fmoc-Val-OH, Fmoc-Ala-OH, Fmoc-Lys(Boc)-OH, Fmoc-Asn(Trt)-OH, Fmoc-Thr(tBu)-OH, Fmoc-Asp(tBu)-OH, Fmoc-Arg(Pbf)-OH, Fmoc-Ile-OH, Fmoc-Ala-OH, Fmoc-Glu(tBu)-OH, Fmoc-Lys(Boc)-OH, Fmoc-Leu-OH, Fmoc-Lys(Boc)-OH, Fmoc-Glu(tBu)-OH, Fmoc-Ile-OH, Fmoc-Asp(tBu)-OH, Fmoc-Ser(tBu)-OH, Fmoc-Arg(Pbf)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Fmoc-Rink Amide MBHA Resin

Step 1 | SPPS

Boc-RSDIEKLKEAIRDTNKAVQSVQSSIGNLIVAIKSV-Lys(Aloc)-PS

Step 2 | Pd(PPh$_3$)$_4$/NMM/HOAc/CHCl$_3$

Boc-RSDIEKLKEAIRDTNKAVQSVQSSIGNLIVAIKSV-Lys-PS

Step 3 | 3-maleimidopropionic acid

Boc-RSDIEKLKEAIRDTNKAVQSVQSSIGNLIVAIKSV-N(H)-[Lys-maleimide]-PS

Step 4 | 85% TFA/5% TIS/5% thioanisole/5% phenol

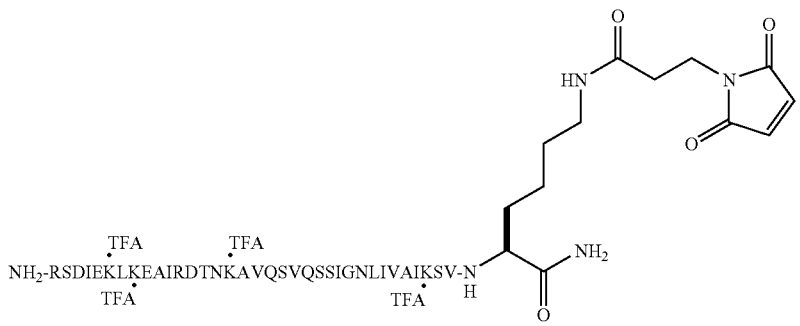

Example 11

Preparation of a Modified Anti-HPIV Peptide

In this example, the peptide SEQ ID NO:35 is synthesized and modified to include a linker and maleimide group according to the synthesis scheme set forth below. As reported in U.S. Pat. Nos. 6,013,236 and 6,020,459, SEQ ID NO:35 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Leu-OH, Fmoc-Lys(Boc)-OH, Fmoc-Gln(Trt)-OH, Fmoc-Asn(Trt)-OH, Fmoc-Ser(tBu)-OH, Fmoc-Arg(Pbf)-OH, Fmoc-Arg(Pbf)-OH, Fmoc-Ile-OH, Fmoc-Trp(Boc)-OH, Fmoc-Glu(tBu)-OH, Fmoc-Lys(Boc)-OH, Fmoc-Ser(tBu)-OH, Fmoc-Glu(tBu)-OH, Fmoc-Glu(tBu)-OH, Fmoc-Leu-OH, Fmoc-Asp(tBu)-OH, Fmoc-Ser(tBu)-OH, Fmoc-Lys(Boc)-OH, Fmoc-Ala-OH, Fmoc-Lys(Boc)-OH, Fmoc-Asn(Trt)-OH, Fmoc-Leu-OH, Fmoc-Ile-OH, Fmoc-Glu(tBu)-OH, Fmoc-Ser(tBu)-OH, Fmoc-Ile-OH, Fmoc-Asp(tBu)-OH, Fmoc-Ile-OH, Fmoc-Pro-OH, Fmoc-Asp(tBu)-OH, Fmoc-Leu-OH, Fmoc-Gln(Trt)-OH Fmoc-Ala-OH, Fmoc-Val-OH, Fmoc-Ser(tBu)-OH, Fmoc-Asn(Trt)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

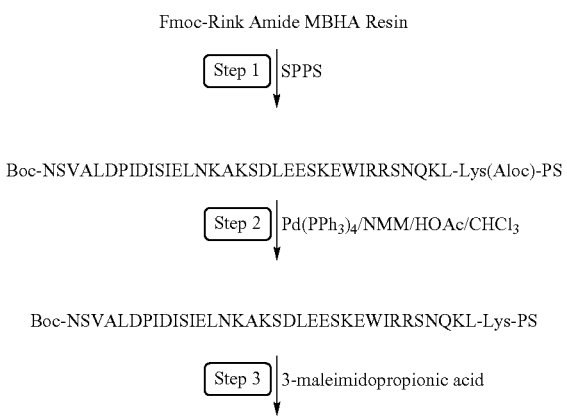

-continued

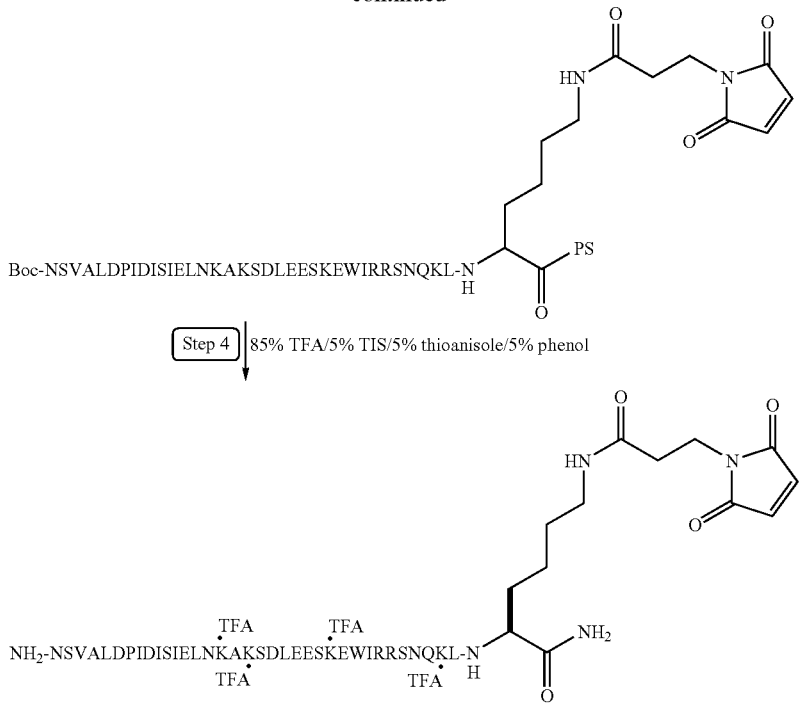
Example 12
Preparation of a Modified Anti-HPIV Peptide

In this example, the peptide SEQ ID NO:38 is synthesized and modified to include a linker and maleimide group according to the synthesis scheme set forth below. As reported in U.S. Pat. Nos. 6,013,236 and 6,020,459, SEQ ID NO: 38 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide analog on a 100 μmole scale is performed using manual solid-phase synthesis, a Symphony Peptide Synthesizer and Fmoc protected Rink Amide MBHA. The following protected amino acids are sequentially added to resin: Fmoc-Ile-OH, Fmoc-Ser(tBu)-OH, Fmoc-Asp(tBu)-OH, Fmoc-Leu-OH, Fmoc-Lys(Boc)-OH, Fmoc-Gln(Trt)-OH, Fmoc-Asn(Trt)-OH, Fmoc-Ser(tBu)-OH, Fmoc-Arg(Pbf)-OH, Fmoc-Arg(Pbf)-OH, Fmoc-Ile-OH, Fmoc-Trp(Boc)-OH, Fmoc-Glu(tBu)-OH, Fmoc-Lys(Boc)-OH, Fmoc-Ser(tBu)-OH, Fmoc-Glu(tBu)-OH, Fmoc-Glu(tBu)-OH, Fmoc-Leu-OH, Fmoc-Asp(tBu)-OH, Fmoc-Ser(tBu)-OH, Fmoc-Lys(Boc)-OH, Fmoc-Ala-OH, Fmoc-Lys(Boc)-OH, Fmoc-Asn(Trt)-OH, Fmoc-Leu-OH, Fmoc-Glu(tBu)-OH, Fmoc-Ile-OH, Fmoc-Ser(tBu)-OH, Fmoc-Ile-OH, Fmoc-Asp(tBu)-OH, Fmoc-Ile-OH, Fmoc-Pro-OH, Fmoc-Asp(tBu)-OH, Fmoc-Leu-OH, Fmoc-Ala-OH BOC-Lys(Aloc)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Fmoc-Rink Amide MBHA Resin

Step 1
SPPS

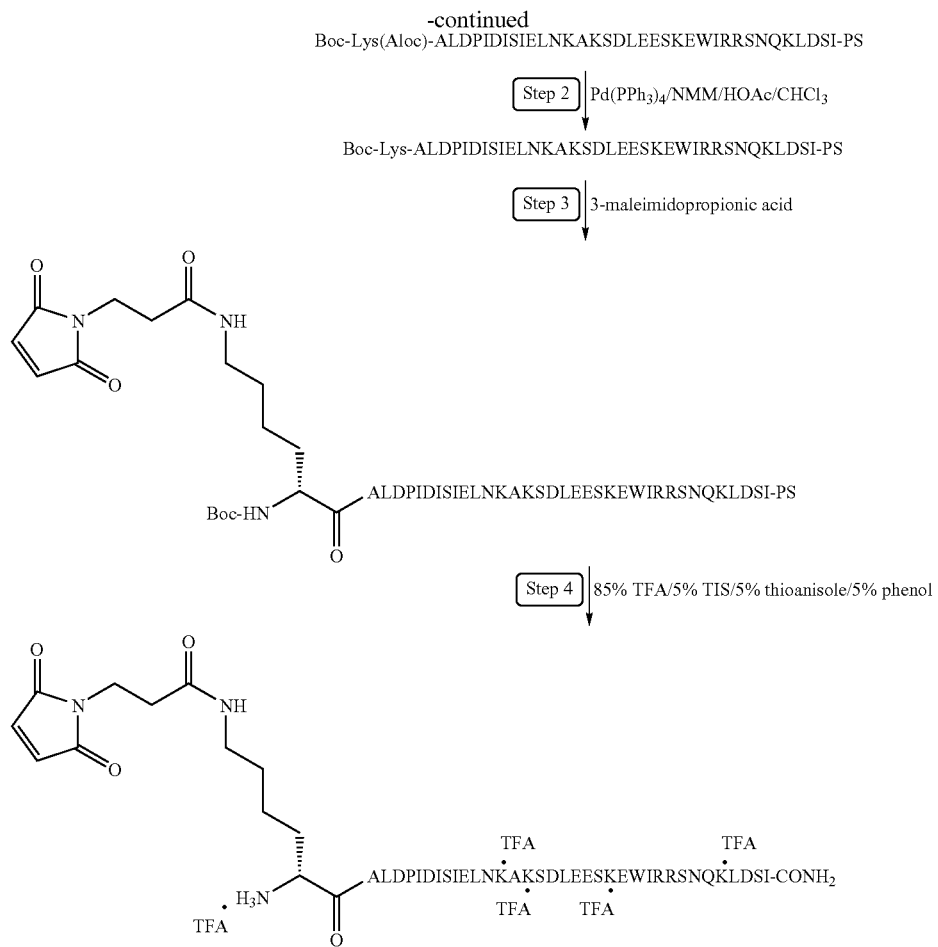

Example 13

Preparation of a Modified Anti-HPIV Peptide

In this example, the peptide SEQ ID NO:39 is synthesized and modified to include a linker and maleimide group according to the synthesis scheme set forth below. As reported in U.S. Pat. Nos. 6,013,236 and 6,020,459, SEQ ID NO:39 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Gly-OH, Fmoc-Ile-OH, Fmoc-Ser(tBu)-OH, Fmoc-Asp(tBu)-OH, Fmoc-Leu-OH, Fmoc-Lys(Boc)-OH, Fmoc-Gly-OH, Fmoc-Asn(Trt)-OH, Fmoc-Ser(tBu)-OH, Fmoc-Arg(Pbf)-OH, Fmoc-Arg(Pbf)-OH, Fmoc-Ile-OH, Fmoc-Trp(Boc)-OH, Fmoc-Glu(tBu)-OH, Fmoc-Lys(Boc)-OH, Fmoc-Ser(tBu)-OH, Fmoc-Glu(tBu)-OH, Fmoc-Glu(tBu)-OH, Fmoc-Leu-OH, Fmoc-Asp(tBu)-OH, Fmoc-Ser(tBu)-OH, Fmoc-Lys(Boc)-OH, Fmoc-Ala-OH, Fmoc-Lys(Boc)-OH, Fmoc-Asn(Trt)-OH, Fmoc-Leu-OH, Fmoc-Glu(tBu)-OH, Fmoc-Ile-OH, Fmoc-Ser(tBu)-OH, Fmoc-Ile-OH, Fmoc-Asp(tBu)-OH, Fmoc-Ile-OH, Fmoc-Pro-OH, Fmoc-Asp(tBu)-OH, Fmoc-Leu-OH. They are dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

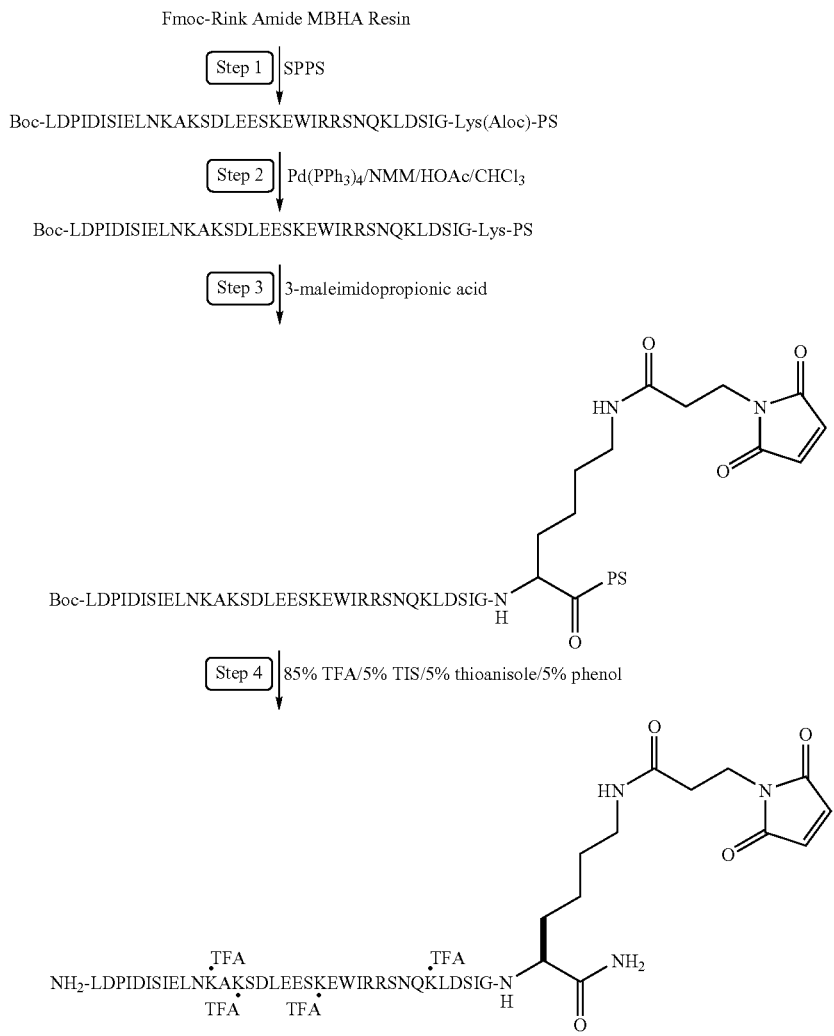
Example 14
Preparation of a Modified Anti-HPIV Peptide

In this example, the peptide SEQ ID NO:40 is synthesized and modified to include a linker and maleimide group according to the synthesis scheme set forth below. As reported in U.S. Pat. Nos. 6,013,236 and 6,020,459, SEQ ID NO. inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Asn (Trt)-OH, Fmoc-Gly-OH, Fmoc-Ile-OH, Fmoc-Ser(tBu)-OH, Fmoc-Asp(tBu)-OH, Fmoc-Leu-OH, Fmoc-Lys(Boc)-OH, Fmoc-Gly-OH, Fmoc-Asn(Trt)-OH, Fmoc-Ser(tBu)-OH, Fmoc-Arg(Pbf)-OH, Fmoc-Arg(Pbf)-OH, Fmoc-Ile-OH, Fmoc-Trp(Boc)-OH, Fmoc-Glu(tBu)-OH, Fmoc-Lys (Boc)-OH, Fmoc-Ser(tBu)-OH, Fmoc-Glu(tBu)-OH, Fmoc-Glu(tBu)-OH, Fmoc-Leu-OH, Fmoc-Asp(tBu)-OH, Fmoc-Ser(tBu)-OH, Fmoc-Lys(Boc)-OH, Fmoc-Ala-OH, Fmoc-Lys(Boc)-OH, Fmoc-Asn(Trt)-OH, Fmoc-Leu-OH, Fmoc-Glu(tBu)-OH, Fmoc-Ile-OH, Fmoc-Ser(tBu)-OH, Fmoc-Ile-OH, Fmoc-Asp(tBu)-OH, Fmoc-Ile-OH, Fmoc-Pro-OH, Fmoc-Asp(tBu)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55%

B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

(Trt)-OH, Fmoc-Gly-OH, Fmoc-Ile-OH, Fmoc-Ser(tBu)-OH, Fmoc-Asp(tBu)-OH, Fmoc-Leu-OH, Fmoc-Lys(Boc)-OH, Fmoc-Gly-OH, Fmoc-Asn(Trt)-OH, Fmoc-Ser(tBu)-OH, Fmoc-Arg(Pbf)-OH, Fmoc-Arg(Pbf)-OH, Fmoc-Ile-OH, Fmoc-Trp(Boc)-OH, Fmoc-Glu(tBu)-OH, Fmoc-Lys(Boc)-OH, Fmoc-Ser(tBu)-OH, Fmoc-Glu(tBu)-OH, Fmoc-

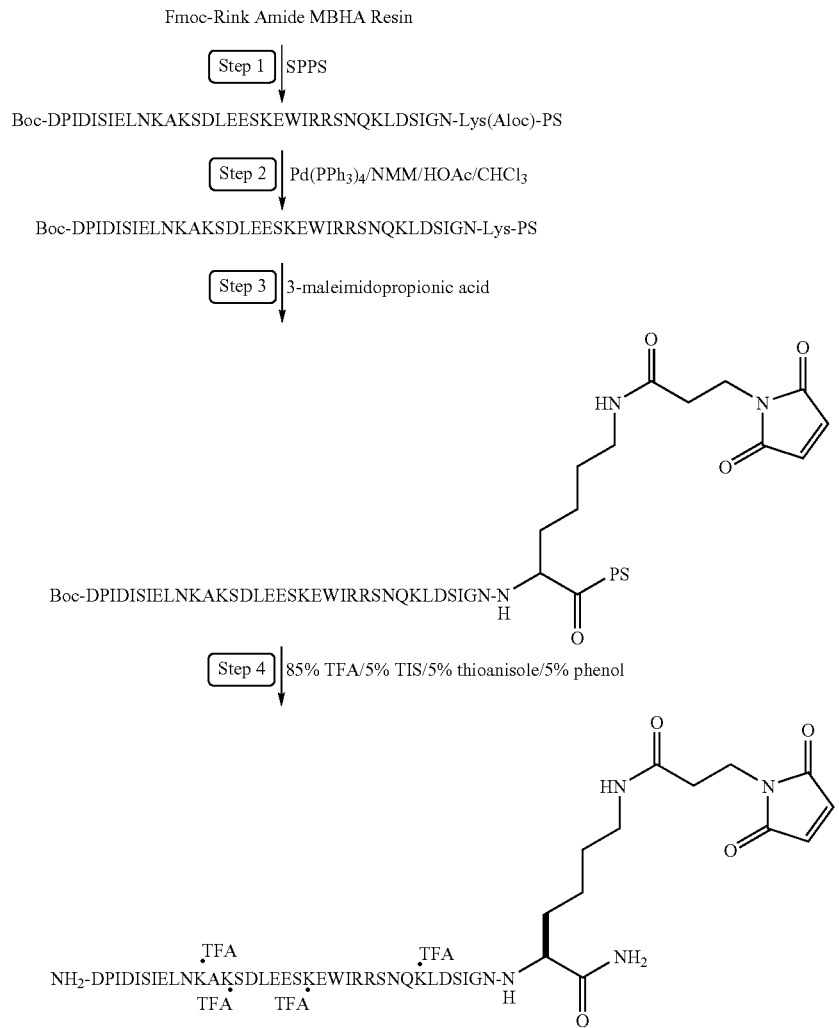

Example 15

Preparation of a Modified Anti-HPIV Peptide

In this example, the peptide SEQ ID NO:41 is synthesized and modified to include a linker and maleimide group according to the synthesis scheme set forth below. As reported in U.S. Pat. Nos. 6,013,236 and 6,020,459, SEQ ID NO:41 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Trp(Boc)-OH, Fmoc-Asn Glu(tBu)-OH, Fmoc-Leu-OH, Fmoc-Asp(tBu)-OH, Fmoc-Ser(tBu)-OH, Fmoc-Lys(Boc)-OH, Fmoc-Ala-OH, Fmoc-Lys(Boc)-OH, Fmoc-Asn(Trt)-OH, Fmoc-Leu-OH, Fmoc-Glu(tBu)-OH, Fmoc-Ile-OH, Fmoc-Ser(tBu)-OH, Fmoc-Ile-OH, Fmoc-Asp(tBu)-OH, Fmoc-Ile-OH, Fmoc-Pro-OH Boc-Lys(Aloc)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethyl-formamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

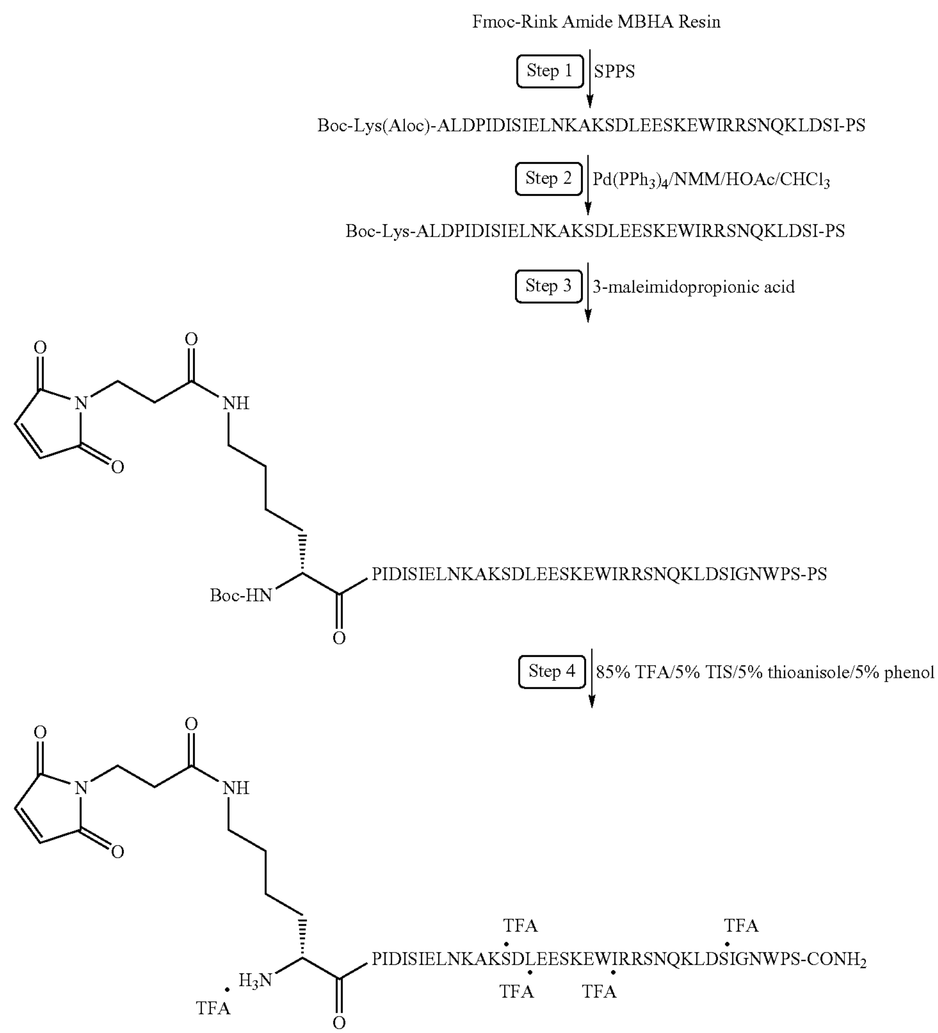

Example 16

Preparation of a Modified Anti-HPIV Peptide

In this example, the peptide SEQ ID NO:42 is synthesized and modified to include a linker and maleimide group according to the synthesis scheme set forth below. As reported in U.S. Pat. Nos. 6,013,236 and 6,020,459, SEQ ID NO:42 inhibits viral infection of human parainfluenza virus 3 (HPIV3), including inhibiting fusion and syncytia formation between HPIV3-infected Hep2 cells and uninfected CV-1W cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-His(Boc)-OH, Fmoc-Trp(Boc)-OH, Fmoc-Asn(Trt)-OH, Fmoc-Gly-OH, Fmoc-Ile-OH, Fmoc-Ser(tBu)-OH, Fmoc-Asp(tBu)-OH, Fmoc-Leu-OH, Fmoc-Lys(Boc)-OH, Fmoc-Gly-OH, Fmoc-Asn(Trt)-OH, Fmoc-Ser(tBu)-OH, Fmoc-Arg(Pbf)-OH, Fmoc-Arg(Pbf)-OH, Fmoc-Ile-OH, Fmoc-Trp(Boc)-OH, Fmoc-Glu(tBu)-OH, Fmoc-Lys(Boc)-OH, Fmoc-Ser(tBu)-OH, Fmoc-Glu(tBu)-OH, Fmoc-Glu(tBu)-OH, Fmoc-Leu-OH, Fmoc-Asp(tBu)-OH, Fmoc-Ser(tBu)-OH, Fmoc-Lys(Boc)-OH, Fmoc-Ala-OH, Fmoc-Lys(Boc)-OH, Fmoc-Asn(Trt)-OH, Fmoc-Leu-OH, Fmoc-Glu(tBu)-OH, Fmoc-Ile-OH, Fmoc-Ser(tBu)-OH, Fmoc-Ile-OH, Fmoc-Asp(tBu)-OH, Fmoc-Ile-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N- dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM: HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC Example 17

Preparation of a Modified Anti-MeV Peptide

In this example, the peptide SEQ ID NO:77. is synthesized and modified to include a linker and maleimide group according to the synthesis scheme set forth below. As reported in U.S. Pat. Nos. 6,013,236 and 6,020,459, SEQ ID NO:77 inhibits viral infection of measles virus (MeV), including inhibiting fusion and syncytia formation between MeV-infected and uninfected Vero cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Glu(tBu)-OH, Fmoc-Leu-OH, Fmoc-Leu-OH, Fmoc-Glu(tBu)-OH, Fmoc-Lys(Boc)-OH, Fmoc-Ala-OH, Fmoc-Glu(tBu)-OH, Fmoc-Leu-OH, Fmoc-Lys(Boc)-OH, Fmoc-Ala-OH, Fmoc-Ile-OH, Fmoc-Ala-OH, Fmoc-Asn(Trt)-OH, Fmoc-Gly-OH, Fmoc-Leu-OH, Fmoc-Asn(Trt)-OH, Fmoc-Thr Fmoc-Rink Amide MBHA Resin
Step 1 | SPPS Boc-IDISIELNKAKSDLEESKEWIRRSNQKLDSIGNWH-Lys(Aloc)-PS Step 2 | Pd(PPh$_3$)$_4$/NMM/HOAc/CHCl$_3$ Boc-IDISIELNKAKSDLEESKEWIRRSNQKLDSIGNWH-Lys-PS Step 3 | 3-maleimidopropionic acid Boc-IDISIELNKAKSDLEESKEWIRRSNQKLDSIGNWH-N(H)-[Lys-maleimide]-PS Step 4 | 85% TFA/5% TIS/5% thioanisole/5% phenol NH$_2$-IDISIELNKAKSDLEESKEWIRRSNQKLDSIGNWH-N(H)-[Lys-maleimide]-NH$_2$
(TFA·, TFA·, TFA·, TFA·)

(tBu)-OH, Fmoc-Gly-OH, Fmoc-Val-OH, Fmoc-Asp(tBu)-OH, Fmoc-Leu-OH, Fmoc-Arg(Pbf)-OH, Fmoc-Glu(tBu)-OH, Fmoc-Leu-OH, Fmoc-Ser(tBu)-OH, Fmoc-Ile-OH, Fmoc-Pro-OH, Fmoc-Pro-OH, Fmoc-Gly-OH, Fmoc-Leu-OH, Fmoc-Asp(tBu)-OH, Fmoc-Ile-OH, Fmoc-Arg(Pbf)-OH, Fmoc-His(Boc)-OH. They are dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM: HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Example 18

Preparation of a Modified Anti-MeV Peptide

In this example, the peptide SEQ ID NO:79 is synthesized and modified to include a linker and maleimide group according to the synthesis scheme set forth below. As reported in U.S. Pat. Nos. 6,013,236 and 6,020,459, SEQ ID NO:79 inhibits viral infection of measles virus (MeV), including inhibiting fusion and syncytia formation between MeV-infected and uninfected Vero cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Ser(tBu)-OH, Fmoc-Ser(tBu)-OH, Fmoc-Glu(tBu)-OH, Fmoc-Leu-OH, Fmoc-Leu-OH, Fmoc-Glu(tBu)-OH, Fmoc-Lys(Boc)-OH, Fmoc-Ala-OH, Fmoc-Glu(tBu)-OH, Fmoc-Leu-OH, Fmoc-Lys(Boc)-OH, Fmoc-Ala-OH, Fmoc-Ile-OH, Fmoc-Ala-OH, Fmoc-Asn(Trt)-OH, Fmoc-Gly-OH, Fmoc-Leu-OH, Fmoc-Asn(Trt)-OH, Fmoc-Thr(tBu)-OH, Fmoc-Gly-OH, Fmoc-Val-OH, Fmoc-Asp(tBu)-OH, Fmoc-Leu-OH, Fmoc-Arg(Pbf)-OH, Fmoc-Glu(tBu)-OH, Fmoc-Leu-OH, Fmoc-Ser(tBu)-OH, Fmoc-Ile-OH, Fmoc-Pro-OH, Fmoc-Pro-OH, Fmoc-Gly-OH, Fmoc-Leu-OH, Fmoc-Asp(tBu)-OH, Fmoc-Ile-OH, They are dissolved in N,N-dimethylformamide (DMF) and, according to the sequence, activated using O-benzotriazol-1-yl-N,N, N,N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC

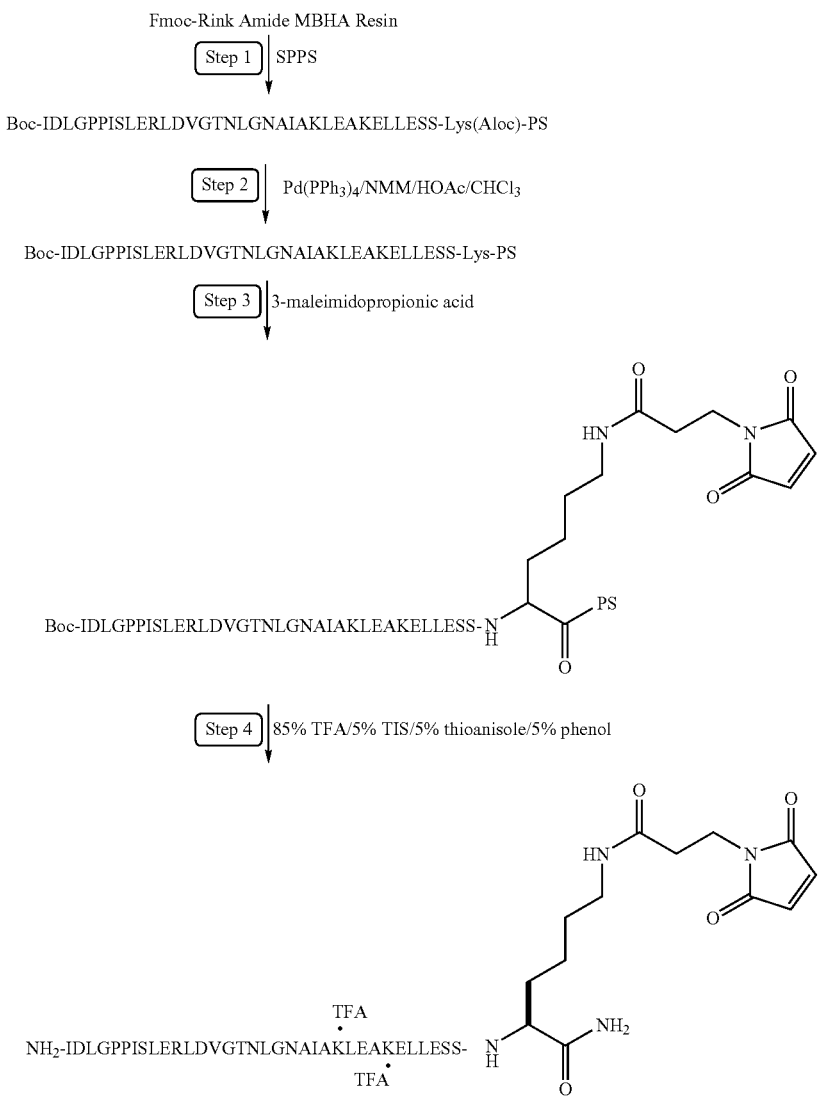

Example 19

Preparation of a Modified Anti-MeV Peptide

In this example, the peptide SEQ ID NO:81 is synthesized and modified to include a linker and maleimide group according to the synthesis scheme set forth below. As reported in U.S. Pat. Nos. 6,013,236 and 6,020,459, SEQ ID NO: 79 inhibits viral infection of measles virus (MeV), including inhibiting fusion and syncytia formation between MeV-infected and uninfected Vero cells.

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Gln(Trt)-OH, Fmoc-Asp(tBu)-OH, Fmoc-Ser(tBu)-OH, Fmoc-Ser(tBu)-OH, Fmoc-Glu(tBu)-OH, Fmoc-Leu-OH, Fmoc-Leu-OH, Fmoc-Glu(tBu)-OH, Fmoc-Lys(Boc)-OH, Fmoc-Ala-OH, Fmoc-Glu(tBu)-OH, Fmoc-Leu-OH, Fmoc-Lys(Boc)-OH, Fmoc-Ala-OH, Fmoc-Ile-OH, Fmoc-Ala-OH, Fmoc-Asn(Trt)-OH, Fmoc-Gly-OH, Fmoc-Leu-OH, Fmoc-Asn(Trt)-OH, Fmoc-Thr(tBu)-OH, Fmoc-Gly-OH, Fmoc-Val-OH, Fmoc-Asp(tBu)-OH, Fmoc-Leu-OH, Fmoc-Arg(Pbf)-OH, Fmoc-Glu(tBu)-OH, Fmoc-Leu-OH, Fmoc-Ser(tBu)-OH, Fmoc-Ile-OH, Fmoc-Pro-OH, Fmoc-Pro-OH, Fmoc-Gly-OH, Fmoc-Leu-OH. They are dissolved in N,N-dimethylformamide (DMF) and, according to the sequence, activated using O-benzotriazol-1-yl-N,N, N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Fmoc-Rink Amide MBHA Resin

Step 1 | SPPS

Boc-LGPPISLERLDVGTNLGNAIAKLEAKELLESSDQ-Lys(Aloc)-PS

Step 2 | Pd(PPh$_3$)$_4$/NMM/HOAc/CHCl$_3$

Boc-LGPPISLERLDVGTNLGNAIAKLEAKELLESSDQ-Lys-PS

Step 3 | 3-maleimidopropionic acid

Boc-LGPPISLERLDVGTNLGNAIAKLEAKELLESSDQ-[maleimide-linker-Lys]-PS

Step 4 | 85% TFA/5% TIS/5% thioanisole/5% phenol

NH₂-LGPPISLERLDVGTNLGNAIAKLEAKELLESSDQ- [structure showing Lys residue with side chain connected via amide to 3-maleimidopropionyl group; C-terminus as CONH₂; two TFA counterions associated with the peptide]

Example 20

Preparation of a Modified Anti-MeV Peptide

In this example, the peptide SEQ ID NO:84 is synthesized and modified to include a linker and maleimide group according to the synthesis scheme set forth below. As reported in U.S. Pat. Nos. 6,013,236 and 6,020,459, SEQ ID NO:84 inhibits viral infection of measles virus (MeV), including inhibiting fusion and syncytia formation between MeV-infected and uninfected Vero cells.

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Arg(Pbf)-OH, Fmoc-Leu-OH, Fmoc-Ile-OH, Fmoc-Gln(Trt)-OH, Fmoc-Asp(tBu)-OH, Fmoc-Ser(tBu)-OH, Fmoc-Ser(tBu)-OH, Fmoc-Glu(tBu)-OH, Fmoc-Leu-OH, Fmoc-Leu-OH, Fmoc-Glu(tBu)-OH, Fmoc-Lys(Boc)-OH, Fmoc-Ala-OH, Fmoc-Glu(tBu)-OH, Fmoc-Leu-OH, Fmoc-Lys(Boc)-OH, Fmoc-Ala-OH, Fmoc-Ile-OH, Fmoc-Ala-OH, Fmoc-Asn(Trt)-OH, Fmoc-Gly-OH, Fmoc-Leu-OH, Fmoc-Asn(Trt)-OH, Fmoc-Thr(tBu)-OH, Fmoc-Gly-OH, Fmoc-Val-OH, Fmoc-Asp(tBu)-OH, Fmoc-Leu-OH, Fmoc-Arg(Pbf)-OH, Fmoc-Glu(tBu)-OH, Fmoc-Leu-OH, Fmoc-Ser(tBu)-OH, Fmoc-Ile-OH, Fmoc-Pro-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh₃)₄ dissolved in 5 mL of CHCl₃:NMM:HOAc (18:1:0.5) for 2 h (Step 2). The resin is then washed with CHCl₃ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et₂O (Step 4). The product is purified by preparative reversed phased HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Fmoc-Rink Amide MBHA Resin

Step 1 | SPPS

Boc-PISLERLDVGTNLGNAIAKLEAKELLESSDQILR-Lys(Aloc)-PS

Step 2 | Pd(PPh₃)₄/NMM/HOAc/CHCl₃

Boc-PISLERLDVGTNLGNAIAKLEAKELLESSDQILR-Lys-PS

Step 3 | 3-maleimidopropionic acid

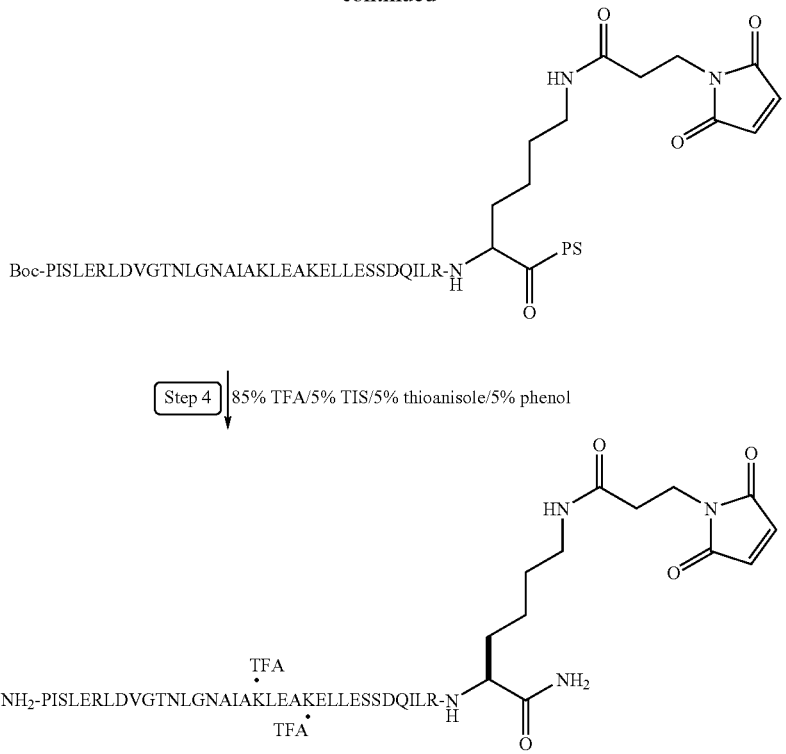

Example 21

Preparation of a Modified Anti-SIV Peptide

In this example, the peptide SEQ ID NO:64 is synthesized and modified to include a linker and maleimide group according to the synthesis scheme set forth below. As reported in U.S. Pat. Nos. 6,013,236 and 6,020,459, SEQ ID NO:64. exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Lys (Boc)-OH, Fmoc-Gln(Trt)-OH, Fmoc-Leu-OH, Fmoc-Glu (tBu)-OH, Fmoc-Tyr(tBu)-OH, Fmoc-Met-OH, Fmoc-Asn (Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln (Trt)-OH, Fmoc-Ala-OH, Fmoc-Glu(tBu)-OH, Fmoc-Glu (tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Fmoc-Arg(Pbf)-OH, Fmoc-Glu(tBu)-OH, Fmoc-Trp(Boc)-OH, Fmoc-Glu(tBu)-OH, Fmoc-Gln(Trt)-OH, Fmoc-Trp(Boc)-OH. They are dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

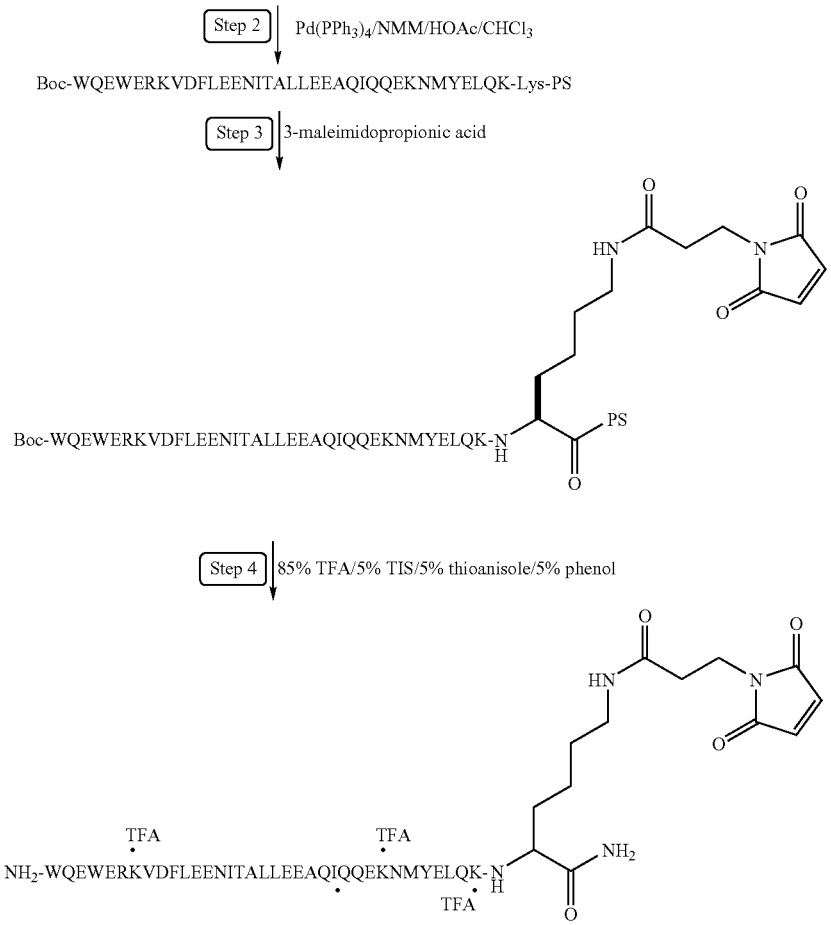

Example 22

Preparation of a Modified Anti-SIV Peptide

In this example, the peptide SEQ ID NO:65 is synthesized and modified to include a linker and maleimide group according to the synthesis scheme set forth below. As reported in U.S. Pat. Nos. 6,013,236 and 6,020,459, SEQ ID NO:65 exhibits potent antiviral activity as a crude peptide against simian immunodeficiency virus (SIV).

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Fmoc-Arg(Pbf)-OH, Fmoc-Glu(tBu)-OH, Fmoc-Trp(Boc)-OH, Fmoc-Glu(tBu)-OH, Fmoc-Gln(Trt)-OH. They are dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

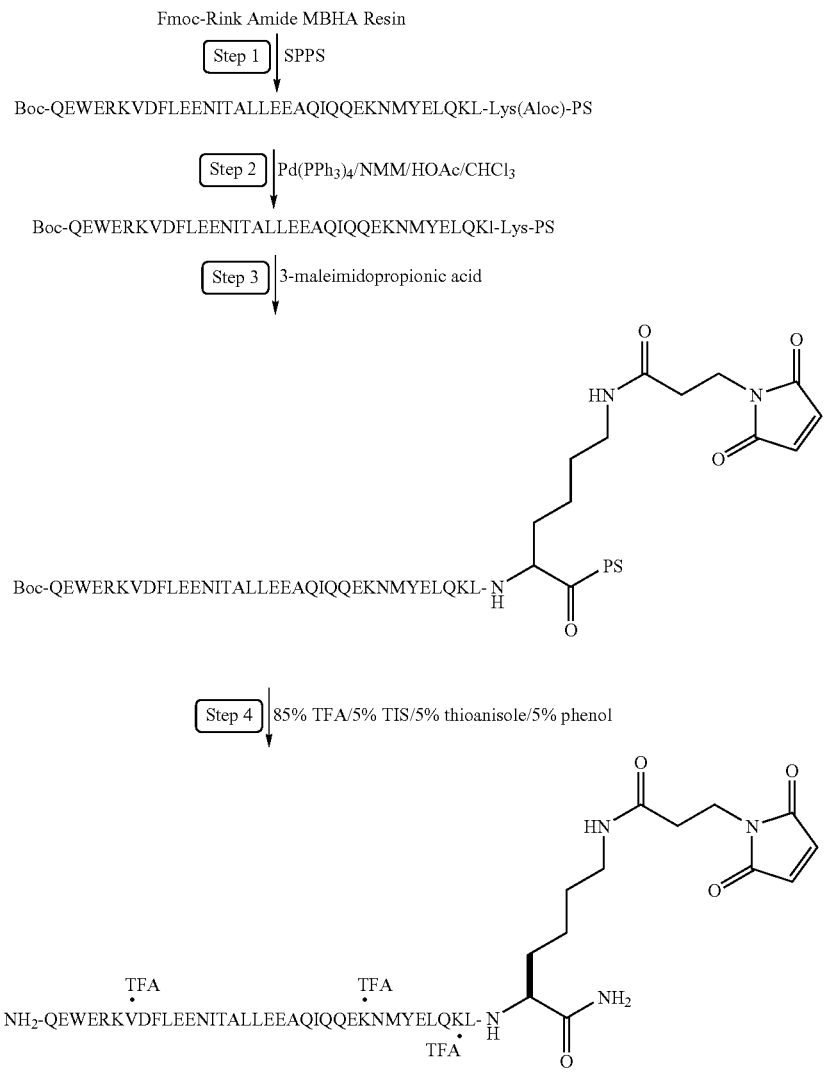

Example 23

Preparation of a Modified Anti-SIV Peptide

In this example, the peptide SEQ ID NO:66 is synthesized and modified to include a linker and maleimide group according to the synthesis scheme set forth below. As reported in U.S. Pat. Nos. 6,013,236 and 6,020,459, SEQ ID NO:66 exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu (tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu (tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Fmoc-Arg(Pbf)-OH, Fmoc-Glu(tBu)-OH, Fmoc-Trp(Boc)-OH, Fmoc-Glu(tBu)-OH Boc-Lys(Aloc)-OH. They are dissolved in N,N-dimethylformamide (DMF) and, according to the sequence, activated using O-benzotriazol-1-yl-N,N,N',N'-tetramethyluronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh₃)₄ dissolved in 5 mL of CHCl₃:NMM:HOAc (18:1:0.5) for 2 h (Step 2). The resin is then washed with CHCl₃ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et₂O (Step 4). The product is purified by preparative reversed phased HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

sequentially added to resin: Fmoc-Lys(Aloc)-OH, Fmoc-Ser(tBu)-OH, Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH,

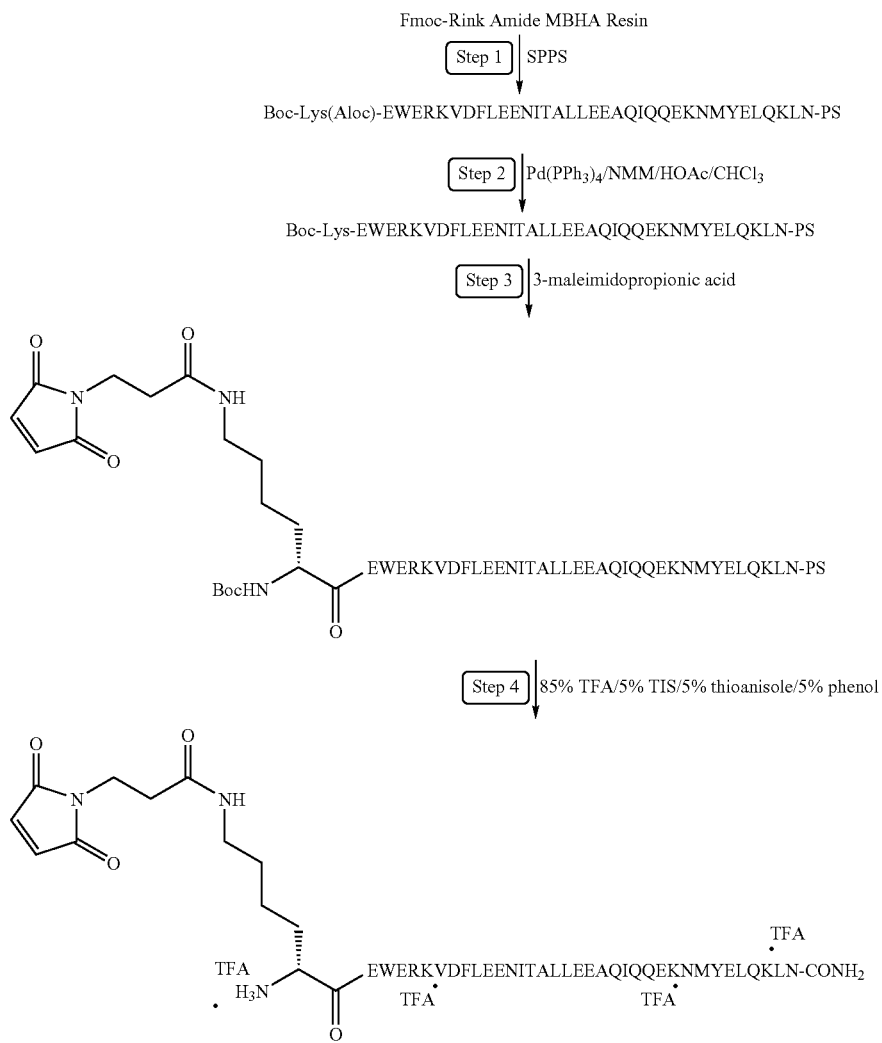

Example 24

Preparation of a Modified Anti-SIV Peptide

In this example, the peptide SEQ ID NO:67 is synthesized and modified to include a linker and maleimide group according to the synthesis scheme set forth below. As reported in U.S. Pat. Nos. 6,013,236 and 6,020,459, SEQ ID NO:67 exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Fmoc-Arg(Pbf)-OH, Fmoc-Glu(tBu)-OH, Fmoc-Trp(Boc)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh₃)₄ dissolved in 5 mL of CHCl₃:NMM:HOAc (18:1:0.5) for 2 h (Step 2). The resin is then washed with CHCl₃

(6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/ 5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

Example 25

Preparation of a Modified Anti-SIV Peptide

In this example, the peptide SEQ ID NO:68 is synthesized and modified to include a linker and maleimide group according to the synthesis scheme set forth below. As reported in U.S. Pat. Nos. 6,013,236 and 6,020,459, SEQ ID NO:68 exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Trp(Boc)-OH, Fmoc-Ser(tBu)-OH, Fmoc-Asn(Trt)-OH, Fmoc-Leu-OH, Fmoc-Lys

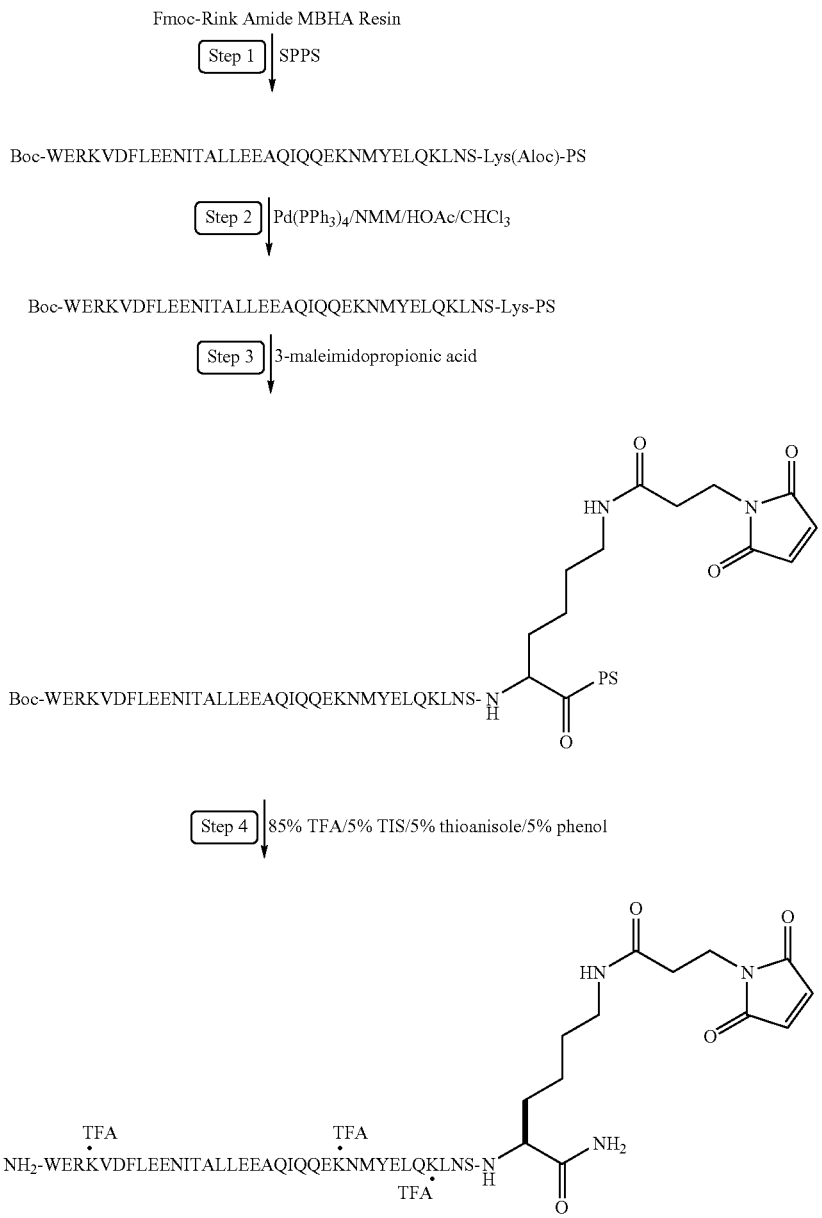

(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Fmoc-Arg(Pbf)-OH, Fmoc-Glu(tBu)-OH Boc-Lys(Aloc)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

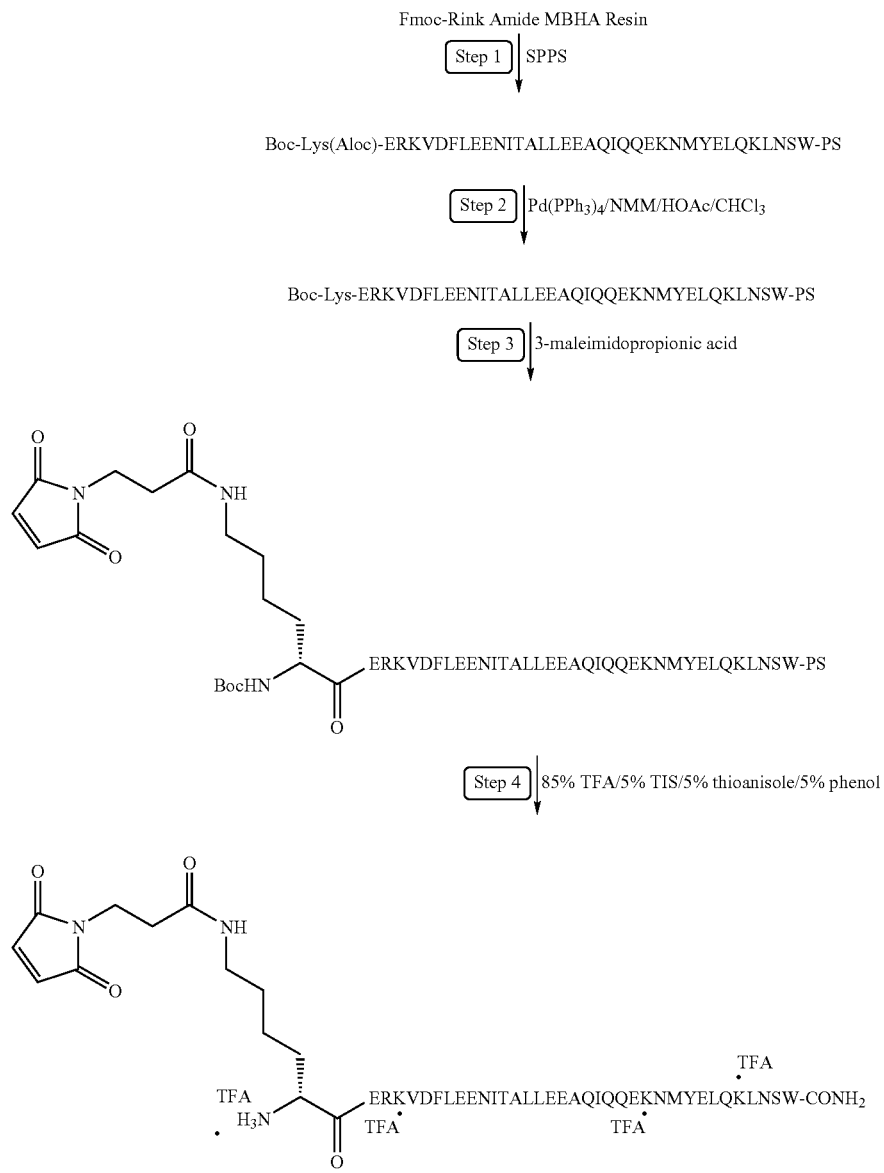

Example 26

Preparation of a Modified Anti-SIV Peptide

In this example, the peptide SEQ ID NO:69 is synthesized and modified to include a linker and maleimide group according to the synthesis scheme set forth below. As reported in U.S. Pat. Nos. 6,013,236 and 6,020,459, SEQ ID NO:69 exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Asp(tBu)-OH, Fmoc-Trp(Boc)-OH, Fmoc-Ser(tBu)-OH, Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Fmoc-Arg(Pbf)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

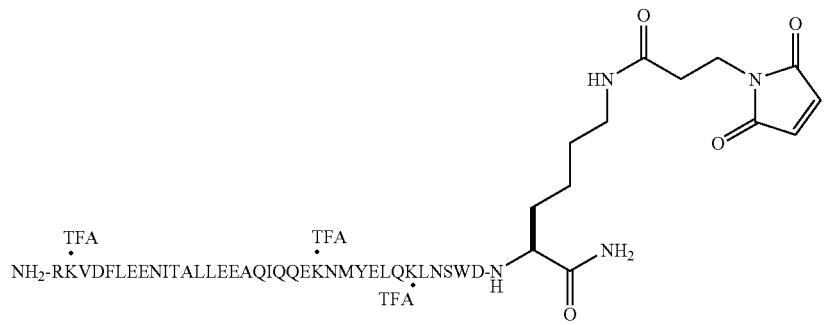

Example 27

Preparation of a Modified Anti-SIV Peptide

In this example, the peptide SEQ ID NO:70. is synthesized and modified to include a linker and maleimide group according to the synthesis scheme set forth below. As reported in U.S. Pat. Nos. 6,013,236 and 6,020,459, SEQ ID NO:70 exhibits potent antiviral activity as a crude peptide against simian immunodeficiency virus (SIV).

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Val-OH, Fmoc-Asp(tBu)-OH, Fmoc-Trp(Boc)-OH, Fmoc-Ser(tBu)-OH, Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH, Fmoc-Lys(Boc)-OH, Boc-Lys(Aloc)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10µ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

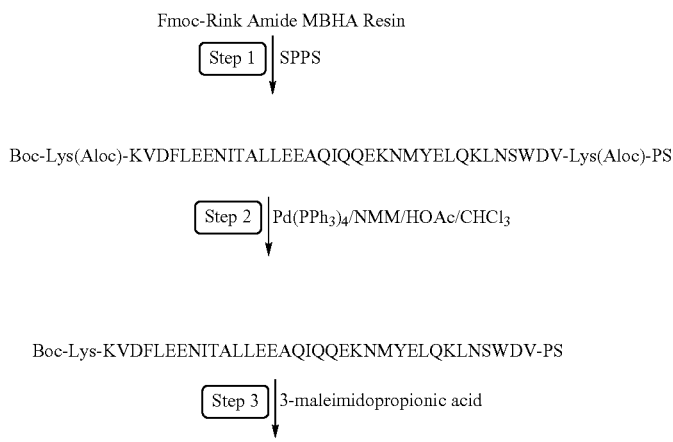

-continued

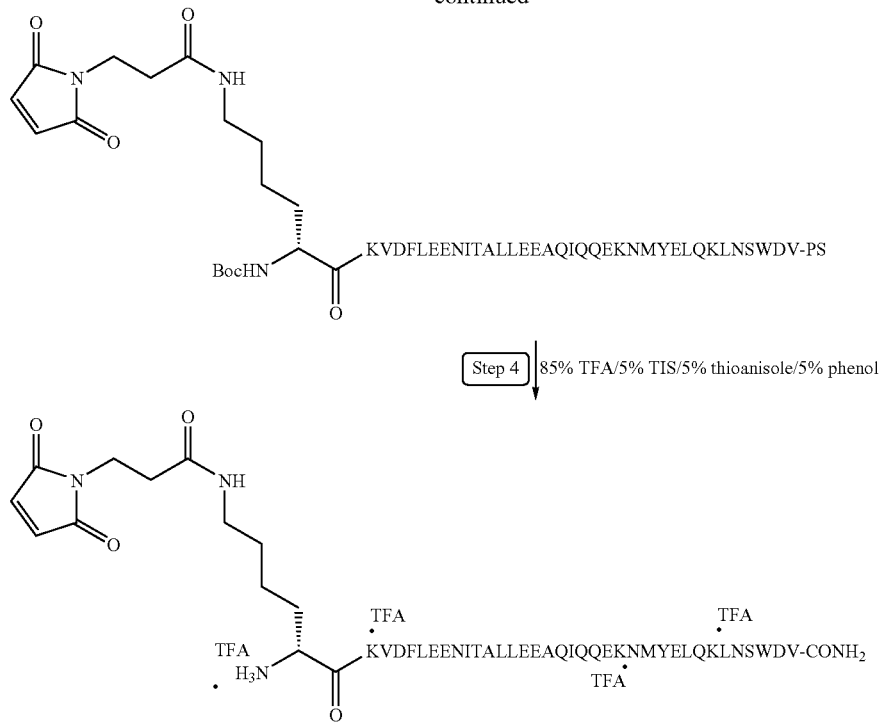

Example 28

Preparation of a Modified Anti-SIV Peptide

In this example, the peptide SEQ ID NO:71 is synthesized and modified to include a linker and maleimide group according to the synthesis scheme set forth below. As reported in U.S. Pat. Nos. 6,013,236 and 6,020,459, SEQ ID NO:71 exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Phe-OH, Fmoc-Val-OH, Fmoc-Asp(tBu)-OH, Fmoc-Trp(Boc)-OH, Fmoc-Ser(tBu)-OH, Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH, Fmoc-Val-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin is then washed with $CHCl_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$ (Step 4). The product is purified by preparative reversed phased HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

-continued
Boc-VDFLEENITALLEEAQIQQEKNMYELQKLNSWDVF-Lys(Aloc)-PS

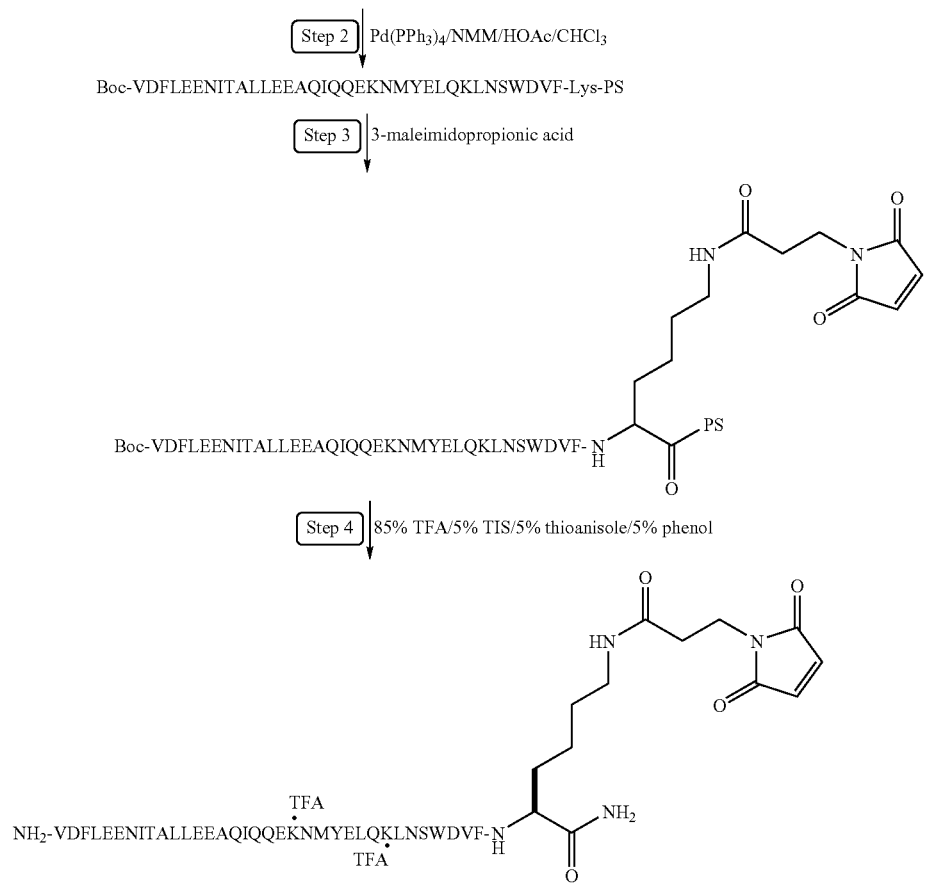

Example 29

Preparation of a Modified Anti-SIV Peptide

In this example, the peptide SEQ ID NO:72 is synthesized and modified to include a linker and maleimide group according to the synthesis scheme set forth below. As reported in U.S. Pat. Nos. 6,013,236 and 6,020,459, SEQ ID NO:72 exhibits potent antiviral activity as a crude peptide against simian immunodeficiency virus (SIV).

Solid phase peptide synthesis of the modified peptide on a 100 µmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Gly-OH, Fmoc-Phe-OH, Fmoc-Val-OH, Fmoc-Asp(tBu)-OH, Fmoc-Trp(Boc)-OH, Fmoc-Ser(tBu)-OH, Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH, Fmoc-Asp(tBu)-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

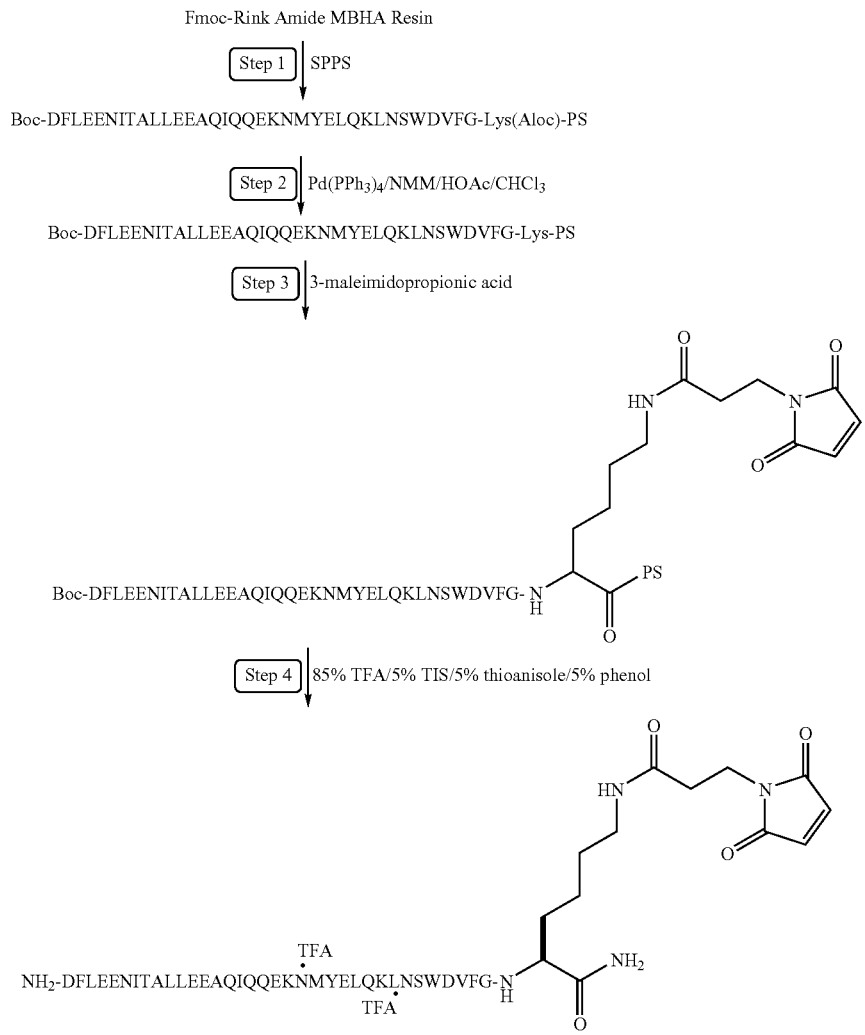

Example 30

Preparation of a Modified Anti-SIV Peptide

In this example, the peptide SEQ ID NO:73 is synthesized and modified to include a linker and maleimide group according to the synthesis scheme set forth below. As reported in U.S. Pat. Nos. 6,013,236 and 6,020,459, SEQ ID NO:73 exhibits potent antiviral activity as a crude peptide against simian immunodeficiency virus (SIV).

Solid phase peptide synthesis of the modified peptide on a 100 μmole scale is performed using manual solid-phase synthesis, a Symphony Peptide Synthesizer and Fmoc protected Rink Amide MBHA. The following protected amino acids are sequentially added to resin: Fmoc-Lys(Aloc)-OH, Fmoc-Asn(Trt)-OH, Fmoc-Gly-OH, Fmoc-Phe-OH, Fmoc-Val-OH, Fmoc-Asp(tBu)-OH, Fmoc-Trp(Boc)-OH, Fmoc-Ser(tBu)-OH, Fmoc-Asn(Trt)-OH, Fmoc-Leu-OH, Fmoc-Lys(Boc)-OH, Fmoc-Gln(Trt)-OH, Fmoc-Leu-OH, Fmoc-Glu(tBu)-OH, Fmoc-Tyr(tBu)-OH, Fmoc-Met-OH, Fmoc-Asn(Trt)-OH, Fmoc-Lys(Boc)-OH, Fmoc-Glu(tBu)-OH, Fmoc-Gln(Trt)-OH, Fmoc-Gln(Trt)-OH, Fmoc-Ile-OH, Fmoc-Gln(Trt)-OH, Fmoc-Ala-OH, Fmoc-Glu(tBu)-OH, Fmoc-Glu(tBu)-OH, Fmoc-Leu-OH, Fmoc-Leu-OH, Fmoc-Ala-OH, Fmoc-Thr(tBu)-OH, Fmoc-Ile-OH, Fmoc-Asn(Trt)-OH, Fmoc-Glu(tBu)-OH, Fmoc-Glu(tBu)-OH, Fmoc-Leu-OH, Fmoc-Phe-OH. They are dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes (step 1). The selective deprotection of the Lys (Aloc) group is performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin is then washed with CHCl$_3$ (6×5 mL), 20% HOAc in DCM (6×5 mL), DCM (6×5 mL), and DMF (6×5 mL). The synthesis is then re-automated for the addition of the 3-maleimidopropionic acid (Step 3). Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold Et$_2$O (Step 4). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ 214 and 254 nm to afford the desired modified peptide (i.e., DAC) in >95% purity, as determined by RP-HPLC.

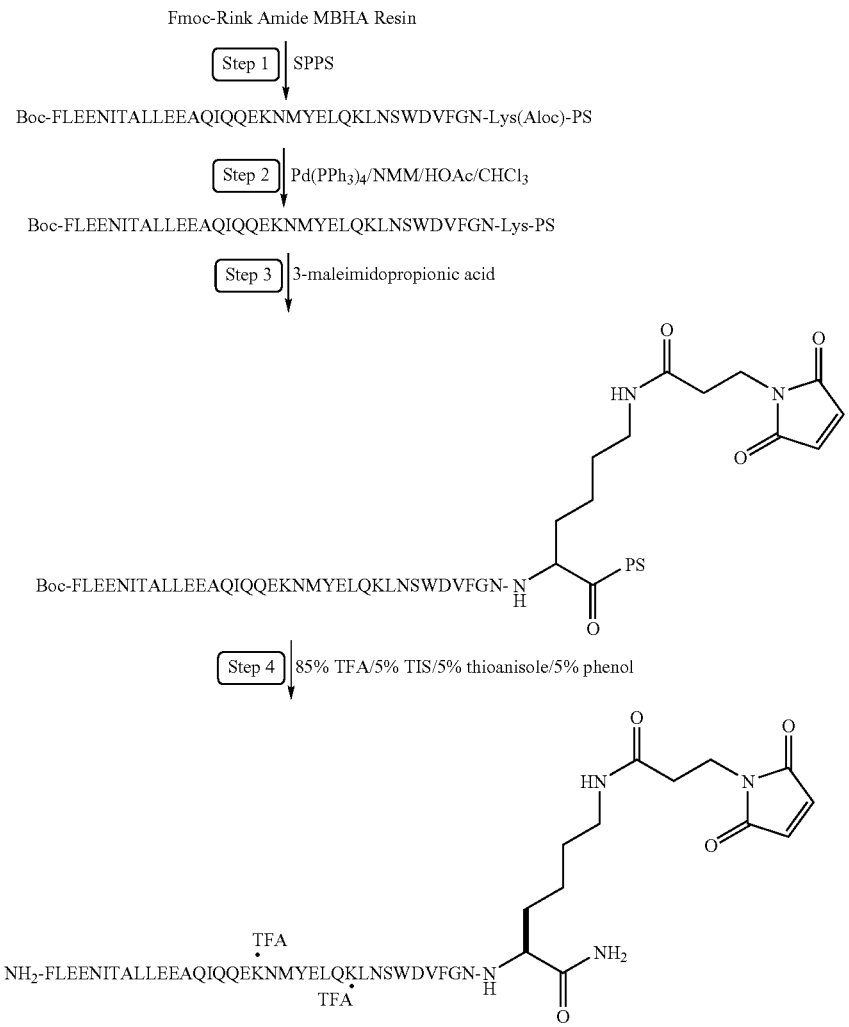

While certain embodiments of the invention have been described and exemplified, those having ordinary skill in the art will understand that the invention is not intended to be limited to the specifics of any of these embodiments, but is rather defined by the accompanying claims.

TABLE 2

| DP178 CARBOXY TRUNCATIONS | |
|---|---|
| YTS | |
| YTSL | |
| YTSLI | |
| YTSLIH | SEQ ID NO:116 |
| YTSLIHS | SEQ ID NO:115 |
| YTSLIHSL | SEQ ID NO:114 |
| YTSLIHSLI | SEQ ID NO:113 |
| YTSLIHSLIE | SEQ ID NO:112 |
| YTSLIHSLIEE | SEQ ID NO:111 |

TABLE 2-continued

| DP178 CARBOXY TRUNCATIONS | |
|---|---|
| YTSLIHSLIEES | SEQ ID NO:110 |
| YTSLIHSLIEESQ | SEQ ID NO:109 |
| YTSLIHSLIEESQN | SEQ ID NO:108 |
| YTSLIHSLIEESQNQ | SEQ ID NO:107 |
| YTSLJHSLJEESQNQQ | SEQ ID NO:106 |
| YTSLIHSLIEESQNQQE | SEQ ID NO:105 |
| YTSLIHSLIEESQNQQEK | SEQ ID NO:104 |
| YTSLIHSLIEESQNQQEKN | SEQ ID NO:103 |
| YTSLIHSLIEESQNQQEKNE | SEQ ID NO:102 |
| YTSLIHSLIEESQNQQEKNEQ | SEQ ID NO:101 |
| YTSLIHSLIEESQNQQEKNEQE | SEQ ID NO:100 |

TABLE 2-continued

DP178 CARBOXY TRUNCATIONS

| | |
|---|---|
| YTSLIHSLIEESQNQQEKNEQEL | SEQ ID NO:99 |
| YTSLIHSLIEESQNQQEKNEQELL | SEQ ID NO:98 |
| YTSLIHSLIEESQNQQEKNEQELLE | SEQ ID NO:97 |
| YTSLIHSLIEESQNQQEKNEQELLEL | SEQ ID NO:96 |
| YTSLIHSLIEESQNQQEKNEQELLELD | SEQ ID NO:95 |
| YTSLIHSLIEESQNQQEKNEQELLELDK | SEQ ID NO:94 |
| YTSLIHSLIEESQNQQEKNEQELLELDKW | SEQ ID NO:93 |
| YTSLIHSLIEESQNQQEKNEQELLELDKWA | SEQ ID NO:92 |
| YTSLIHSLIEESQNQQEKNEQELLELDKWAS | SEQ ID NO:91 |
| YTSLIHSLIEESQNQQEKNEQELLELDKWASL | SEQ ID NO:90 |
| YTSLIHSLIEESQNQQEKNEQELLELDKWASLW | SEQ ID NO:89 |
| YTSLIHSLIEESQNQQEKNEQELLELDKWASLWN | SEQ ID NO:88 |
| YTSLIHSLIEESQNQQEKNEQELLELDKWASLWNW | SEQ ID NO:87 |
| YTSLIHSLIEESQNQQEKNEQELLELDKWASLWNWF | SEQ ID NO:1 |

The one letter amino acid code of Table 1 is used.

TABLE 3

DP178 AMINO TRUNCATIONS

| | |
|---|---|
| NWF | |
| WNWF | |
| LWNWF | |
| SLWNWF | SEQ ID NO:146 |
| ASLWNWF | SEQ ID NO:145 |
| WASLWNWF | SEQ ID NO:144 |
| KWASLWNWF | SEQ ID NO:143 |
| DKWASLWNWF | SEQ ID NO:142 |
| LDKWASLWNWF | SEQ ID NO:141 |
| ELDKWASLWNWF | SEQ ID NO:140 |
| LELDKWASLWNWF | SEQ ID NO:139 |
| LLELDKWASLWNWF | SEQ ID NO:138 |
| ELLELDKWASLWNWF | SEQ ID NO:137 |
| QELLELDKWASLWNWF | SEQ ID NO:136 |
| EQELLELDKWASLWNWF | SEQ ID NO:135 |
| NEQELLELDKWASLWNWF | SEQ ID NO:134 |
| KNEQELLELDKWASLWNWF | SEQ ID NO:133 |
| EKNEQELLELDKWASLWNWF | SEQ ID NO:132 |
| QEKNEQELLELDKWASLWNWF | SEQ ID NO:131 |
| QQEKNEQELLELDKWASLWNWF | SEQ ID NO:130 |
| NQQEKNEQELLELDKWASLWNWF | SEQ ID NO:129 |

TABLE 3-continued

DP178 AMINO TRUNCATIONS

| | |
|---|---|
| QNQQEKNEQELLELDKWASLWNWF | SEQ ID NO:128 |
| SQNQQEKNEQELLELDKWASLWNWF | SEQ ID NO:127 |
| ESQNQQEKNEQELLELDKWASLWNWF | SEQ ID NO:126 |
| EESQNQQEKNEQELLELDKWASLWNWF | SEQ ID NO:125 |
| IEESQNQQEKNEQELLELDKWASLWNWF | SEQ ID NO:124 |
| LIEESQNQQEKNEQELLELDKWASLWNWF | SEQ ID NO:123 |
| SLIEESQNQQEKNEQELLELDKWASLWNWF | SEQ ID NO:122 |
| HSLIEESQNQQEKNEQELLELDKWASLWNWF | SEQ ID NO:121 |
| IHSLIEESQNQQEKNEQELLELDKWASLWNWF | SEQ ID NO:120 |
| LIHSLIEESQNQQEKNEQELLELDKWASLWNWF | SEQ ID NO:119 |
| SLIHSLIEESQNQQEKNEQELLELDKWASLWNWF | SEQ ID NO:118 |
| TSLIHSLIEESQNQQEKNEQELLELDKWASLWNWF | SEQ ID NO:117 |
| YTSLIHSLIEESQNQQEKNEQELLELDKWASLWNWF | SEQ ID NO:1 |

The one letter amino acid code of Table 1 is used.

TABLE 4

DP107 CARBOXY TRUNCATIONS

| | |
|---|---|
| NNL | |
| NNLL | |
| NNLLR | |
| NNLLRA | SEQ ID NO:178 |
| NNLLRAI | SEQ ID NO:177 |
| NNLLRAIE | SEQ ID NO:176 |
| NNLLRAIEA | SEQ ID NO:175 |
| NNLLRAIEAQ | SEQ ID NO:174 |
| NNLLRAIEAQQ | SEQ ID NO:173 |
| NNLLRAIEAQQH | SEQ ID NO:172 |
| NNLLRAIEAQQHL | SEQ ID NO:171 |
| NNLLRAIEAQQHLL | SEQ ID NO:170 |
| NNLLRAIEAQQHLLQ | SEQ ID NO:169 |
| NNLLRAIEAQQHLLQL | SEQ ID NO:168 |
| NNLLRAIEAQQHLLQLT | SEQ ID NO:167 |
| NNLLRAIEAQQHLLQLTV | SEQ ID NO:166 |
| NNLLRAIEAQQHLLQLTVW | SEQ ID NO:165 |
| NNLLRAIEAQQHLLQLTVWQ | SEQ ID NO:164 |
| NNLLRAIEAQQHLLQLTVWQI | SEQ ID NO:163 |
| NNLLRAIEAQQHLLQLTVWQIK | SEQ ID NO:162 |
| NNLLRAIEAQQHLLQLTVWQIKQ | SEQ ID NO:161 |

TABLE 4-continued

DP107 CARBOXY TRUNCATIONS

| | |
|---|---|
| NNLLRAIEAQQHLLQLTVWQIKQL | SEQ ID NO:160 |
| NNLLRAIEAQQHLLQLTVWQIKQLQ | SEQ ID NO:159 |
| NNLLRAIEAQQHLLQLTVWQIKQLQA | SEQ ID NO:158 |
| NNLLRAIEAQQHLLQLTVWQIKQLQAR | SEQ ID NO:157 |
| NNLLRAIEAQQHLLQLTVWQIKQLQARI | SEQ ID NO:156 |
| NNLLRAIEAQQHLLQLTVWQIKQLQARIL | SEQ ID NO:155 |
| NNLLRAIEAQQHLLQLTVWQIKQLQARILA | SEQ ID NO:154 |
| NNLLRAIEAQQHLLQLTVWQIKQLQARILAV | SEQ ID NO:153 |
| NNLLRAIEAQQHLLQLTVWQIKQLQARILAVE | SEQ ID NO:152 |
| NNLLRAIEAQQHLLQLTVWQIKQLQARILAVER | SEQ ID NO:151 |
| NNLLRAIEAQQHLLQLTVWQIKQLQARILAVERY | SEQ ID NO:150 |
| NNLLRAIEAQQHLLQLTVWQIKQLQARILAVERYL | SEQ ID NO:149 |
| NNLLRAIEAQQHLLQLTVWQIKQLQARILAVERYLK | SEQ ID NO:148 |
| NNLLRAIEAQQHLLQLTVWQIKQLQARILAVERYLKD | SEQ ID NO:147 |
| NNLLRAIEAQQHLLQLTVWQIKQLQARILAVERYLKDQ | SEQ ID NO:2 |

The one letter amino acid code of Table 1 is used.

TABLE 5

DP107 AMINO TRUNCATIONS

| | |
|---|---|
| KDQ | |
| LKDQ | |
| YLKDQ | |
| RYLKDQ | SEQ ID NO:210 |
| ERYLKDQ | SEQ ID NO:209 |
| VERYLKDQ | SEQ ID NO:208 |
| AVERYLKDQ | SEQ ID NO:207 |
| LAVERYLKDQ | SEQ ID NO:206 |
| ILAVERYLKDQ | SEQ ID NO:205 |
| RILAVERYLKDQ | SEQ ID NO:204 |
| ARILAVERYLKDQ | SEQ ID NO:203 |
| QARILAVERYLKDQ | SEQ ID NO:202 |
| LQARILAVERYLKDQ | SEQ ID NO:201 |
| QLQARILAVERYLKDQ | SEQ ID NO:200 |
| KQLQARILAVERYLKDQ | SEQ ID NO:199 |
| IKQLQARILAVERYLKDQ | SEQ ID NO:198 |
| QIKQLQARILAVERYLKDQ | SEQ ID NO:197 |
| WQIKQLQARILAVERYLKDQ | SEQ ID NO:196 |
| VWQIKQLQARILAVERYLKDQ | SEQ ID NO:195 |
| TVWQIKQLQARILAVERYLKDQ | SEQ ID NO:194 |

TABLE 5-continued

DP107 AMINO TRUNCATIONS

| | |
|---|---|
| LTVWQIKQLQARILAVERYLKDQ | SEQ ID NO:193 |
| QLTVWQIKQLQARILAVERYLKDQ | SEQ ID NO:192 |
| LQLTVWQIKQLQARILAVERYLKDQ | SEQ ID NO:191 |
| LLQLTVWQIKQLQARILAVERYLKDQ | SEQ ID NO:190 |
| HLLQLTVWQIKQLQARILAVERYLKDQ | SEQ ID NO:189 |
| QHLLQLTVWQIKQLQARILAVERYLKDQ | SEQ ID NO:188 |
| QQHLLQLTVWQIKQLQARILAVERYLKDQ | SEQ ID NO:187 |
| AQQHLLQLTVWQIKQLQARILAVERYLKDQ | SEQ ID NO:186 |
| EAQQHLLQLTVWQIKQLQARILAVERYLKDQ | SEQ ID NO:185 |
| IEAQQHLLQLTVWQIKQLQARILAVERYLKDQ | SEQ ID NO:184 |
| AIEAQQHLLQLTVWQIKQLQARILAVERYLKDQ | SEQ ID NO:183 |
| RAIEAQQHLLQLTVWQIKQLQARILAVERYLKDQ | SEQ ID NO:182 |
| LRAIEAQQHLLQLTVWQIKQLQARILAVERYLKDQ | SEQ ID NO:181 |
| LLRAIEAQQHLLQLTVWQIKQLQARILAVERYLKDQ | SEQ ID NO:180 |
| NLLRAIEAQQHLLQLTVWQIKQLQARILAVERYLKDQ | SEQ ID NO:179 |
| NNLLRAIEAQQHLLQLTVWQIKQLQARILAVERYLKDQ | SEQ ID NO:2 |

The one letter amino acid code of Table 1 is used.

TABLE 6

HIV-2$_{NIHZ}$ DP178 analog carboxy truncations

| | |
|---|---|
| LEA | |
| LEAN | |
| LEANI | |
| LEANIS | SEQ ID NO:240 |
| LEANISQ | SEQ ID NO:239 |
| LEANISQS | SEQ ID NO:238 |
| LEANISQSL | SEQ ID NO:237 |
| LEANISQSLE | SEQ ID NO:236 |
| LEANISQSLEQ | SEQ ID NO:235 |
| LEANISQSLEQA | SEQ ID NO:234 |
| LEANISQSLEQAQ | SEQ ID NO:233 |
| LEANISQSLEQAQI | SEQ ID NO:232 |
| LEANISQSLEQAQIQ | SEQ ID NO:231 |
| LEANISQSLEQAQIQQ | SEQ ID NO:230 |
| LEANISQSLEQAQIQQE | SEQ ID NO:229 |
| LEANISQSLEQAQIQQEK | SEQ ID NO:228 |
| LEANISQSLEQAQIQQEKN | SEQ ID NO:227 |
| LEANISQSLEQAQIQQEKNM | SEQ ID NO:226 |

TABLE 6-continued

HIV-2_NIHZ DP178 analog carboxy truncations

| | |
|---|---|
| LEANISQSLEQAQIQQEKNMY | SEQ ID NO:225 |
| LEANISQSLEQAQIQQEKNMYE | SEQ ID NO:224 |
| LEANISQSLEQAQIQQEKNMYEL | SEQ ID NO:223 |
| LEANISQSLEQAQIQQEKNMYELQ | SEQ ID NO:222 |
| LEANISQSLEQAQIQQEKNMYELQK | SEQ ID NO:221 |
| LEANISQSLEQAQIQQEKNMYELQKL | SEQ ID NO:220 |
| LEANISQSLEQAQIQQEKNMYELQKLN | SEQ ID NO:219 |
| LEANISQSLEQAQIQQEKNMYELQKLNS | SEQ ID NO:218 |
| LEANISQSLEQAQIQQEKNMYELQKLNSW | SEQ ID NO:217 |
| LEANISQSLEQAQIQQEKNMYELQKLNSWD | SEQ ID NO:216 |
| LEANISQSLEQAQIQQEKNMYELQKLNSWDV | SEQ ID NO:215 |
| LEANISQSLEQAQIQQEKNMYELQKLNSWDVF | SEQ ID NO:214 |
| LEANISQSLEQAQIQQEKNMYELQKLNSWDVFT | SEQ ID NO:213 |
| LEANISQSLEQAQIQQEKNMYELQKLNSWDVFTN | SEQ ID NO:212 |
| LEANISQSLEQAQIQQEKNMYELQKLNSWDVFTNW | SEQ ID NO:211 |
| LEANISQSLEQAQIQQEKNMYELQKLNSWDVFTNWL | SEQ ID NO:7 |

The one letter amino acid code of Table 1 is used.

TABLE 7

HIV-2_NIHZ DP178 analog amino truncations

| | |
|---|---|
| NWL | |
| TNWL | |
| FTNWL | |
| VFTNWL | SEQ ID NO:270 |
| DVFTNWL | SEQ ID NO:269 |
| WDVFTNWL | SEQ ID NO:268 |
| SWDVFTNWL | SEQ ID NO:267 |
| NSWDVFTNWL | SEQ ID NO:266 |
| LNSWDVFTNWL | SEQ ID NO:265 |
| KLNSWDVFTNWL | SEQ ID NO:264 |
| QKLNSWDVFTNWL | SEQ ID NO:263 |
| LQKLNSWDVFTNWL | SEQ ID NO:262 |
| ELQKLNSWDVFTNWL | SEQ ID NO:261 |
| YELQKLNSWDVFTNWL | SEQ ID NO:260 |
| MYELQKLNSWDVFTNWL | SEQ ID NO:259 |
| NMYELQKLNSWDVFTNWL | SEQ ID NO:258 |
| KNMYELQKLNSWDVFTNWL | SEQ ID NO:257 |
| EKNMYELQKLNSWDVFTNWL | SEQ ID NO:256 |
| QEKNMYELQKLNSWDVFTNWL | SEQ ID NO:255 |
| QQEKNMYELQKLNSWDVFTNWL | SEQ ID NO:254 |
| IQQEKNMYELQKLNSWDVFTNWL | SEQ ID NO:253 |
| QIQQEKNMYELQKLNSWDVFTNWL | SEQ ID NO:252 |
| AQIQQEKNMYELQKLNSWDVFTNWL | SEQ ID NO:251 |
| QAQIQQEKNMYELQKLNSWDVFTNWL | SEQ ID NO:250 |
| EQAQIQQEKNMYELQKLNSWDVFTNWL | SEQ ID NO:249 |
| LEQAQIQQEKNMYELQKLNSWDVFTNWL | SEQ ID NO:248 |
| SLEQAQIQQEKNMYELQKLNSWDVFTNWL | SEQ ID NO:247 |
| QSLEQAQIQQEKNMYELQKLNSWDVFTNWL | SEQ ID NO:246 |
| SQSLEQAQIQQEKNMYELQKLNSWDVFTNWL | SEQ ID NO:245 |
| ISQSLEQAQIQQEKNMYELQKLNSWDVFTNWL | SEQ ID NO:244 |
| NISQSLEQAQIQQEKNMYELQKLNSWDVFTNWL | SEQ ID NO:243 |
| ANISQSLEQAQIQQEKNMYELQKLNSWDVFTNWL | SEQ ID NO:242 |
| EANISQSLEQAQIQQEKNMYELQKLNSWDVFTNWL | SEQ ID NO:241 |
| LEANISQSLEQAQIQQEKNMYELQKLNSWDVFTNWL | SEQ ID NO:7 |

The one letter amino acid code of Table 1 is used.

TABLE 8

RESPIRATORY SYNCYTIAL VIRUS (RSV) DP107 F2 REGION ANALOG CARBOXY TRUNCATIONS

| | |
|---|---|
| YTS | |
| YTSV | |
| YTSVI | |
| YTSVIT | SEQ ID NO:312 |
| YTSVITI | SEQ ID NO:311 |
| YTSVITIE | SEQ ID NO:310 |
| YTSVITIEL | SEQ ID NO:309 |

TABLE 8-continued

RESPIRATORY SYNCYTIAL VIRUS (RSV) DP107 F2
REGION ANALOG CARBOXY TRUNCATIONS

| Sequence | SEQ ID |
|---|---|
| YTSVITIELS | SEQ ID NO:308 |
| YTSVITIELSN | SEQ ID NO:307 |
| YTSVITIELSNI | SEQ ID NO:306 |
| YTSVITIELSNIK | SEQ ID NO:305 |
| YTSVITIELSNIKE | SEQ ID NO:304 |
| YTSVITIELSNIKEN | SEQ ID NO:303 |
| YTSVITIELSNIKENK | SEQ ID NO:302 |
| YTSVITIELSNIKENKC | SEQ ID NO:301 |
| YTSVITIELSNIKENKCN | SEQ ID NO:300 |
| YTSVITIELSNIKENKCNG | SEQ ID NO:299 |
| YTSVITIELSNIKENKCNGT | SEQ ID NO:298 |
| YTSVITIELSNIKENKCNGTD | SEQ ID NO:297 |
| YTSVITIELSNIKENKCNGTDA | SEQ ID NO:296 |
| YTSVITIELSNIKENKCNGTDAK | SEQ ID NO:295 |
| YTSVITIELSNIKENKCNGTDAKV | SEQ ID NO:294 |
| YTSVITIELSNIKENKCNGTDAKVK | SEQ ID NO:293 |
| YTSVITIELSNIKENKCNGTDAKVKL | SEQ ID NO:292 |
| YTSVITIELSNIKENKCNGTDAKVKLI | SEQ ID NO:291 |
| YTSVITIELSNIKENKCNGTDAKVKLIK | SEQ ID NO:290 |
| YTSVITIELSNIKENKCNGTDAKVKLIKQ | SEQ ID NO:289 |
| YTSVITIELSNIKENKCNGTDAKVKLIKQE | SEQ ID NO:288 |
| YTSVITIELSNIKENKCNGTDAKVKLIKQEL | SEQ ID NO:287 |
| YTSVITIELSNIKENKCNGTDAKVKLIKQELD | SEQ ID NO:286 |
| YTSVITIELSNIKENKCNGTDAKVKLIKQELDK | SEQ ID NO:285 |
| YTSVITIELSNIKENKCNGTDAKVKLIKQELDKY | SEQ ID NO:284 |
| YTSVITIELSNIKENKCNGTDAKVKLIKQELDKYK | SEQ ID NO:283 |
| YTSVITIELSNIKENKCNGTDAKVKLIKQELDKYKN | SEQ ID NO:282 |
| YTSVITIELSNIKENKCNGTDAKVKLIKQELDKYKNA | SEQ ID NO:281 |
| YTSVITIELSNIKENKCNGTDAKVKLIKQELDKYKNAV | SEQ ID NO:280 |
| YTSVITIELSNIKENKCNGTDAKVKLIKQELDKYKNAVT | SEQ ID NO:279 |
| YTSVITIELSNIKENKCNGTDAKVKLIKQELDKYKNAVTE | SEQ ID NO:278 |
| YTSVITIELSNIKENKCNGTDAKVKLIKQELDKYKNAVTEL | SEQ ID NO:277 |
| YTSVITIELSNIKENKCNGTDAKVKLIKQELDKYKNAVTELQ | SEQ ID NO:276 |
| YTSVITIELSNIKENKCNGTDAKVKLIKQELDKYKNAVTELQL | SEQ ID NO:275 |
| YTSVITIELSNIKENKCNGTDAKVKLIKQELDKYKNAVTELQLL | SEQ ID NO:274 |
| YTSVITIELSNIKENKCNGTDAKVKLIKQELDKYKNAVTELQLLM | SEQ ID NO:273 |
| YTSVITIELSNIKENKCNGTDAKVKLIKQELDKYKNAVTELQLLMQ | SEQ ID NO:272 |

TABLE 8-continued

RESPIRATORY SYNCYTIAL VIRUS (RSV) DP107 F2 REGION ANALOG CARBOXY TRUNCATIONS

| | |
|---|---|
| YTSVITIELSNIKENKCNGTDAKVKLIKQELDKYKNAVTELQLLMQS | SEQ ID NO:271 |
| YTSVITIELSNIKENKCNGTDAKVKLIKQELDKYKNAVTELQLLMQST | SEQ ID NO:13 |

The one letter amino acid code of Table 1 is used.

TABLE 9

RESPIRATORY SYNCYTIAL VIRUS (RSV) DP107 F2 REGION ANALOG AMINO TRUNCATIONS

| | |
|---|---|
| QST | |
| MQST | |
| LMQST | |
| LLMQST | SEQ ID NO:353 |
| QLLMQST | SEQ ID NO:352 |
| LQLLMQST | SEQ ID NO:351 |
| ELQLLMQST | SEQ ID NO:350 |
| TELQLLMQST | SEQ ID NO:349 |
| VTELQLLMQST | SEQ ID NO:348 |
| AVTELQLLMQST | SEQ ID NO:347 |
| NAVTELQLLMQST | SEQ ID NO:346 |
| KNAVTELQLLMQST | SEQ ID NO:345 |
| YKNAVTELQLLMQST | SEQ ID NO:344 |
| KYKNAVTELQLLMQST | SEQ ID NO:343 |
| DKYKNAVTELQLLMQST | SEQ ID NO:342 |
| LDKYKNAVTELQLLMQST | SEQ ID NO:341 |
| ELDKYKNAVTELQLLMQST | SEQ ID NO:340 |
| QELDKYKNAVTELQLLMQST | SEQ ID NO:339 |
| KQELDKYKNAVTELQLLMQST | SEQ ID NO:338 |
| IKQELDKYKNAVTELQLLMQST | SEQ ID NO:337 |
| LIKQELDKYKNAVTELQLLMQST | SEQ ID NO:336 |
| KLIKQELDKYKNAVTELQLLMQST | SEQ ID NO:335 |
| VKLIKQELDKYKNAVTELQLLMQST | SEQ ID NO:334 |
| KVKLIKQELDKYKNAVTELQLLMQST | SEQ ID NO:333 |
| AKVKLIKQELDKYKNAVTELQLLMQST | SEQ ID NO:332 |
| DAKVKLIKQELDKYKNAVTELQLLMQST | SEQ ID NO:331 |
| TDAKVKLIKQELDKYKNAVTELQLLMQST | SEQ ID NO:330 |
| GTDAKVKLIKQELDKYKNAVTELQLLMQST | SEQ ID NO:329 |
| NGTDAKVKLIKQELDKYKNAVTELQLLMQST | SEQ ID NO:328 |
| CNGTDAKVKLIKQELDKYKNAVTELQLLMQST | SEQ ID NO:327 |
| KCNGTDAKVKLIKQELDKYKNAVTELQLLMQST | SEQ ID NO:326 |
| NKCNGTDAKVKLIKQELDKYKNAVTELQLLMQST | SEQ ID NO:325 |

TABLE 9-continued

RESPIRATORY SYNCYTIAL VIRUS (RSV) DP107 F2 REGION ANALOG AMINO TRUNCATIONS

| Sequence | ID |
|---|---|
| KENKCNGTDAKVKLIKQELDKYKNAVTELQLLMQST | SEQ ID NO:324 |
| IKENKCNGTDAKVKLIKQELDKYKNAVTELQLLMQST | SEQ ID NO:323 |
| NIKENKCNGTDAKVKLIKQELDKYKNAVTELQLLMQST | SEQ ID NO:322 |
| SNIKENKCNGTDAKVKLIKQELDKYKNAVTELQLLMQST | SEQ ID NO:321 |
| LSNIKENKCNGTDAKVKLIKQELDKYKNAVTELQLLMQST | SEQ ID NO:320 |
| ELSNIKENKCNGTDAKVKLIKQELDKYKNAVTELQLLMQST | SEQ ID NO:319 |
| IELSNIKENKCNGTDAKVKLIKQELDKYKNAVTELQLLMQST | SEQ ID NO:318 |
| TIELSNIKENKCNGTDAKVKLIKQELDKYKNAVTELQLLMQST | SEQ ID NO:317 |
| ITIELSNIKENKCNGTDAKVKLIKQELDKYKNAVTELQLLMQST | SEQ ID NO:316 |
| VITIELSNIKENKCNGTDAKVKLIKQELDKYKNAVTELQLLMQST | SEQ ID NO:315 |
| SVITIELSNIKENKCNGTDAKVKLIKQELDKYKNAVTELQLLMQST | SEQ ID NO:314 |
| TSVITIELSNIKENKCNGTDAKVKLIKQELDKYKNAVTELQLLMQST | SEQ ID NO:313 |

The one letter amino acid code of Table 1 is used.

TABLE 10

RESPIRATORY SYNCYTIAL VIRUS (RSV) F1 DP178 REGION ANALOG CARBOXY TRUNCATIONS

| Sequence | ID |
|---|---|
| FYD | |
| FYDP | |
| FYDPL | |
| FYDPLV | SEQ ID NO:385 |
| FYDPLVF | SEQ ID NO:384 |
| FYDPLVFP | SEQ ID NO:383 |
| FYDPLVFPS | SEQ ID NO:382 |
| FYDPLVFPSD | SEQ ID NO:381 |
| FYDPLVFPSDE | SEQ ID NO:380 |
| FYDPLVFPSDEF | SEQ ID NO:379 |
| FYDPLVFPSDEFD | SEQ ID NO:378 |
| FYDPLVFPSDEFDA | SEQ ID NO:377 |
| FYDPLVFPSDEFDAS | SEQ ID NO:376 |
| FYDPLVFPSDEFDASI | SEQ ID NO:375 |
| FYDPLVFPSDEFDASIS | SEQ ID NO:374 |
| FYDPLVFPSDEFDASISQ | SEQ ID NO:373 |
| FYDPLVFPSDEFDASISQV | SEQ ID NO:372 |
| FYDPLVFPSDEFDASISQVN | SEQ ID NO:371 |
| FYDPLVFPSDEFDASISQVNE | SEQ ID NO:370 |
| FYDPLVFPSDEFDASISQVNEK | SEQ ID NO:369 |
| FYDPLVFPSDEFDASISQVNEKI | SEQ ID NO:368 |
| FYDPLVFPSDEFDASISQVNEKIN | SEQ ID NO:367 |
| FYDPLVFPSDEFDASISQVNEKINQ | SEQ ID NO:366 |
| FYDPLVFPSDEFDASISQVNEKINQS | SEQ ID NO:365 |
| FYDPLVFPSDEFDASISQVNEKINQSL | SEQ ID NO:364 |
| FYDPLVFPSDEFDASISQVNEKINQSLA | SEQ ID NO:363 |
| FYDPLVFPSDEFDASISQVNEKINQSLAF | SEQ ID NO:362 |
| FYDPLVFPSDEFDASISQVNEKINQSLAFI | SEQ ID NO:361 |
| FYDPLVFPSDEFDASISQVNEKINQSLAFIR | SEQ ID NO:360 |
| FYDPLVFPSDEFDASISQVNEKINQSLAFIRK | SEQ ID NO:359 |
| FYDPLVFPSDEFDASISQVNEKINQSLAFIRKS | SEQ ID NO:358 |
| FYDPLVFPSDEFDASISQVNEKINQSLAFIRKSD | SEQ ID NO:357 |
| FYDPLVFPSDEFDASISQVNEKINQSLAFIRKSDE | SEQ ID NO:356 |
| FYDPLVFPSDEFDASISQVNEKINQSLAFIRKSDEL | SEQ ID NO:355 |
| FYDPLVFPSDEFDASISQVNEKINQSLAFIRKSDELL | SEQ ID NO:354 |

The one letter amino acid code of Table 1 is used.

TABLE 11

RESPIRATORY SYNCYTIAL VIRUS (RSV) F1 DP178 REGION ANALOG AMINO TRUNCATIONS

DELL

SDELL

TABLE 11-continued

RESPIRATORY SYNCYTIAL VIRUS (RSV) F1 DP178 REGION ANALOG AMINO TRUNCATIONS

| Sequence | |
|---|---|
| KSDELL | SEQ ID NO:416 |
| RKSDELL | SEQ ID NO:415 |
| IRKSDELL | SEQ ID NO:414 |
| FIRKSDELL | SEQ ID NO:413 |
| AFIRKSDELL | SEQ ID NO:412 |
| LAFIRKSDELL | SEQ ID NO:411 |
| SLAFIRKSDELL | SEQ ID NO:410 |
| QSLAFIRKSDELL | SEQ ID NO:409 |
| NQSLAFIRKSDELL | SEQ ID NO:408 |
| INQSLAFIRKSDELL | SEQ ID NO:407 |
| KINQSLAFIRKSDELL | SEQ ID NO:406 |
| EKINQSLAFIRKSDELL | SEQ ID NO:405 |
| NEKINQSLAFIRKSDELL | SEQ ID NO:404 |
| VNEKINQSLAFIRKSDELL | SEQ ID NO:403 |
| QVNEKINQSLAFIRKSDELL | SEQ ID NO:402 |
| SQVNEKINQSLAFIRKSDELL | SEQ ID NO:401 |
| ISQVNEKINQSLAFIRKSDELL | SEQ ID NO:400 |
| SISQVNEKINQSLAFIRKSDELL | SEQ ID NO:399 |
| ASISQVNEKINQSLAFIRKSDELL | SEQ ID NO:398 |
| DASISQVNEKINQSLAFIRKSDELL | SEQ ID NO:397 |
| FDASISQVNEKINQSLAFIRKSDELL | SEQ ID NO:396 |
| EFDASISQVNEKINQSLAFIRKSDELL | SEQ ID NO:395 |
| DEFDASISQVNEKINQSLAFIRKSDELL | SEQ ID NO:394 |
| SDEFDASISQVNEKINQSLAFIRKSDELL | SEQ ID NO:393 |
| PSDEFDASISQVNEKINQSLAFIRKSDELL | SEQ ID NO:392 |
| FPSDEFDASISQVNEKINQSLAFIRKSDELL | SEQ ID NO:391 |
| VFPSDEFDASISQVNEKINQSLAFIRKSDELL | SEQ ID NO:390 |
| LVFPSDEFDASISQVNEKINQSLAFIRKSDELL | SEQ ID NO:389 |
| PLVFPSDEFDASISQVNEKINQSLAFIRKSDELL | SEQ ID NO:388 |
| DPLVFPSDEFDASISQVNEKINQSLAFIRKSDELL | SEQ ID NO:387 |
| YDPLVFPSDEFDASISQVNEKINQSLAFIRKSDELL | SEQ ID NO:386 |

The one letter amino acid code of Table 1 is used.

TABLE 12

HUMAN PARAINFLUENZA VIRUS 3 (HPV3) F1 REGION DP178 ANALOG CARBOXY TRUNCATIONS

ITL

ITLN

ITLNN

TABLE 12-continued

HUMAN PARAINFLUENZA VIRUS 3 (HPV3) F1 REGION DP178 ANALOG CARBOXY TRUNCATIONS

| Sequence | |
|---|---|
| ITLNNS | SEQ ID NO:446 |
| ITLNNSV | SEQ ID NO:445 |
| ITLNNSVA | SEQ ID NO:444 |
| ITLNNSVAL | SEQ ID NO:443 |
| ITLNNSVALD | SEQ ID NO:442 |
| ITLNNSVALDP | SEQ ID NO:441 |
| ITLNNSVALDPI | SEQ ID NO:440 |
| ITLNNSVALDPID | SEQ ID NO:439 |
| ITLNNSVALDPIDI | SEQ ID NO:438 |
| ITLNNSVALDPIDIS | SEQ ID NO:437 |
| ITLNNSVALDPIDISI | SEQ ID NO:436 |
| ITLNNSVALDPIDISIE | SEQ ID NO:435 |
| ITLNNSVALDPIDISIEL | SEQ ID NO:434 |
| ITLNNSVALDPIDISIELN | SEQ ID NO:433 |
| ITLNNSVALDPIDISIELNK | SEQ ID NO:432 |
| ITLNNSVALDPIDISIELNKA | SEQ ID NO:431 |
| ITLNNSVALDPIDISIELNKAK | SEQ ID NO:430 |
| ITLNNSVALDPIDISIELNKAKS | SEQ ID NO:429 |
| ITLNNSVALDPIDISIELNKAKSD | SEQ ID NO:428 |
| ITLNNSVALDPIDISIELNKAKSDL | SEQ ID NO:427 |
| ITLNNSVALDPIDISIELNKAKSDLE | SEQ ID NO:426 |
| ITLNNSVALDPIDISIELNKAKSDLEE | SEQ ID NO:425 |
| ITLNNSVALDPIDISIELNKAKSDLEES | SEQ ID NO:424 |
| ITLNNSVALDPIDISIELNKAKSDLEESK | SEQ ID NO:423 |
| ITLNNSVALDPIDISIELNKAKSDLEESKE | SEQ ID NO:422 |
| ITLNNSVALDPIDISIELNKAKSDLEESKEW | SEQ ID NO:421 |
| ITLNNSVALDPIDISIELNKAKSDLEESKEWI | SEQ ID NO:420 |
| ITLNNSVALDPIDISIELNKAKSDLEESKEWIR | SEQ ID NO:419 |
| ITLNNSVALDPIDISIELNKAKSDLEESKEWIRR | SEQ ID NO:418 |
| ITLNNSVALDPIDISIELNKAKSDLEESKEWIRRS | SEQ ID NO:417 |

The one letter amino acid code of Table 1 is used.

TABLE 13

HUMAN PARAINFLUENZA VIRUS 3 (HPV3) F1 REGION DP178 ANALOG AMINO TRUNCATIONS

RRS

IRRS

WIRRS

TABLE 13-continued

| HUMAN PARAINFLUENZA VIRUS 3 (HPV3) F1 REGION DP178 ANALOG AMINO TRUNCATIONS | |
|---|---|
| EWIRRS | SEQ ID NO :475 |
| KEWIRRS | SEQ ID NO :474 |
| SKEWIRRS | SEQ ID NO :473 |
| ESKEWIRRS | SEQ ID NO :472 |
| EESKEWIRRS | SEQ ID NO :471 |
| LEESKEWIRRS | SEQ ID NO :470 |
| DLEESKEWIRRS | SEQ ID NO :469 |
| SDLEESKEWIRRS | SEQ ID NO :468 |
| KSDLEESKEWIRRS | SEQ ID NO :467 |
| AKSDLEESKEWIRRS | SEQ ID NO :466 |
| KAKSDLEESKEWIRRS | SEQ ID NO :465 |
| NKAKSDLEESKEWIRRS | SEQ ID NO :464 |
| LNKAKSDLEESKEWIRRS | SEQ ID NO :463 |
| ELNKAKSDLEESKEWIRRS | SEQ ID NO :462 |
| IELNKAKSDLEESKEWIRRS | SEQ ID NO :461 |
| SIELNKAKSDLEESKEWIRRS | SEQ ID NO :460 |
| ISIELNKAKSDLEESKEWIRRS | SEQ ID NO :459 |
| DISIELNIKAKSDLEESKEWIRRS | SEQ ID NO :458 |
| IDISIELNKAKSDLEESKEWIRRS | SEQ ID NO :457 |
| PIDISIELNKAKSDLEESKEWIRRS | SEQ ID NO :456 |
| DPIDISIELNKAKSDLEESKEWIRRS | SEQ ID NO :455 |
| LDPIDISIELNKAKSDLEESKEWIRRS | SEQ ID NO :454 |
| ALDPIDISIELNKAKSDLEESKEWIRRS | SEQ ID NO :453 |
| VALDPIDISIELNKAKSDLEESKEWIRRS | SEQ ID NO :452 |
| SVALDPIDISIELNKAKSDLEESKEWIRRS | SEQ ID NO :451 |
| NSVALDPIDISIELNKAKSDLEESKEWIRRS | SEQ ID NO :450 |
| NNSVALDPIDISIELNKAKSDLEESKEWIRRS | SEQ ID NO :449 |
| LNNSVALDPIDISIELNKAKSDLEESKEWIRRS | SEQ ID NO :448 |
| TLNNSVALDPIDISIELNKAKSDLEESKEWIRRS | SEQ ID NO :447 |

The one letter amino acid code of Table 1 is used.

TABLE 14

| HUMAN PARAINFLUENZA VIRUS 3 (HPV3) F1 REGION DP107 ANALOG CARBOXY TRUNCATIONS | |
|---|---|
| ALG | |
| ALGV | |
| ALGVA | |
| ALGVAT | SEQ ID NO:504 |
| ALGVATS | SEQ ID NO:503 |

TABLE 14-continued

| HUMAN PARAINFLUENZA VIRUS 3 (HPV3) F1 REGION DP107 ANALOG CARBOXY TRUNCATIONS | |
|---|---|
| ALGVATSA | SEQ ID NO:502 |
| ALGVATSAQ | SEQ ID NO:501 |
| ALGVATSAQI | SEQ ID NO:500 |
| ALGVATSAQIT | SEQ ID NO:499 |
| ALGVATSAQITA | SEQ ID NO:498 |
| ALGVATSAQITAA | SEQ ID NO:497 |
| ALGVATSAQITAAV | SEQ ID NO:496 |
| ALGVATSAQITAAVA | SEQ ID NO:495 |
| ALGVATSAQITAAVAL | SEQ ID NO:494 |
| ALGVATSAQITAAVALV | SEQ ID NO:493 |
| ALGVATSAQITAAVALVE | SEQ ID NO:492 |
| ALGVATSAQITAAVALVEA | SEQ ID NO:491 |
| ALGVATSAQITAAVALVEAK | SEQ ID NO:490 |
| ALGVATSAQITAAVALVEAKQ | SEQ ID NO:489 |
| ALGVATSAQITAAVALVEAKQA | SEQ ID NO:488 |
| ALGVATSAQITAAVALVEAKQAR | SEQ ID NO:487 |
| ALGVATSAQITAAVALVEAKQARS | SEQ ID NO:486 |
| ALGVATSAQITAAVALVEAKQARSD | SEQ ID NO:485 |
| ALGVATSAQITAAVALVEAKQARSDI | SEQ ID NO:484 |
| ALGVATSAQITAAVALVEAKQARSDIE | SEQ ID NO:483 |
| ALGVATSAQITAAVALVEAKQARSDIEK | SEQ ID NO:482 |
| ALGVATSAQITAAVALVEAKQARSDIEKL | SEQ ID NO:481 |
| ALGVATSAQITAAVALVEAKQARSDIEKLK | SEQ ID NO:480 |
| ALGVATSAQITAAVALVEAKQARSDIEKLKE | SEQ ID NO:479 |
| ALGVATSAQITAAVALVEAKQARSDIEKLKEA | SEQ ID NO:478 |
| ALGVATSAQITAAVALVEAKQARSDIEKLKEAI | SEQ ID NO:477 |
| ALGVATSAQITAAVALVEAKQARSDIEKLKEAIR | SEQ ID NO:476 |

The one letter amino acid code of Table 1 is used.

TABLE 15

| HUMAN PARAINFLUENZA VIRUS 3 (HPV3) F1 REGION DP107 ANALOG AMINO TRUNCATIONS | |
|---|---|
| IRD | |
| AIRD | |
| EAIRD | |
| KEAIRD | SEQ ID NO:533 |
| LKEAIRD | SEQ ID NO:532 |
| KLKEAIRD | SEQ ID NO:531 |

TABLE 15-continued

HUMAN PARAINFLUENZA VIRUS 3 (HPV3) F1 REGION DP107 ANALOG AMINO TRUNCATIONS

| | |
|---|---|
| EKLKEAIRD | SEQ ID NO:530 |
| IEKLKEAIRD | SEQ ID NO:529 |
| DIEKLKEAIRD | SEQ ID NO:528 |
| SDIEKLKEAIRD | SEQ ID NO:527 |
| RSDIEKLKEAIRD | SEQ ID NO:526 |
| ARSDIEKLKEAIRD | SEQ ID NO:525 |
| QARSDIEKLKEAIRD | SEQ ID NO:524 |
| KQARSDIEKLKEAIRD | SEQ ID NO:523 |
| AKQARSDIEKLKEAIRD | SEQ ID NO:522 |
| EAKQARSDIEKLKEAIRD | SEQ ID NO:521 |
| VEAKQARSDIEKLREAIRD | SEQ ID NO:520 |
| LVEAKQARSDIEKLKEAIRD | SEQ ID NO:519 |
| ALVEAKQARSDIEKLKEAIRD | SEQ ID NO:518 |
| VALVEAKQARSDIEKLKEAIRD | SEQ ID NO:517 |
| AVALVEAKQARSDIEKLKEAIRD | SEQ ID NO:516 |
| AAVALVEAKQARSDIEKLKEAIRD | SEQ ID NO:515 |
| TAAVALVEAKQARSDIEKLKEAIRD | SEQ ID NO:514 |
| ITAAVALVEAKQARSDIEKLKEAIRD | SEQ ID NO:513 |
| QITAAVALVEAKQARSDIEKLKEAIRD | SEQ ID NO:512 |
| AQITAAVALVEAKQARSDIEKLKEAIRD | SEQ ID NO:511 |
| SAQITAAVALVEAKQARSDIEKLKEAIRD | SEQ ID NO:510 |
| TSAQITAAVALVEAKQARSDIEKLKEAIRD | SEQ ID NO:509 |
| ATSAQITAAVALVEAKQARSDIEKLKEAIRD | SEQ ID NO:508 |
| VATSAQITAAVALVEAKQARSDIEKLKEAIRD | SEQ ID NO:507 |
| GVATSAQITAAVALVEAKQARSDIEKLKEAIRD | SEQ ID NO:506 |
| LGVATSAQITAAVALVEAKQARSDIEKLKEAIRD | SEQ ID NO:505 |

The one letter amino acid code of Table 1 is used.

TABLE 16

ANTI-RESPIRATORY SYNCYTIAL VIRUS (RSV) PEPTIDES

| | |
|---|---|
| TSVITIELSNIKENKCNGTDAKVKLIKQELDKYKN | SEQ ID NO:15 |
| SVITIELSNIKENKCNGTDAKVKLIKQELDKYKNA | SEQ ID NO:16 |
| VITIELSNIKENKCNGTDAKVKLIKQELDKYKNAV | SEQ ID NO:17 |
| VAVSKVLHLEGEVNKIALLSTNKAVVSLSNGVS | SEQ ID NO:18 |
| AVSKVLHLEGEVNKIALLSTNKAVVSLSNGVSV | SEQ ID NO:19 |
| VSKVLHLEGEVNKIALLSTNKAVVSLSNGVSVL | SEQ ID NO:20 |
| SKVLHLEGEVNKIALLSTNKAVVSLSNGVSVLT | SEQ ID NO:21 |
| KVLHLEGEVNKIALLSTNKAVVSLSNGVSVLTS | SEQ ID NO:22 |

TABLE 16-continued

ANTI-RESPIRATORY SYNCYTIAL VIRUS (RSV) PEPTIDES

| | |
|---|---|
| LEGEVNKIALLSTNKAVVSLSNGVSVLTSKVLD | SEQ ID NO:23 |
| GEVNKIALLSTNKAVVSLSNGVSVLTSKVLDLK | SEQ ID NO:24 |
| EVNKIALLSTNKAVVSLSNGVSVLTSKVLDLKN | SEQ ID NO:25 |
| VNKIALLSTNKAVVSLSNGVSVLTSKVLDLKNY | SEQ ID NO:26 |
| NKIALLSTNKAVVSLSNGVSVLTSKVLDLKNYI | SEQ ID NO:27 |
| KIALLSTNKAVVSLSNGVSVLTSKVLDLKNYID | SEQ ID NO:28 |
| IALLSTNKAVVSLSNGVSVLTSKVLDLKNYIDK | SEQ ID NO:29 |
| ALLSTNKAVVSLSNGVSVLTSKVLDLKNYIDKQ | SEQ ID NO:30 |
| VAVSKVLHLEGEVNKIALLSTNKAVVSLSNGVS | SEQ ID NO:18 |
| AVSKVLHLEGEVNKIALLSTNKAVVSLSNGVSV | SEQ ID NO:19 |
| VSKVLHLEGEVNKIALLSTNKAVVSLSNGVSVL | SEQ ID NO:20 |
| SKVLHLEGEVNKIALLSTNKAVVSLSNGVSVLT | SEQ ID NO:21 |
| KVLHLEGEVNKIALLSTNKAVVSLSNGVSVLTS | SEQ ID NO:22 |
| LEGEVNKIALLSTNKAVVSLSNGVSVLTSKVLD | SEQ ID NO:23 |
| GEVNKIALLSTNKAVVSLSNGVSVLTSKVLDLK | SEQ ID NO:24 |
| EVNKIALLSTNKAVVSLSNGVSVLTSKVLDLKN | SEQ ID NO:25 |
| VNKIALLSTNKAVVSLSNGVSVLTSKVLDLKNY | SEQ ID NO:26 |
| NKIALLSTNKAVVSLSNGVSVLTSKVLDLKNYI | SEQ ID NO:27 |
| KIALLSTNKAVVSLSNGVSVLTSKVLDLKNYID | SEQ ID NO:28 |
| IALLSTNKAVVSLSNGVSVLTSKVLDLKNYIDK | SEQ ID NO:29 |
| ALLSTNKAVVSLSNGVSVLTSKVLDLKNYIDKQ | SEQ ID NO:30 |

The one letter amino acid code of Table 1 is used.

TABLE 17

ANTI-HUMAN PARAINFLUENZA VIRUS 3 (HPV3) PEPTIDES

| | |
|---|---|
| TLNNSVALDPIDISIELNKAKSDLEESKEWIRRSN | SEQ ID NO:33 |
| LNNSVALDPIDISIELNKAKSDLEESKEWIRRSNQ | SEQ ID NO:34 |
| NNSVALDPIDISIELNKAKSDLEESKEWIRRSNQK | SEQ ID NO:35 |
| NSVALDPIDISIELNKAKSDLEESKEWIRRSNQKL | SEQ ID NO:36 |
| SVALDPIDISIELNKAKSDLEESKEWIRRSNQKLD | SEQ ID NO:37 |
| VALDPIDISIELNKAKSDLEESKEWIRRSNQKLDS | SEQ ID NO:38 |
| ALDPIDISIELNKAKSDLEESKEWIRRSNQKLDSI | SEQ ID NO:39 |
| LDPIDISIELNKAKSDLEESKEWIRRSNQKLDSIG | SEQ ID NO:40 |
| DPIDISIELNKAKSDLEESKEWIRRSNQKLDSIGN | SEQ ID NO:41 |
| PIDISIELNKAKSDLEESKEWIRRSNQKLDSIGNW | SEQ ID NO:42 |
| IDISIELNKAKSDLEESKEWIRRSNQKLDSIGNWH | SEQ ID NO:43 |
| DISIELNKAKSDLEESKEWIRRSNQKLDSIGNWHQ | SEQ ID NO:44 |
| ISIELNKAKSDLEESKEWIRRSNQKLDSIGNWHQS | SEQ ID NO:45 |
| SIELNKAKSDLEESKEWIRRSNQKLDSIGNWHQSS | SEQ ID NO:46 |

TABLE 17-continued

ANTI-HUMAN PARAINFLUENZA VIRUS 3 (HPV3) PEPTIDES

| | |
|---|---|
| IELNKAKSDLEESKEWIRRSNQKLDSIGNWHQSST | SEQ ID NO:47 |
| ELNKAKSDLEESKEWIRRSNQKLDSIGNWHQSTT | SEQ ID NO:48 |
| TAAVALVEAKQARSDIEKLKEAIRDTNKAVQSVQS | SEQ ID NO:49 |
| AVALVEAKQARSDIEKLKEAIRDTNKAVQSVQSSI | SEQ ID NO:50 |
| LVEAKQARSDIEKLKEAIRDTNKAVQSVQSSIGNL | SEQ ID NO:51 |
| VEAKQARSDIEKLKEAIRDTNKAVQSVQSSIGNLI | SEQ ID NO:52 |
| EAKQARSDIEKLKEAIRDTNKAVQSVQSSIGNLIV | SEQ ID NO:53 |
| AKQARSDIEKLKEAIRDTNKAVQSVQSSIGNLIVA | SEQ ID NO:54 |
| KQARSDIEKLKEAIRDTNKAVQSVQSSIGNLIVAI | SEQ ID NO:55 |
| QARSDIEKLKEAIRDTNKAVQSVQSSIGNLIVAIK | SEQ ID NO:56 |
| ARSDIEKLKEAIRDTNKAVQSVQSSIGNLIVAIKS | SEQ ID NO:57 |
| RSDIEKLKEAIRDTNKAVQSVQSSIGNLIVAIKSV | SEQ ID NO:58 |
| SDIEKLKEAIRDTNKAVQSVQSSIGNLIVAIKSVQ | SEQ ID NO:59 |
| KLKEAIRDTNKAVQSVQSSIGNLIVAIKSVQDYVN | SEQ ID NO:60 |
| LKEAIRDTNKAVQSVQSSIGNLIVAIKSVQDYVNK | SEQ ID NO:61 |
| AIRDTNKAVQSVQSSIGNLIVAIKSVQDYVNKEIV | SEQ ID NO:62 |

The one letter amino acid code of Table 1 is used.

TABLE 18

ANTI-SIMIAN IMMUNODEFICIENCY VIRUS (SIV) PEPTIDES

| | |
|---|---|
| WQEWERKVDFLEENITALLEEAQIQQEKNMYELQK | SEQ ID NO:64 |
| QEWERKVDFLEENITALLEEAQIQQEKNMYELQKL | SEQ ID NO:65 |
| EWERKVDFLEENITALLEEAQIQQEKNMYELQKLN | SEQ ID NO:66 |

TABLE 18-continued

ANTI-SIMIAN IMMUNODEFICIENCY VIRUS (SIV) PEPTIDES

| | |
|---|---|
| WERKVDFLEENITALLEEAQIQQEKNMYELQKLNS | SEQ ID NO:67 |
| ERKVDFLEENITALLEEAQIQQEKNMYELQKLNSW | SEQ ID NO:68 |
| RKVDFLEENITALLEEAQIQQEKNMYELQKLNSWD | SEQ ID NO:69 |
| KVDFLEENITALLEEAQIQQEKNMYELQKLNSWDV | SEQ ID NO:70 |
| VDFLEENITALLEEAQIQQEKNMYELQKLNSWDVF | SEQ ID NO:71 |
| DFLEENITALLEEAQIQQEKNMYELQKLNSWDVFG | SEQ ID NO:72 |
| FLEENITALLEEAQIQQEKNMYELQKLNSWDVFGN | SEQ ID NO:73 |

The one letter amino acid code of Table 1 is used.

TABLE 19

ANTI-MEASLES VIRUS (MEV) PEPTIDES

| | |
|---|---|
| LHRIDLGPPISLERLDVGTNLGNAIAKLEAKELL | SEQ ID NO:76 |
| HRIDLGPPISLERLDVGTNLGNAIAKLEAKELLE | SEQ ID NO:77 |
| RIDLGPPISLERLDVGTNLGNAIAKLEAKELLES | SEQ ID NO:78 |
| IDLGPPISLERLDVGTNLGNAIAKLEAKELLESS | SEQ ID NO:79 |
| DLGPPISLERLDVGTNLGNAIAKLEAKELLESSD | SEQ ID NO:80 |
| LGPPISLERLDVGTNLGNAIAKLEAKELLESSDQ | SEQ ID NO:81 |
| GPPISLERLDVGTNLGNAIAKLEAKELLESSDQI | SEQ ID NO:82 |
| PPISLERLDVGTNLGNAIAKLEAKELLESSDQIL | SEQ ID NO:83 |
| PISLERLDVGTNLGNAIAKLEAKELLESSDQILR | SEQ ID NO:84 |
| SLERLDVGTNLGNAIAKLEAKELLESSDQILRSM | SEQ ID NO:85 |
| LERLDVGTNLGNAIAKLEAKELLESSDQILRSMK | SEQ ID NO:86 |

The one letter amino acid code of Table 1 is used.

---

We claim:

1. An antifusogenic peptide-albumin conjugate comprising:
an anti-fusogenic peptide comprising a maleimide containing group and an amino acid sequence, wherein said sequence is selected from the group consisting of SEQ ID NO:1, SEQ ID NO: 3, SEQ ID NO: 4, SEQ ID NO: 5, SEQ ID NO: 117, SEQ ID NO: 118, SEQ ID NO: 119, SEQ ID NO: 534, SEQ ID NO: 535, SEQ ID NO: 536, SEQ ID NO: 537, SEQ ID NO: 538, SEQ ID NO: 539, SEQ ID NO: 540, and SEQ ID NO: 541, wherein said sequence exhibits an anti-viral and antifusogenic activity against human immunodeficiency virus (HIV) and said peptide is covalently bonded to cysteine 34 of albumin through said maleimide containing group to form said peptide-albumin conjugate wherein the ratio of peptide to albumin in said conjugate is 1:1, and wherein said maleimide containing group is attached to said peptide without a linker or via a (2-amino)ethoxy acetic acid (AEA) or a [2-(2-amino) ethoxy] acetic acid (AEEA) linker.

2. The anti-fusogenic peptide-albumin conjugate of claim 1, wherein said amino acid sequence is SEQ ID NO:1.

3. An anti-fusogenic peptide-albumin conjugate of claim 1, wherein said amino acid sequence is selected from the group consisting of SEQ ID NO: 3, SEQ ID NO: 4, SEQ ID NO: 5, SEQ ID NO: 117, SEQ ID NO: 118, SEQ ID NO: 119, SEQ ID NO: 534, SEQ ID NO: 535, SEQ ID NO: 536, SEQ ID NO: 537, SEQ ID NO: 538, SEQ ID NO: 539, SEQ ID NO: 540, and SEQ ID NO: 541.

4. A composition for use in the treatment of acquired immune deficiency syndrome (AIDS) comprising, in a physiologically acceptable medium, an anti-fusogenic peptide-albumin conjugate comprising an anti-fusogenic peptide comprising a maleimide containing group and an amino acid sequence wherein said sequence is selected from the group consisting of SEQ ID NO:1, SEQ ID NO: 3, SEQ ID NO: 4, SEQ ID NO: 5, SEQ ID NO: 117, SEQ ID NO: 118, SEQ ID NO: 119, SEQ ID NO: 534, SEQ ID NO: 535, SEQ ID NO: 536, SEQ ID NO: 537, SEQ ID NO: 538, SEQ ID NO: 539, SEQ ID NO: 540, and SEQ ID NO: 541, wherein said sequence inhibits an anti-viral and anti-fusogenic activity against human immunodeficiency virus (HIV) and said peptide is covalently bonded to cysteine 34 of albumin through said maleimide containing group to form said anti-viral peptide-albumin conjugate, wherein the ratio of peptide to albumin in said conjugate is 1:1, wherein said maleimide containing group is attached to said peptide without a linker or via a (2-amino)ethoxy acetic acid (AEA) or a [2-(2-amino) ethoxy] acetic acid (AEEA) linker.

5. The composition of claim 4, wherein said amino acid sequence is SEQ ID NO:1.

6. The composition of claim 4, wherein said amino acid sequence is selected from the group consisting of SEQ ID NO: 3, SEQ ID NO: 4, SEQ ID NO: 5, SEQ ID NO: 117, SEQ ID NO: 118, SEQ ID NO: 119, SEQ ID NO: 534, SEQ ID NO: 535, SEQ ID NO: 536, SEQ ID NO: 537, SEQ ID NO: 538, SEQ ID NO: 539, SEQ ID NO: 540, and SEQ ID NO: 541.

7. A composition comprising the anti-fusogenic peptide-albumin conjugate of claim 1 in a physiologically acceptable medium.

8. The composition of claim 7, wherein said amino acid sequence is SEQ ID NO:1.

9. The composition of claim 7, wherein said amino acid sequence is selected from the group consisting of SEQ ID NO:3, SEQ ID NO:4, SEQ ID NO:5, SEQ ID NO: 117, SEQ ID NO:118, SEQ ID NO:119, SEQ ID NO:534; SEQ ID NO:535, SEQ ID NO:536; SEQ ID NO:537, SEQ ID NO:538, SEQ ID NO:539, SEQ ID NO:540, and SEQ ID NO: 541.

10. The anti-fusogenic peptide-albumin conjugate of claim 1, wherein said albumin is serum albumin.

11. The anti-fusogenic peptide-albumin conjugate of claim 10, wherein said albumin is human serum albumin.

12. The anti-fusogenic peptide-albumin conjugate of claim 1, wherein said amino acid sequence is SEQ ID NO:3.

13. The anti-fusogenic peptide-albumin conjugate of claim 1, wherein said amino acid sequence is SEQ ID NO:4.

14. The anti-fusogenic peptide-albumin conjugate of claim 1, wherein said amino acid sequence is SEQ ID NO: 5.

15. The anti-fusogenic peptide-albumin conjugate of claim 1, wherein said amino acid sequence is SEQ ID NO: 117.

16. The anti-fusogenic peptide-albumin conjugate of claim 1, wherein said amino acid sequence is SEQ ID NO: 118.

17. The anti-fusogenic peptide-albumin conjugate of claim 1, wherein said amino acid sequence is SEQ ID NO: 119.

18. The anti-fusogenic peptide-albumin conjugate of claim 1, wherein said amino acid sequence is SEQ ID NO: 534.

19. The anti-fusogenic peptide-albumin conjugate of claim 1, wherein said amino acid sequence is SEQ ID NO: 535.

20. The anti-fusogenic peptide-albumin conjugate of claim 1, wherein said amino acid sequence is SEQ ID NO: 536.

21. The anti-fusogenic peptide-albumin conjugate of claim 1, wherein said amino acid sequence is SEQ ID NO: 537.

22. The anti-fusogenic peptide-albumin conjugate of claim 1, wherein said amino acid sequence is SEQ ID NO: 538.

23. The anti-fusogenic peptide-albumin conjugate of claim 1, wherein said amino acid sequence is SEQ ID NO: 539.

24. The anti-fusogenic peptide-albumin conjugate of claim 1, wherein said amino acid sequence is SEQ ID NO: 540.

25. The anti-fusogenic peptide-albumin conjugate of claim 1, wherein said amino acid sequence is SEQ ID NO: 541.

26. The composition of claim 4, wherein said amino acid sequence is SEQ ID NO: 3.

27. The composition of claim 4, wherein said amino acid sequence is SEQ ID NO: 4.

28. The composition of claim 4, wherein said amino acid sequence is SEQ ID NO: 5.

29. The composition of claim 4, wherein said amino acid sequence is SEQ ID NO: 117.

30. The composition of claim 4, wherein said amino acid sequence is SEQ ID NO: 118.

31. The composition of claim 4, wherein said amino acid sequence is SEQ ID NO: 119.

32. The composition of claim 4, wherein said amino acid sequence is SEQ ID NO: 534.

33. The composition of claim 4, wherein said amino acid sequence is SEQ ID NO: 535.

34. The composition of claim 4, wherein said amino acid sequence is SEQ ID NO: 536.

35. The composition of claim 4, wherein said amino acid sequence is SEQ ID NO: 537.

36. The composition of claim 4, wherein said amino acid sequence is SEQ ID NO: 538.

37. The composition of claim 4, wherein said amino acid sequence is SEQ ID NO: 539.

38. The composition of claim 4, wherein said amino acid sequence is SEQ ID NO: 540.

39. The composition of claim 4, wherein said amino acid sequence is SEQ ID NO: 541.

40. The anti-fusogenic peptide-albumin conjugate of claim 1, wherein the maleimide containing group is maleimidopropionic acid (MPA) or gamma-maleimide-butyralamide (GMBA).

41. The anti-fusogenic peptide-albumin conjugate of claim 1, wherein the maleimide containing group is attached to the peptide via the (2-amino)ethoxy acetic acid (AEA) or the [2-(2-amino) ethoxy] acetic acid (AEEA) linker.

42. The anti-fusogenic peptide-albumin conjugate of claim 1, wherein the maleimide containing group is attached to the peptide without a linking group.

43. The composition of claim 4, wherein the maleimide containing group is maleimidopropionic acid (MPA) or gamma-maleimide-butyralamide (GMBA).

44. The composition of claim 4, wherein the maleimide containing group is attached to the peptide via the (2-amino) ethoxy acetic acid (AEA) or the [2-(2-amino) ethoxy] acetic acid (AEEA) linker.

45. The composition of claim 4, wherein the maleimide containing group is attached to the peptide without a linking group.

46. The anti-fusogenic peptide-albumin conjugate of claim 1, wherein the peptide exhibits anti-viral and anti-fusogenic activity by modulation of a viral-cellular fusion process involving a coiled-coil peptide structure.

47. The composition of claim 4, wherein the peptide exhibits anti-viral and anti-fusogenic activity by modulation of a viral-cellular fusion process involving a coiled-coil peptide structure.

* * * * *

UNITED STATES PATENT AND TRADEMARK OFFICE
CERTIFICATE OF CORRECTION

PATENT NO.        : 7,582,301 B1
APPLICATION NO.   : 09/623533
DATED             : September 1, 2009
INVENTOR(S)       : Dominique P. Bridon et al.

It is certified that error appears in the above-identified patent and that said Letters Patent is hereby corrected as shown below:

On the Title Pg, Item (75) the Inventor Robert P. Dufresne of Wellseley, MA should be listed as "Robert S. Dufresne of Wellseley, MA".

Signed and Sealed this

Twenty-seventh Day of October, 2009

David J. Kappos
*Director of the United States Patent and Trademark Office*